(12) United States Patent
Gottschling et al.

(10) Patent No.: US 8,278,336 B2
(45) Date of Patent: Oct. 2, 2012

(54) COMPOUNDS

(75) Inventors: Dirk Gottschling, Mittelbiberach (DE); Georg Dahmann, Attenweiler (DE); Henri Doods, Warthausen (DE); Annekatrin Heimann, Biberach (DE); Stephan Georg Mueller, Warthausen (DE); Klaus Rudolf, Warthausen (DE); Gerhard Georg Schaenzle, Warthausen (DE); Dirk Stenkamp, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 178 days.

(21) Appl. No.: 12/743,013

(22) PCT Filed: Nov. 21, 2008

(86) PCT No.: PCT/EP2008/065963
§ 371 (c)(1),
(2), (4) Date: Aug. 4, 2010

(87) PCT Pub. No.: WO2009/065921
PCT Pub. Date: May 28, 2009

(65) Prior Publication Data
US 2010/0324028 A1 Dec. 23, 2010

(30) Foreign Application Priority Data
Nov. 22, 2007 (EP) .................................. 07121353

(51) Int. Cl.
- A61K 31/44 (2006.01)
- C07D 213/62 (2006.01)
- C07D 213/78 (2006.01)
- C07D 213/72 (2006.01)

(52) U.S. Cl. ......... 514/352; 514/354; 546/298; 546/304
(58) Field of Classification Search .................. 514/352, 514/354; 546/298, 304
See application file for complete search history.

(56) References Cited

FOREIGN PATENT DOCUMENTS
WO 0222592 A2 3/2002
WO 2005030751 A2 4/2005

OTHER PUBLICATIONS
Tepper SJ, Stillman MJ. Clinical and preclinical rationale for CGRP-receptor antagonists in the treatment of migraine. Headache. Sep. 2008;48(8):1259-68.*
International Search Report, Form PCT/ISA/210, for corresponding PCT/EP2008/065963, Date of mailing Jan. 1, 2009.

* cited by examiner

Primary Examiner — Paul Zarek
(74) Attorney, Agent, or Firm — Michael P. Morris; Alan R. Stempel

(57) ABSTRACT

The present invention relates to new CGRP-antagonists of general formulae Ia and Ib

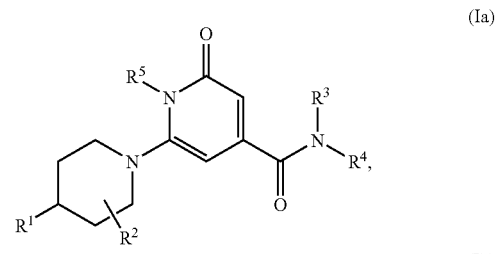

(Ia)

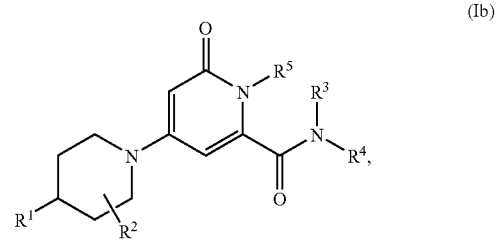

(Ib)

wherein $R^1$, $R^2$, $R^3$, $R^4$ and $R^5$ are defined as mentioned below, the tautomers, the isomers, the diastereomers, the enantiomers, the hydrates, the mixtures and the salts thereof as well as the hydrates of the salts, particularly the physiologically acceptable salts thereof with inorganic or organic acids or bases, pharmaceutical compositions containing these compounds, the use thereof and processes for the preparation thereof.

17 Claims, No Drawings

COMPOUNDS

The present invention relates to new CGRP-antagonists of general formulae Ia and Ib

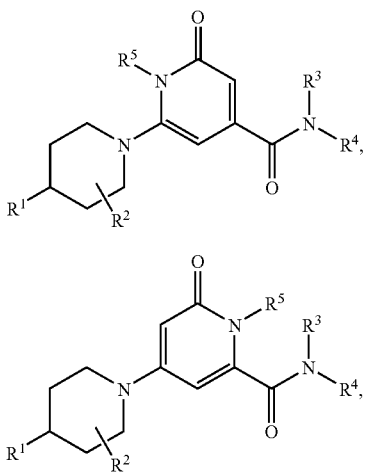

wherein $R^1$, $R^2$, $R^3$, $R^4$ and $R^5$ are defined as mentioned below, the tautomers, the isomers, the diastereomers, the enantiomers, the hydrates, the mixtures and the salts thereof as well as the hydrates of the salts, particularly the physiologically acceptable salts thereof with inorganic or organic acids or bases, pharmaceutical compositions containing these compounds, the use thereof and processes for the preparation thereof.

DETAILED DESCRIPTION OF THE INVENTION

In the above general formulae Ia and Ib in a first embodiment
$R^1$ denotes a group of general formula II

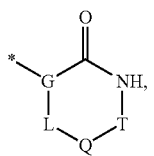

wherein
G-L denotes N, N—C($R^{1.1}$)$_2$, C=C($R^{1.1}$), C=N, C($R^{1.1}$), C($R^{1.1}$)—C($R^{1.1}$)$_2$, C($R^{1.1}$)—C($R^{1.1}$)$_2$—C($R^{1.1}$)$_2$, C=C($R^{1.1}$)—C($R^{1.1}$)$_2$, C($R^{1.1}$)—C($R^{1.1}$)=C($R^{1.1}$), C($R^{1.1}$)—C($R^{1.1}$)$_2$—N($R^{1.2}$), C=C($R^{1.1}$)—N($R^{1.2}$), C($R^{1.1}$)—C($R^{1.1}$)=N, C($R^{1.1}$)—N($R^{1.2}$)—C($R^{1.1}$)$_2$, C=N—C($R^{1.1}$)$_2$, C($R^{1.1}$)—N=C($R^{1.1}$), C($R^{1.1}$)—N($R^{1.2}$)—N($R^{1.2}$), C=N—N($R^{1.2}$), N—C($R^{1.1}$)$_2$—C($R^{1.1}$)$_2$, N—C($R^{1.1}$)=C($R^{1.1}$), N—C($R^{1.1}$)$_2$—N($R^{1.2}$), N—C($R^{1.1}$)=N, N—N($R^{1.2}$)—C($R^{1.1}$)$_2$ or N—N=C($R^{1.1}$), Q-T denotes C($R^{1.3}$)$_2$—C($R^{1.3}$)$_2$, C($R^{1.3}$)=C($R^{1.3}$), N=C($R^{1.3}$), C($R^{1.3}$)$_2$—C(=O), C(=O)—C($R^{1.3}$)$_2$, C($R^{1.3}$)$_2$—S(O), or C($R^{1.3}$)$_2$—N($R^{1.3}$), while a group C($R^{1.3}$)$_2$ contained in Q-T may also denote a cyclic group which is selected from among $C_{3-6}$-cycloalkyl, $C_{5-6}$-cycloalkenyl or heterocyclyl, or in a group C($R^{1.3}$)$_2$—C($R^{1.3}$)$_2$, C($R^{1.3}$)=C($R^{1.3}$) or C($R^{1.3}$)$_2$—N($R^{1.3}$) contained in Q-T in each case a group $R^{1.3}$ together with an adjacent group $R^{1.3}$ and the atoms to which these groups are bound may also denote a $C_{3-6}$-cycloalkyl, $C_{5-6}$-cycloalkenyl, heterocyclyl, aryl or heteroaryl group, which may be substituted independently of one another by 1, 2 or 3 substituents $R^{1.3.1}$, $R^{1.1}$ denotes
(a) H,
(b) $C_{1-6}$-alkyl, —CN, —OH, —O—$C_{1-3}$-alkyl,
(c) a $C_{1-3}$-alkyl- or $C_{1-3}$-alkyl-O— group wherein each methylene group is substituted by up to two fluorine atoms and each methyl group is substituted by up to three fluorine atoms, $R^{1.2}$ denotes H or $C_{1-6}$-alkyl, $R^{1.3}$ independently of one another denote
(a) H, $C_{1-6}$-alkyl, $C_{2-6}$-alkenyl, $C_{2-6}$-alkynyl, $C_{3-6}$-cycloalkyl,
(b) an aryl group optionally substituted by 1, 2 or 3 substituents $R^{1.3.2}$, wherein the substituents $R^{1.3.2}$ may be identical or different,
(c) a heteroaryl group optionally substituted by 1, 2 or 3 substituents $R^{1.3.2}$, wherein the substituents $R^{1.3.2}$ may be identical or different,
(d) a heterocyclic group optionally substituted by 1, 2 or 3 substituents $R^{1.3.2}$, wherein the substituents $R^{1.3.2}$ may be identical or different, $R^{1.3.1}$ denotes
(a) H, halogen, $C_{1-6}$-alkyl, $C_{3-6}$-cycloalkyl,
(b) —O—$R^{1.3.1.1}$, —O—$C_{1-6}$-alkylene-N$R^{1.3.1.2}R^{1.3.1.3}$, —O—(CH$_2$)$_s$—O—$R^{1.3.1.1}$, —CO$_2$—$R^{1.3.1.1}$, —C(O)—N$R^{1.3.1.2}R^{1.3.1.3}$, —O—C(O)—N$R^{1.3.1.2}R^{1.3.1.3}$, —N$R^{1.3.1.1}$—C(O)—N$R^{1.3.1.2}R^{1.3.1.3}$, —N$R^{1.3.1.2}$—C(O)—$R^{1.3.1.3}$, —N$R^{1.3.1.2}$—C(O)—O—$R^{1.3.1.3}$, —SO$_2$—N$R^{1.3.1.2}R^{1.3.1.3}$, —N$R^{1.3.1.2}$—SO$_2$—$R^{1.3.1.3}$, —S(O)$_m$—$R^{1.3.1.2}$, —CN, —N$R^{1.3.1.2}R^{1.3.1.3}$, —N$R^{1.3.1.1}$—C(O)—N$R^{1.3.1.2}R^{1.3.1.3}$, —O—C(O)—$R^{1.3.1.1}$,
(c) a $C_{1-3}$-alkyl or $C_{1-3}$-alkyl-O— group wherein each methylene group is substituted by up to two fluorine atoms and each methyl group is substituted by up to three fluorine atoms,
(d) an aryl group substituted by 1, 2 or 3 substituents $R^{1.3.1.1}$, wherein the substituents $R^{1.3.1.1}$ may be identical or different,
(e) a heteroaryl group substituted by 1, 2 or 3 substituents $R^{1.3.1.1}$, wherein the substituents $R^{1.3.1.1}$ may be identical or different,
(f) a heterocyclic group substituted by 1, 2 or 3 substituents $R^{1.3.1.1}$, wherein the substituents $R^{1.3.1.1}$ may be identical or different, $R^{1.3.2}$ denotes
(a) halogen, $C_{1-6}$-alkyl, $C_{3-6}$-cycloalkyl,
(b) —O—$R^{1.3.2.1}$, —O—(CH$_2$)$_s$—O—$R^{1.3.2.1}$, —CO$_2R^{1.3.2.1}$, —C(O)—N$R^{1.3.2.2}R^{1.3.2.3}$, —O—(CO)—N$R^{1.3.2.2}R^{1.3.2.3}$, —N($R^{1.3.2.1}$)—C(O)—N$R^{1.3.2.2}R^{1.3.2.3}$, —N($R^{1.3.2.2}$)—C(O)—$R^{1.3.2.3}$, —N($R^{1.3.2.2}$)—C(O)—O—$R^{1.3.2.3}$, —SO$_2$—N$R^{1.3.2.2}R^{1.3.2.3}$, —N($R^{1.3.2.2}$)—SO$_2$—$R^{1.3.2.3}$, —S(O)$_m$—$R^{1.3.2.2}$, —CN, —N$R^{1.3.2.2}R^{1.3.2.3}$, —N($R^{1.3.2.1}$)—C(O)—N$R^{1.3.2.2}R^{1.3.2.3}$, —O—C(O)—$R^{1.3.2.1}$ or
(c) a $C_{1-3}$-alkyl group wherein each methylene group is substituted by up to two fluorine atoms and each methyl group is substituted by up to three fluorine atoms, $R^{1.3.1.1}$ denotes
  (a) H,
  (b) $C_{1-6}$-alkyl, $C_{3-6}$-cycloalkyl, aryl, heteroaryl, benzyl which may be substituted by a group $R^{1.3.1.1.1}$, or
  (c) a $C_{1-3}$-alkyl group wherein each methylene group is substituted by up to two fluorine atoms and each methyl group is substituted by up to three fluorine atoms,
$R^{1.3.1.1.1}$ denotes halogen, HO— or $C_{1-6}$-alkyl-O—,
$R^{1.3.1.2}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms,
$R^{1.3.1.3}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or
$R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$ or fluorine, wherein the substituents $R^{1.3.1.1}$ are independent of one another,
$R^{1.3.2.1}$ denotes
  (a) H,
  (b) $C_{1-6}$-alkyl, $C_{3-6}$-cycloalkyl, aryl, heteroaryl, benzyl which may be substituted by a group $R^{1.3.2.1.1}$, or
  (c) a $C_{1-3}$-alkyl group wherein each methylene group is substituted by up to two fluorine atoms and each methyl group is substituted by up to three fluorine atoms,
$R^{1.3.2.1.1}$ denotes halogen, HO— or $C_{1-6}$-alkyl-O—,
$R^{1.3.2.2}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms,
$R^{1.3.2.3}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or
$R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$ or fluorine, wherein the substituents $R^{1.3.2.1}$ are independent of one another,
m denotes one of the numbers 0, 1 or 2,
s denotes one of the numbers 1, 2 or 3,
$R^2$ denotes
  (a) H,
  (b) F, —CN, $C_{1-3}$-alkyl, —$CO_2$—$R^{2.1}$ or
  (c) a $C_{1-3}$-alkyl group wherein each methylene group is substituted by up to two fluorine atoms and each methyl group is substituted by up to three fluorine atoms,
$R^{2.1}$ denotes H or $C_{1-6}$-alkyl,
$R^3$ denotes
  (a) H,
  (b) $C_{1-6}$-alkylene-$R^{3.1}$,
  (c) a $C_{3-6}$-cycloalkyl group substituted by one or two groups $R^{3.2}$,
  (d) a $C_{5-7}$-cycloalkenyl group substituted by one or two groups $R^{3.2}$,
  (e) an aryl group substituted by one or two groups $R^{3.2}$,
  (f) a heterocyclyl group substituted by one or two groups $R^{3.2}$,
  (g) a $C_{5-7}$-cycloalkyl group which may be fused to an aryl or heteroaryl group and is additionally substituted by one or two groups $R^{3.2}$,
  (h) a heteroaryl group substituted by one or two groups $R^{3.2}$,
  (i) a $C_{1-3}$-alkyl group wherein each methylene group is substituted by up to two fluorine atoms and each methyl group is substituted by up to three fluorine atoms,
$R^{3.1}$ denotes
  (a) H,
  (b) an aryl group substituted by the groups $R^{3.1.1}$ and $R^{3.1.2}$,
  (c) a heteroaryl group substituted by the groups $R^{3.1.1}$ and $R^{3.1.2}$,
$R^{3.1.1}$ denotes
  (a) H,
  (b) halogen, $C_{1-3}$-alkyl, —OH, —CN, —O—$C_{1-3}$-alkyl, —O—C(O)—$C_{1-3}$-alkyl, —$NR^{3.1.1.1}R^{3.1.1.2}$, —S(O), —$C_{1-3}$-alkyl, —$NR^{3.1.1.1}$—C(O)—$C_{1-3}$-alkyl, —C(O)—$NR^{3.1.1.1}R^{3.1.12}$, —C(O)—O—$R^{3.1.1.3}$, —$NR^{3.1.1.1}$—C(O)—O—$C_{1-3}$-alkyl, —O—C(O)—$NR^{3.1.1.1}R^{3.1.12}$,
  (c) a $C_{1-3}$-alkyl- or —O—$C_{1-3}$-alkyl group wherein each methylene group is substituted by up to two fluorine atoms and each methyl group is substituted by up to three fluorine atoms,
$R^{3.1.1.1}$ denotes H, $C_{1-3}$-alkyl and
$R^{3.1.1.2}$ denotes H, $C_{1-3}$-alkyl, or
$R^{3.1.1.1}$ and $R^{3.1.1.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$,
$R^{3.1.1.3}$ denotes H, $C_{1-3}$-alkyl,
$R^{3.1.2}$ denotes
  (a) H,
  (b) halogen, $C_{1-3}$-alkyl, —OH, —CN, —O—$C_{1-3}$-alkyl,
  (c) a $C_{1-3}$-alkyl- or —O—$C_{1-3}$-alkyl group wherein each methylene group is substituted by up to two fluorine atoms and each methyl group is substituted by up to three fluorine atoms, or
$R^{3.2}$ independently of one another denote
  (a) H,
  (b) halogen, $C_{1-3}$-alkyl, —OH, —CN, —O—$C_{1-3}$-alkyl, —O—C(O)—$C_{1-3}$-alkyl, —$NR^{3.2.1}R^{3.2.2}$, —$S(O)_m$—$C_{1-3}$-alkyl, —$NR^{3.2.1}$—C(O)—$C_{1-3}$-alkyl, —C(O)—$NR^{3.2.1}R^{3.2.2}$, —C(O)—O—$R^{3.2.3}$, —$NR^{3.2.1}$—C(O)—O—$C_{1-3}$-alkyl, —O—C(O)—$NR^{3.2.1}R^{3.2.2}$,
  (c) a $C_{1-3}$-alkyl- or —O—$C_{1-3}$-alkyl group wherein each methylene group is substituted by up to two fluorine atoms and each methyl group is substituted by up to three fluorine atoms, $R^{3.2.1}$ denotes H, $C_{1-3}$-alkyl and
$R^{3.2.2}$ denotes H, $C_{1-3}$-alkyl, or
$R^{3.2.1}$ and $R^{3.2.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$,
$R^{3.2.3}$ denotes H, $C_{1-3}$-alkyl,
$R^4$ denotes
- (a) H,
- (b) $C_{1-6}$-alkylene-$R^{4.1}$,
- (c) a $C_{3-6}$-cycloalkyl group substituted by one or two groups $R^{4.2}$,
- (d) a $C_{6-7}$-cycloalkenyl group substituted by one or two groups $R^{4.2}$,
- (e) an aryl group substituted by one or two groups $R^{4.2}$,
- (f) a heterocyclyl group substituted by one or two groups $R^{4.2}$,
- (g) a $C_{6-7}$-cycloalkyl group which may be fused to an aryl or heteroaryl group, while the resultant bicyclic group is additionally substituted by one or two groups $R^{4.2}$,
- (h) a heteroaryl group substituted by one or two groups $R^{4.2}$,
- (i) a $C_{1-3}$-alkyl group wherein each methylene group is substituted by up to two fluorine atoms and each methyl group is substituted by up to three fluorine atoms, $R^{4.1}$ denotes
- (a) H,
- (b) an aryl group substituted by the groups $R^{4.1.1}$ and $R^{4.1.2}$,
- (c) a heteroaryl group substituted by the groups $R^{4.1.1}$ and $R^{4.1.2}$, $R^{4.1.1}$ denotes
- (a) H,
- (b) halogen, $C_{1-3}$-alkyl, —OH, —CN, —O—$C_{1-3}$-alkyl, —O—C(O)—$C_{1-3}$-alkyl, —NR$^{4.1.1.1}$R$^{4.1.1.2}$, —S(O)$_m$—$C_{1-3}$-alkyl, —NR$^{4.1.1.1}$—C(O)—$C_{1-3}$-alkyl, —C(O)—NR$^{4.1.1.1}$R$^{4.1.1.2}$, —C(O)—O—R$^{4.1.1.3}$, —NR$^{4.1.1.1}$—C(O)—O—$C_{1-3}$-alkyl, —O—C(O)—NR$^{4.1.1.1}$R$^{4.1.1.2}$,
- (c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.1}$ denotes H, $C_{1-3}$-alkyl and
$R^{4.1.1.2}$ denotes H, $C_{1-3}$-alkyl, or
$R^{4.1.1.1}$ and $R^{4.1.1.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$,
$R^{4.1.1.3}$ denotes H, $C_{1-3}$-alkyl,
$R^{4.1.2}$ denotes
- (a) H,
- (b) halogen, $C_{1-3}$-alkyl, —OH, —CN, —O—$C_{1-3}$-alkyl,
- (c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ independently of one another denote
- (a) H,
- (b) halogen, $C_{1-3}$-alkyl, —OH, —CN, —O—$C_{1-3}$-alkyl, —O—C(O)—$C_{1-3}$-alkyl, —NR$^{4.2.1}$R$^{4.2.2}$, —S(O)$_m$—$C_{1-3}$-alkyl, —NR$^{4.2.1}$—C(O)—$C_{1-3}$-alkyl, —C(O)—NR$^{4.2.1}$R$^{4.2.2}$, —C(O)—O—R$^{4.2.3}$, —NR$^{4.2.1}$—C(O)—O—$C_{1-3}$-alkyl, —O—C(O)—NR$^{4.2.1}$R$^{4.2.2}$,
- (c) a $C_{1-3}$-alkyl or —O—$C_{1-3}$-alkyl group wherein each methylene group is substituted by up to two fluorine atoms and each methyl group is substituted by up to three fluorine atoms, $R^{4.2.1}$ denotes H, $C_{1-3}$-alkyl and
$R^{4.2.2}$ denotes H, $C_{1-3}$-alkyl, or
$R^{4.2.1}$ and $R^{4.2.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$,
$R^{4.2.3}$ denotes H, $C_{1-3}$-alkyl, $R^3$ and $R^4$ together with the nitrogen atom to which they are bound denote:
- (a) a saturated 5-, 6- or 7-membered heterocyclic group which is substituted at a carbon atom by a group $R^{4.3}$ or by two groups $R^{4.3}$ and $R^{4.4}$,
- (b) a saturated 5-, 6- or 7-membered heterocyclic group which is substituted at two adjacent carbon atoms by in each case a group $R^{4.3}$ and $R^{4.4}$,
- (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
- (d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
- (e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or
- (f) a heteroaryl group which is substituted at 1, 2 or 3 carbon atoms by in each case a group $R^{4.5}$, $R^{4.3}$ independently of one another denote
- (a) H, $C_{1-3}$-alkyl, $C_{2-6}$-alkynyl, aryl, —$C_{1-3}$-alkylene-$R^{4.3.1}$, $C_{1-3}$-alkyl-O—C(O)—, HO—C(O)—, F, —O—$C_{1-3}$-alkyl, —OH, —CN,
- (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3.1}$ denotes H, $C_{1-3}$-alkyl-O—C(O)—, —NH$_2$, ($C_{1-4}$-alkyl)-NH, ($C_{1-4}$-alkyl)$_2$N, $C_{3-6}$-cycloalkyl, heterocyclyl, heteroaryl, aryl, $R^{4.4}$ denotes
- (a) H, $C_{1-3}$-alkyl-, —OH, —O—$C_{1-3}$-alkyl or
- (b) a $C_{1-3}$-alkyl or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl-, $C_{5-6}$-cycloalkenyl- or heterocyclyl group, $R^{4.5}$ independently of one another denote
  (a) H,
  (b) halogen, $C_{1-3}$-alkyl, —OH, —O—$C_{1-3}$-alkyl, —S(O)$_m$—$C_{1-3}$-alkyl, —NR$^{4.5.2}$R$^{4.5.3}$, —CN, —C(O)—O—R$^{4.5.1}$, —C(O)—NR$^{4.5.2}$R$^{4.5.3}$,
  (c) a $C_{1-3}$-alkyl or —O—$C_{1-3}$-alkyl group wherein each methylene group is substituted by up to two fluorine atoms and each methyl group is substituted by up to three fluorine atoms,
  (d) aryl, heteroaryl,
$R^{4.5.1}$ denotes H,
$R^{4.5.2}$ denotes H,
$R^{4.5.3}$ denotes H, $C_{1-3}$-alkyl, or
$R^{4.5.2}$ and $R^{4.5.3}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —OCF$_3$, $C_{1-3}$-alkyl and CF$_3$,
$R^5$ denotes H, —CH$_2$—R$^{5.1}$ or benzyl, and
$R^{5.1}$ denotes a $C_{1-3}$-alkyl group wherein each methylene group is substituted by up to two fluorine atoms and each methyl group is substituted by up to three fluorine atoms,
the tautomers, the diastereomers, the enantiomers, the hydrates, the mixtures thereof and the salts thereof as well as the hydrates of the salts, particularly the physiologically acceptable salts thereof with inorganic or organic acids or bases.

A second embodiment of the present invention comprises the compounds of the above general formulae Ia and Ib, wherein $R^2$, $R^3$, $R^4$ and $R^5$ are defined as hereinbefore in the first embodiment and
$R^1$ denotes a group of general formula II

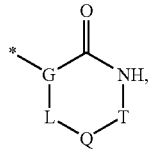
(II)

wherein
G-L denotes N, N—C(R$^{1.1}$)$_2$, C=C(R$^{1.1}$), C=N, C(R$^{1.1}$), C(R$^{1.1}$)—C(R$^{1.1}$)$_2$, C(R$^{1.1}$)—C(R$^{1.1}$)$_2$—C(R$^{1.1}$)$_2$, C=C(R$^{1.1}$)—C(R$^{1.1}$)$_2$, C(R$^{1.1}$)—C(R$^{1.1}$)=C(R$^{1.1}$), C(R$^{1.1}$)—C(R$^{1.1}$)$_2$—N(R$^{1.2}$), C=C(R$^{1.1}$)—N(R$^{1.2}$), C(R$^{1.1}$)—C(R$^{1.1}$)=N, C(R$^{1.1}$)—N(R$^{1.2}$)—C(R$^{1.1}$)$_2$, C=N—C(R$^{1.1}$)$_2$, C(R$^{1.1}$)—N=C(R$^{1.1}$), C(R$^{1.1}$)—N(R$^{1.2}$)—N(R$^{1.2}$), C=N—N(R$^{1.3}$), N—C(R$^{1.1}$)$_2$—C(R$^{1.1}$)$_2$, N—C(R$^{1.1}$)=C(R$^{1.1}$), N—C(R$^{1.1}$)$_2$—N(R$^{1.2}$), N—C(R$^{1.1}$)=N, N—N(R$^{1.2}$)—C(R$^{1.1}$)$_2$ or N—N=C(R$^{1.1}$),
Q-T denotes C(R$^{1.3}$)$_2$—C(R$^{1.3}$)$_2$, C(R$^{1.3}$)=C(R$^{1.3}$), N=C(R$^{1.3}$), C(R$^{1.3}$)$_2$—C(=O), C(=O)—C(R$^{1.3}$)$_2$, C(R$^{1.3}$)$_2$—S(O)$_m$ or C(R$^{1.3}$)$_2$—N(R$^{1.3}$),
  while a group C(R$^{1.3}$)$_2$ contained in Q-T may also denote a cyclic group which is selected from among cyclobutyl, cyclopentyl, cyclohexyl, cyclopentenyl, cyclohexenyl, dioxanyl, morpholinyl, thiomorpholinyl, thiomorpholinyl-S-oxide, thiomorpholinyl-S-dioxide, azetidinyl, pyrrolidinyl, piperidinyl, tetrahydrofuranyl, tetrahydropyranyl and piperazinyl, or
  in a group C(R$^{1.3}$)$_2$—C(R$^{1.3}$)$_2$, C(R$^{1.3}$)=C(R$^{1.3}$) or C(R$^{1.3}$)$_2$—N(R$^{1.3}$) contained in Q-T in each case a group R$^{1.3}$ together with an adjacent group R$^{1.3}$ and the atoms to which these groups are bound may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-S-oxide, thiomorpholinyl-S-dioxide, 1H-quinolinyl-2-one, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another denote by 1, 2 or 3 substituents R$^{1.3.1}$,
$R^{1.1}$ denotes
  (a) H,
  (b) $C_{1-6}$-alkyl, —CN, —OH, —O—$C_{1-3}$-alkyl,
  (c) a $C_{1-3}$-alkyl- or $C_{1-3}$-alkyl-O— group wherein each methylene group is substituted by up to two fluorine atoms and each methyl group is substituted by up to three fluorine atoms,
$R^{1.2}$ denotes H or $C_{1-6}$-alkyl,
$R^{1.3}$ independently of one another denote
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents R$^{1.3.2}$, wherein the substituents R$^{1.3.2}$ may be identical or different,
  (c) a heteroaryl group optionally substituted by 1, 2 or 3 substituents R$^{1.3.2}$, wherein the substituents R$^{1.3.2}$ may be identical or different,
  (d) a heterocyclic group optionally substituted by 1, 2 or 3 substituents R$^{1.3.2}$, wherein the substituents R$^{1.3.2}$ may be identical or different,
$R^{1.3.1}$ denotes
  (a) H, halogen, $C_{1-6}$-alkyl, $C_{3-6}$-cycloalkyl,
  (b) —O—R$^{1.3.1.1}$, —O—$C_{1-6}$-alkylene-NR$^{1.3.1.2}$R$^{1.3.1.3}$, —O—(CH$_2$)$_s$—O—R$^{1.3.1.1}$, —CO$_2$—R$^{1.3.1.1}$, C(O)—NR$^{1.3.1.2}$R$^{1.3.1.3}$, —O—C(O)—NR$^{1.3.1.2}$R$^{1.3.1.3}$, —NR$^{1.3.1.1}$—C(O)—NR$^{1.3.1.2}$R$^{1.3.1.3}$, —NR$^{1.3.1.2}$—C(O)—R$^{1.3.1.3}$, —NR$^{1.3.1.2}$—C(O)—O—R$^{1.3.1.3}$, —SO$_2$—NR$^{1.3.1.2}$R$^{1.3.1.3}$, —NR$^{1.3.1.2}$—SO$_2$—R$^{1.3.1.3}$, —S(O)$_m$—R$^{1.3.1.2}$, —CN, —NR$^{1.3.1.2}$R$^{1.3.1.3}$, —NR$^{1.3.1.1}$—C(O)—NR$^{1.3.1.2}$R$^{1.3.1.3}$, —O—C(O)—R$^{1.3.1.1}$,
  (c) a $C_{1-3}$-alkyl- or $C_{1-3}$-alkyl-O— group wherein each methylene group is substituted by up to two fluorine atoms and each methyl group is substituted by up to three fluorine atoms,
  (d) an aryl group substituted by 1, 2 or 3 substituents R$^{1.3.1.1}$, wherein the substituents R$^{1.3.1.1}$ may be identical or different,
  (e) a heteroaryl group substituted by 1, 2 or 3 substituents R$^{1.3.1.1}$, wherein the substituents R$^{1.3.1.1}$ may be identical or different,
  (f) a heterocyclic group substituted by 1, 2 or 3 substituents R$^{1.3.1.1}$, wherein the substituents R$^{1.3.1.1}$ may be identical or different,
$R^{1.3.2}$ denotes
  (a) halogen, $C_{1-6}$-alkyl, $C_{3-6}$-cycloalkyl,
  (b) —O—R$^{1.3.2.1}$, —O—(CH$_2$)$_s$—O—R$^{1.3.2.1}$, —CO$_2$R$^{1.3.2.1}$, —C(O)—NR$^{1.3.2.2}$R$^{1.3.2.3}$, —O—(CO)—NR$^{1.3.2.2}$R$^{1.3.2.3}$, —N(R$^{1.3.2.1}$)—C(O)—NR$^{1.3.2.2}$R$^{1.3.2.3}$, —N(R$^{1.3.2.2}$)—C(O)—R$^{1.3.2.3}$, —N(R$^{1.3.2.2}$)—C(O)—O—R$^{1.3.2.3}$, —SO$_2$—NR$^{1.3.2.2}$R$^{1.3.2.3}$, —N(R$^{1.3.2.2}$)—SO$_2$—R$^{1.3.2.3}$, —S(O)$_m$—R$^{1.3.2.2}$, —CN, —NR$^{1.3.2.2}$R$^{1.3.2.3}$, —N(R$^{1.3.2.1}$)—C(O)—NR$^{1.3.2.2}$R$^{1.3.2.3}$, —O—C(O)—R$^{1.3.2.1}$ or (c) a $C_{1-3}$-alkyl group wherein each methylene group is substituted by up to two fluorine atoms and each methyl group is substituted by up to three fluorine atoms, $R^{1.3.1.1}$ denotes
(a) H,
(b) $C_{1-6}$-alkyl, $C_{3-6}$-cycloalkyl, aryl, heteroaryl, benzyl which may be substituted by a group $R^{1.3.1.1.1}$, or
(c) a $C_{1-3}$-alkyl group wherein each methylene group is substituted by up to two fluorine atoms and each methyl group is substituted by up to three fluorine atoms, $R^{1.3.1.1.1}$ denotes halogen, HO— or $C_{1-6}$-alkyl-O—, $R^{1.3.1.2}$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^{1.3.1.3}$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$ or fluorine, wherein the substituents $R^{1.3.1.1}$ are independent of one another, $R^{1.3.2.1}$ denotes
(a) H,
(b) $C_{1-6}$-alkyl, $C_{3-6}$-cycloalkyl, aryl, heteroaryl, benzyl which may be substituted by a group $R^{1.3.2.1.1}$, or
(c) a $C_{1-3}$-alkyl group wherein each methylene group is substituted by up to two fluorine atoms and each methyl group is substituted by up to three fluorine atoms, $R^{1.3.2.1.1}$ denotes halogen, HO— or $C_{1-6}$-alkyl-O—, $R^{1.3.2.2}$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^{1.3.2.3}$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$ or fluorine, wherein the substituents $R^{1.3.2.1}$ are independent of one another, m denotes one of the numbers 0, 1 or 2 and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A third embodiment of the present invention comprises the compounds of the above general formulae Ia and Ib, wherein $R^2$, $R^3$, $R^4$ and $R^5$ are defined as hereinbefore in the first embodiment and $R^1$ denotes a group of general formulae

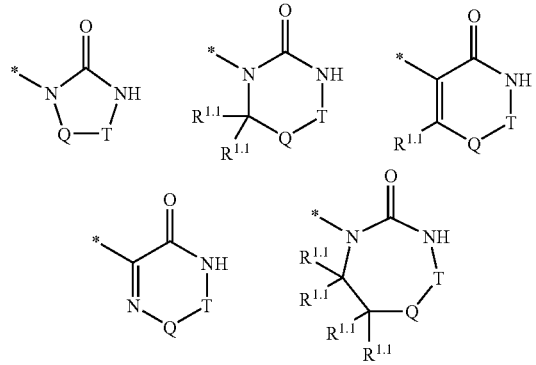

wherein
Q-T denotes $C(R^{1.3})_2$—$C(R^{1.3})_2$, $C(R^{1.3})$=$C(R^{1.3})$, N=C($R^{1.3}$), $C(R^{1.3})_2$—C(=O), C(=O)—$C(R^{1.3})_2$, $C(R^{1.3})_2$—$S(O)_m$ or $C(R^{1.3})_2$—$N(R^{1.3})$,
while in a group $C(R^{1.3})_2$—$C(R^{1.3})_2$, $C(R^{1.3})$=$C(R^{1.3})$ or $C(R^{1.3})_2$—$N(R^{1.3})$ contained in Q-T in each case a group $R^{1.3}$ together with an adjacent group $R^{1.3}$ and the atoms to which these groups are bound may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-S-oxide, thiomorpholinyl-S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another denote by 1, 2 or 3 substituents $R^{1.3.1}$, $R^{1.1}$ denotes
(a) H,
(b) $C_{1-6}$-alkyl, —CN, —OH, —O—$C_{1-3}$-alkyl,
(c) a $C_{1-3}$-alkyl- or $C_{1-3}$-alkyl-O— group wherein each methylene group is substituted by up to two fluorine atoms and each methyl group is substituted by up to three fluorine atoms, $R^{1.3}$ independently of one another denote
(a) H, $C_{1-6}$-alkyl, $C_{2-6}$-alkenyl, $C_{2-6}$-alkynyl, $C_{3-6}$-cycloalkyl,
(b) an aryl group optionally substituted by 1, 2 or 3 substituents $R^{1.3.2}$, wherein the substituents $R^{1.3.2}$ may be identical or different,
(c) a heteroaryl group optionally substituted by 1, 2 or 3 substituents $R^{1.3.2}$, wherein the substituents $R^{1.3.2}$ may be identical or different,
(d) a heterocyclic group optionally substituted by 1, 2 or 3 substituents $R^{1.3.2}$, wherein the substituents $R^{1.3.2}$ may be identical or different, $R^{1.3.1}$ denotes
- (a) H, halogen, $C_{1-6}$-alkyl, $C_{3-6}$-cycloalkyl,
- (b) —O—$R^{1.3.1.1}$, —O—$C_{1-6}$-alkylene-$NR^{1.3.1.2}R^{1.3.1.3}$, —$CO_2R^{1.3.1.1}$, —$C(O)NR^{1.3.1.2}R^{1.3.1.3}$, —$SO_2$—$NR^{1.3.1.2}R^{1.3.1.3}$, —$N(R^{1.3.1.2})$—$SO_2$—$R^{1.3.1.3}$, —$S(O)_m R^{1.3.1.2}$, —CN, —$NR^{1.3.1.2}R^{1.3.1.3}$, —O—C(O)—$R^{1.3.1.1}$ or
- (c) a $C_{1-3}$-alkyl group wherein each methylene group is substituted by up to two fluorine atoms and each methyl group is substituted by up to three fluorine atoms, $R^{1.3.2}$ denotes
- (a) halogen, $C_{1-6}$-alkyl, $C_{3-6}$-cycloalkyl,
- (b) —O—$R^{1.3.2.1}$, —O—$(CH_2)_s$—O—$R^{1.3.2.1}$, —$CO_2R^{1.3.2.1}$, —$S(O)_m$—$R^{1.3.2.2}$, —CN, —O—C(O)—$R^{1.3.2.1}$ or
- (c) a $C_{1-3}$-alkyl group wherein each methylene group is substituted by up to two fluorine atoms and each methyl group is substituted by up to three fluorine atoms, $R^{1.3.1.1}$ denotes
- (a) H,
- (b) $C_{1-6}$-alkyl, $C_{3-6}$-cycloalkyl, aryl, heteroaryl, benzyl which may be substituted by a group $R^{1.3.1.1.1}$, or
- (c) a $C_{1-3}$-alkyl group wherein each methylene group is substituted by up to two fluorine atoms and each methyl group is substituted by up to three fluorine atoms, $R^{1.3.1.1.1}$ denotes halogen, HO— or $C_{1-6}$-alkyl-O—, $R^{1.3.1.2}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, $R^{1.3.1.3}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, or $R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$, wherein the substituents $R^{1.3.1.1}$ are independent of one another, $R^{1.3.2.1}$ denotes
- (a) H,
- (b) $C_{1-6}$-alkyl, $C_{3-6}$-cycloalkyl, aryl, heteroaryl, benzyl which may be substituted by a group $R^{1.3.2.1.1}$, or
- (c) a $C_{1-3}$-alkyl group wherein each methylene group is substituted by up to two fluorine atoms and each methyl group is substituted by up to three fluorine atoms, $R^{1.3.2.1.1}$ denotes halogen, HO— or $C_{1-6}$-alkyl-O—, $R^{1.3.2.2}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, $R^{1.3.2.3}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, or $R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$, wherein the substituents $R^{1.3.2.1}$ are independent of one another, m denotes one of the numbers 0, 1 or 2 and s denotes one of the numbers 1, 2 or 3, the tautomers, the diastereomers, the enantiomers, the hydrates, the mixtures thereof and the salts thereof as well as the hydrates of the salts, particularly the physiologically acceptable salts thereof with inorganic or organic acids or bases.

A fourth embodiment of the present invention comprises the compounds of the above general formulae Ia and Ib, wherein $R^2$, $R^3$, $R^4$ and $R^5$ are defined as hereinbefore in the first embodiment and $R^1$ denotes a group of general formulae

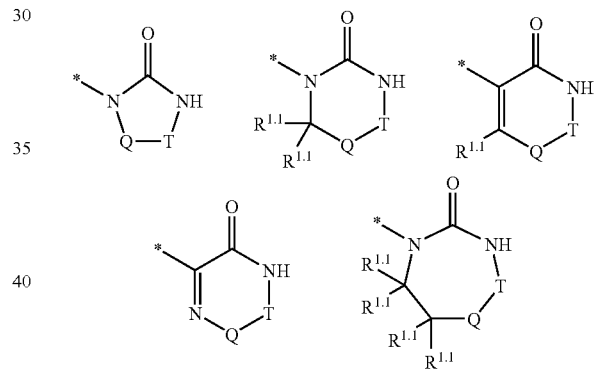

wherein

Q-T denotes $C(R^{1.3})_2$—$C(R^{1.3})_2$, $C(R^{1.3})$=$C(R^{1.3})$, N=C($R^{1.3}$), $C(R^{1.3})_2$—$C(=O)$, $C(=O)$—$C(R^{1.3})_2$, $C(R^{1.3})_2$—$S(O)_m$ or $C(R^{1.3})_2$—$N(R^{1.3})$, while in a group $C(R^{1.3})_2$—$C(R^{1.3})_2$, $C(R^{1.3})$=$C(R^{1.3})$ or $C(R^{1.3})_2$—$N(R^{1.3})$ contained in Q-T in each case a group $R^{1.3}$ together with an adjacent group $R^{1.3}$ and the atoms to which these groups are bound may also denote a group selected from cyclopentyl, cyclohexyl, cyclopentenyl, cyclohexenyl, dioxanyl, phenyl, naphthyl, thienyl, pyridyl, pyrazinyl, pyridazinyl, quinolinyl, isoquinolinyl, morpholinyl, pyrrolidinyl, piperidinyl, tetrahydrofuranyl, tetrahydropyranyl and piperazinyl, which may be substituted independently of one another denote by 1, 2 or 3 substituents $R^{1.3.1}$, $R^{1.1}$ denotes
- (a) H,
- (b) $C_{1-6}$-alkyl, —CN, —OH, —O—$C_{1-3}$-alkyl,
- (c) a $C_{1-3}$-alkyl- or $C_{1-3}$-alkyl-O— group wherein each methylene group is substituted by up to two fluorine atoms and each methyl group is substituted by up to three fluorine atoms, $R^{1.3}$ denotes
- (a) H, $C_{1-6}$-alkyl, $C_{3-6}$-cycloalkyl,
- (b) an aryl group optionally substituted by 1, 2 or 3 substituents $R^{1.3.2}$, wherein the substituents $R^{1.3.2}$ may be identical or different,
- (c) a heteroaryl group optionally substituted by 1, 2 or 3 substituents $R^{1.3.2}$, wherein the substituents $R^{1.3.2}$ may be identical or different,
- (d) a heterocyclic group optionally substituted by 1, 2 or 3 substituents $R^{1.3.2}$, wherein the substituents $R^{1.3.2}$ may be identical or different, $R^{1.3.1}$ denotes
- (a) H, halogen, $C_{1-6}$-alkyl, $C_{3-6}$-cycloalkyl,
- (b) —O—$R^{1.3.1.1}$, —O—$C_{1-6}$-alkylene-$NR^{1.3.1.2}R^{1.3.1.3}$, —$CO_2R^{1.3.1.1}$, —C(O)—$NR^{1.3.1.2}R^{1.3.1.3}$, —$SO_2$—$NR^{1.3.1.2}R^{1.3.1.3}$, —$NR^{1.3.1,2}$—$SO_2$—$R^{1.3.1.3}$, —S(O)$_m$—$R^{1.3.1.2}$, —CN, —$NR^{1.3.1.2}R^{1.3.1.3}$, —O—C(O)—$R^{1.3.1.1}$ or
- (c) a $C_{1-3}$-alkyl group wherein each methylene group is substituted by up to two fluorine atoms and each methyl group is substituted by up to three fluorine atoms, $R^{1.3.2}$ denotes
- (a) halogen, $C_{1-6}$-alkyl, $C_{3-6}$-cycloalkyl,
- (b) —O—$R^{1.3.2.1}$, —O—$(CH_2)_s$—$OR^{1.3.2.1}$, —$CO_2R^{1.3.2.1}$, —S(O)$_m$—$R^{1.3.2.2}$, —CN, —O—C(O)—$R^{1.3.2.1}$ or
- (c) a $C_{1-3}$-alkyl group wherein each methylene group is substituted by up to two fluorine atoms and each methyl group is substituted by up to three fluorine atoms, $R^{1.3.1.1}$ denotes
- (a) H,
- (b) $C_{1-6}$-alkyl, $C_{3-6}$-cycloalkyl, aryl, heteroaryl, benzyl which may be substituted by a group $R^{1.3.1.1.1}$, or
- (c) a $C_{1-3}$-alkyl group wherein each methylene group is substituted by up to two fluorine atoms and each methyl group is substituted by up to three fluorine atoms, $R^{1.3.1.1.1}$ denotes halogen, HO— or $C_{1-6}$-alkyl-O—, $R^{1.3.1.2}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, $R^{1.3.1.3}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, or $R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$, wherein the substituents $R^{1.3.1.1}$ are independent of one another, $R^{1.3.2.1}$ denotes
- (a) H,
- (b) $C_{1-6}$-alkyl, $C_{3-6}$-cycloalkyl, aryl, heteroaryl, benzyl which may be substituted by a group $R^{1.3.2.1.1}$, or
- (c) a $C_{1-3}$-alkyl group wherein each methylene group is substituted by up to two fluorine atoms and each methyl group is substituted by up to three fluorine atoms, $R^{1.3.2.1.1}$ denotes halogen, HO— or $C_{1-6}$-alkyl-O—, $R^{1.3.2.2}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, $R^{1.3.2.3}$ denotes
- (a) H,
- (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, or $R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$, wherein the substituents $R^{1.3.2.1}$ are independent of one another, m denotes one of the numbers 0, 1 or 2 and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A fifth embodiment of the present invention comprises the compounds of the above general formulae Ia and Ib, wherein $R^2$, $R^3$, $R^4$ and $R^5$ are defined as hereinbefore in the first embodiment and
$R^1$ denotes a group of general formula -continued

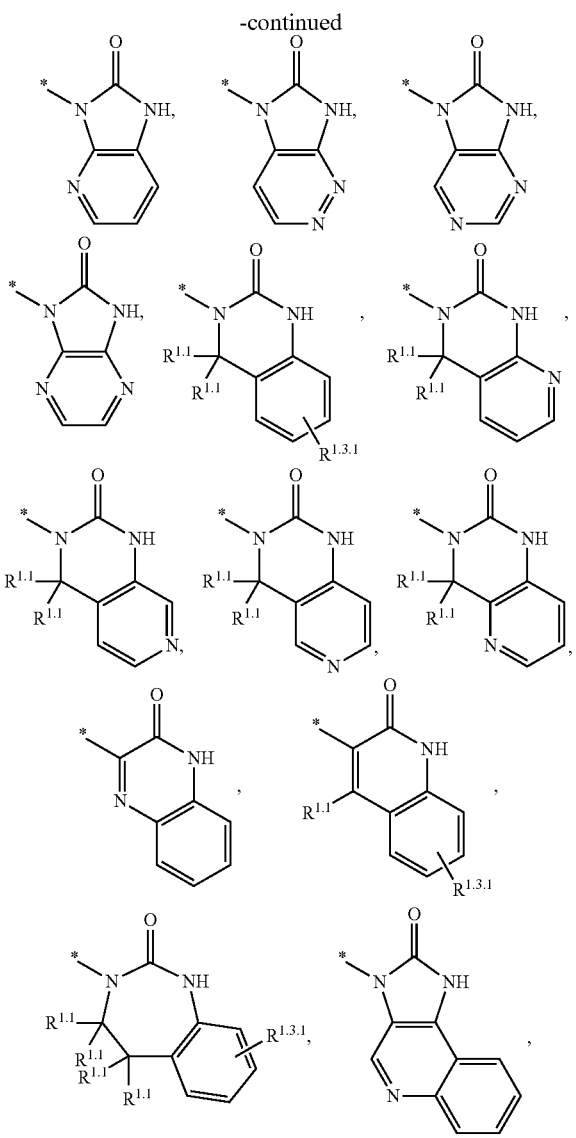

wherein
$R^{1.1}$ denotes
  (a) H,
  (b) $C_{1-3}$-alkyl, —OH, —O—$C_{1-3}$-alkyl,
  (c) a $C_{1-3}$-alkyl- or $C_{1-3}$-alkyl-O— group wherein each methylene group is substituted by up to two fluorine atoms and each methyl group is substituted by up to three fluorine atoms,
$R^{1.3}$ independently of one another denote
  (a) H, $C_{1-6}$-alkyl, $C_{3-6}$-cycloalkyl,
  (b) a phenyl group optionally substituted by 1, 2 or 3 substituents $R^{1.3.2}$, wherein the substituents $R^{1.3.2}$ may be identical or different,
  (c) a heteroaryl group optionally substituted by 1, 2 or 3 substituents $R^{1.3.2}$ which is selected from among benzimidazole, benzothiophene, furan, imidazole, indole, isoxazole, oxazole, pyrazine, pyrazole, pyridazine, pyridine, pyrimidine, pyrrole, thiazole, thiophene and triazole, wherein the substituents $R^{1.3.2}$ may be identical or different,
  (d) a heterocyclic group optionally substituted by 1, 2 or 3 substituents $R^{1.3.2}$, wherein the substituents $R^{1.3.2}$ may be identical or different, $R^{1.3.1}$ denotes
  (a) H, halogen, $C_{1-6}$-alkyl, $C_{3-6}$-cycloalkyl,
  (b) —O—$R^{1.3.1.1}$, —O—$C_{1-6}$-alkylene-$NR^{1.3.1.2}R^{1.3.1.3}$, —$CO_2R^{1.3.1.1}$, —C(O)—$NR^{1.3.1.2}R^{1.3.1.3}$, —$SO_2$—$NR^{1.3.1.2}R^{1.3.1.3}$, —$NR^{1.3.1.2}$—$SO_2$—$R^{1.3.1.3}$, —$S(O)_m$—$R^{1.3.1.2}$, —CN, —$NR^{1.3.1.2}R^{1.3.1.3}$, —O—C(O)—$R^{1.3.1.1}$ or
  (c) a $C_{1-3}$-alkyl or $C_{1-3}$-alkyl-O— group wherein each methylene group is substituted by up to two fluorine atoms and each methyl group is substituted by up to three fluorine atoms,
$R^{1.3.2}$ denotes
  (a) halogen, $C_{1-6}$-alkyl, $C_{3-6}$-cycloalkyl,
  (b) —O—$R^{1.3.2.1}$, —O—$(CH_2)_s$—O—$R^{1.3.2.1}$, —$CO_2R^{1.3.2.1}$, —$S(O)_m$—$R^{1.3.2.2}$, —CN, —O—C(O)—$R^{1.3.2.1}$ or
  (c) a $C_{1-3}$-alkyl group wherein each methylene group is substituted by up to two fluorine atoms and each methyl group is substituted by up to three fluorine atoms,
$R^{1.3.1.1}$ denotes
  (a) H,
  (b) $C_{1-6}$-alkyl, $C_{3-6}$-cycloalkyl, aryl, heteroaryl, benzyl which may be substituted by a group $R^{1.3.1.1.1}$, or
  (c) a $C_{1-3}$-alkyl group wherein each methylene group is substituted by up to two fluorine atoms and each methyl group is substituted by up to three fluorine atoms,
$R^{1.3.1.1.1}$ denotes HO— or $C_{1-6}$-alkyl-O—,
$R^{1.3.1.2}$ denotes
  (a) H,
  (b) $C_{1-3}$-alkyl, phenyl or benzyl, wherein the groups may be unsubstituted or substituted by halogen, HO— or $H_3C$—O—,
$R^{1.3.1.3}$ denotes
  (a) H,
  (b) $C_{1-3}$-alkyl, phenyl or benzyl, wherein the groups may be unsubstituted or substituted by halogen, HO— or $H_3C$—O—, or
$R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by a substituent $R^{1.3.1.1}$,
$R^{1.3.2.1}$ denotes
  (a) H,
  (b) $C_{1-6}$-alkyl, $C_{3-6}$-cycloalkyl, aryl, heteroaryl, benzyl which may be substituted by a group $R^{1.3.2.1.1}$, or
  (c) a $C_{1-3}$-alkyl group wherein each methylene group is substituted by up to two fluorine atoms and each methyl group is substituted by up to three fluorine atoms,
$R^{1.3.2.1.1}$ denotes HO— or $C_{1-6}$-alkyl-O—,
$R^{1.3.2.2}$ denotes
  (a) H,
  (b) $C_{1-3}$-alkyl, phenyl or benzyl, wherein the groups may be unsubstituted or substituted by halogen, HO— or $H_3C$—O—,
$R^{1.3.23}$ denotes
  (a) H,
  (b) $C_{1-3}$-alkyl, phenyl or benzyl, wherein the groups may be unsubstituted or substituted by halogen, HO— or $H_3C$—O—, or
$R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by a substituent $R^{1.3.2.1}$,
m denotes one of the numbers 0, 1 or 2, and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A sixth embodiment of the present invention comprises the compounds of the above general formulae Ia and Ib, wherein $R^2$, $R^3$, $R^4$ and $R^5$ are defined as hereinbefore in the first embodiment and $R^1$ denotes a group selected from

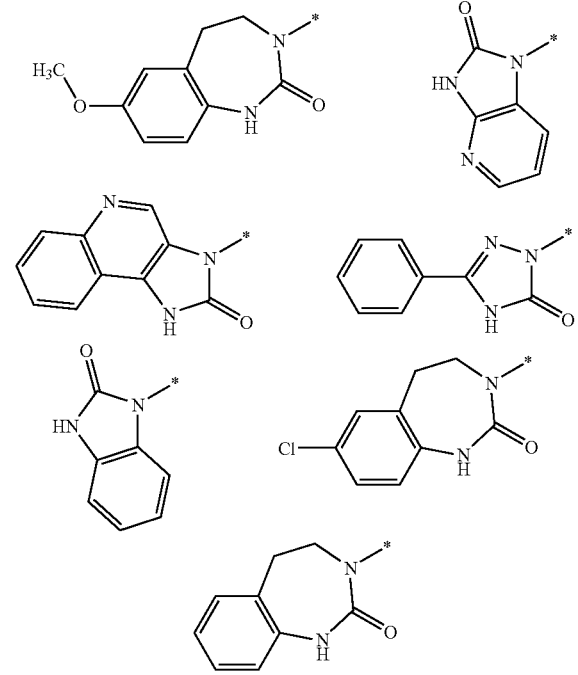

the tautomers, the diastereomers, the enantiomers, the hydrates, the mixtures thereof and the salts thereof as well as the hydrates of the salts, particularly the physiologically acceptable salts thereof with inorganic or organic acids or bases.

A seventh embodiment of the present invention comprises the compounds of the above general formulae Ia and Ib, wherein $R^1$, $R^3$, $R^4$ and $R^5$ are defined as hereinbefore in the first, second, third, fourth, fifth, sixth or seventh embodiment and $R^2$ denotes a hydrogen atom, the tautomers, the diastereomers, the enantiomers, the hydrates, the mixtures thereof and the salts thereof as well as the hydrates of the salts, particularly the physiologically acceptable salts thereof with inorganic or organic acids or bases.

An eighth embodiment of the present invention comprises the compounds of the above general formulae Ia and Ib, wherein $R^1$, $R^2$ and $R^5$ are defined as hereinbefore in the first, second, third, fourth, fifth, sixth, seventh or eighth embodiment and $R^3$ denotes
  (a) H,
  (b) $C_{1-6}$-alkyl,
  (c) a $C_{3-6}$-cycloalkyl group substituted by one or two groups $R^{3.2}$,
  (d) a $C_{1-3}$-alkyl group wherein each methylene group is substituted by up to two fluorine atoms and each methyl group is substituted by up to three fluorine atoms, $R^{3.2}$ independently of one another denote
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group wherein each methylene group is substituted by up to two fluorine atoms and each methyl group is substituted by up to three fluorine atoms, $R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) an aryl group substituted by one or two groups $R^{4.2}$,
  (f) a $C_{5-7}$-cycloalkyl group which may be fused to an aryl- or heteroaryl group, while the resultant bicyclic group is additionally substituted by one or two groups $R^{4.2}$, or
  (g) a heteroaryl group substituted by one or two groups $R^{4.2}$, $R^{4.1}$ denotes
  (a) H,
  (b) a phenyl group substituted by the groups $R^{4.1.1}$ and $R^{4.1.2}$,
  (c) a heteroaryl group substituted by the groups $R^{4.1.1}$ and $R^{4.1.2}$, $R^{4.1.1}$ denotes
  (a) H,
  (c) halogen, $C_{1-3}$-alkyl, —OH, —CN, —O—$C_{1-3}$-alkyl, —$NR^{4.1.1.1}R^{4.1.1.2}$, —S—$C_{1-3}$-alkyl, —$NR^{4.1.1.1}$—C(O)—$C_{1-3}$-alkyl, —C(O)—$NR^{4.1.1.1}R^{4.1.1.2}$, C(O)—O—$R^{4.1.1.3}$,
  (d) a $C_{1-3}$-alkyl- or —O—$C_{1-3}$-alkyl group wherein each methylene group is substituted by up to two fluorine atoms and each methyl group is substituted by up to three fluorine atoms, $R^{4.1.1.1}$ denotes H, $C_{1-3}$-alkyl,
$R^{4.1.1.2}$ denotes H, $C_{1-3}$-alkyl, or
$R^{4.1.1.1}$ and $R^{4.1.1.2}$ together with the nitrogen atom to which they are bound also denote a group selected from morpholinyl, thiomorpholinyl, piperidinyl, piperazinyl, pyrrolidinyl and azetidinyl, $R^{4.1.1.3}$ denotes H, $C_{1-3}$-alkyl,
$R^{4.1.2}$ denotes
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ independently of one another denote
  (a) H,
  (b) halogen, $C_{1-3}$-alkyl, —OH, —CN, —O—$C_{1-3}$-alkyl, —$NR^{4.2.1}R^{4.2.2}$, —S—$C_{1-6}$-alkyl, —$NR^{4.2.1}$—C(O)—$C_{1-3}$-alkyl, —C(O)—$NR^{4.2.1}R^{4.2.2}$, —C(O)—O—$R^{4.2.3}$,
  (c) a $C_{1-3}$-alkyl- or —O—$C_{1-3}$-alkyl group wherein each methylene group is substituted by up to two fluorine atoms and each methyl group is substituted by up to three fluorine atoms, $R^{4.2.1}$ denotes H, $C_{1-3}$-alkyl and
$R^{4.2.2}$ denotes H, $C_{1-3}$-alkyl, or
$R^{4.2.1}$ and $R^{4.2.2}$ together with the nitrogen atom to which they are bound also denote a group which is selected from among morpholinyl, thiomorpholinyl, piperidinyl, piperidonyl, piperazinyl, pyrrolidinyl and azetidinyl, and which may additionally be substituted by one or two groups selected from F, —OH, —O—$C_{1-3}$-alkyl, —OCF$_3$, $C_{1-3}$-alkyl and CF$_3$, $R^{4.2.3}$ denotes H, $C_{1-3}$-alkyl, $R^3$ and $R^4$ together with the nitrogen atom to which they are bound denote:
  (a) a saturated 5-, 6- or 7-membered heterocyclic group which is substituted at a carbon atom by a group $R^{4.3}$ or by two groups $R^{4.3}$ and $R^{4.4}$,
  (b) a saturated 5-, 6- or 7-membered heterocyclic group which is substituted at two adjacent carbon atoms by in each case a group $R^{4.3}$ and $R^{4.4}$,
  (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
  (d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
  (e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or
  (f) a heteroaryl group which is substituted at 1, 2 or 3 carbon atoms by a group $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN $R^{4.3.1}$ denotes H, $C_{1-3}$-alkyl-O—C(O)—, —NH$_2$, ($C_{1-4}$-alkyl)-NH—, ($C_{1-4}$-alkyl)$_2$N—, heterocyclyl, $R^{4.4}$ denotes
  (a) H, $C_{1-3}$-alkyl, —OH, —O—$C_{1-3}$-alkyl or
  (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl, $C_{5-6}$-cycloalkenyl or heterocyclyl group, $R^{4.5}$ independently of one another denote
  (a) H,
  (b) halogen, $C_{1-3}$-alkyl, —OH, —O—$C_{1-3}$-alkyl, —NH$_2$, —CN, —C(O)—O—$R^{4.5.1}$, —C(O)—NR$^{4.5.2}$R$^{4.5.3}$,
  (c) a $C_{1-3}$-alkyl- or —O—$C_{1-3}$-alkyl group wherein each methylene group is substituted by up to two fluorine atoms and each methyl group is substituted by up to three fluorine atoms,
  (d) phenyl, $R^{4.5.1}$ denotes H, $C_{1-3}$-alkyl,
$R^{4.5.2}$ denotes H, $C_{1-3}$-alkyl and
$R^{4.5.3}$ denotes H, $C_{1-3}$-alkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A ninth embodiment of the present invention comprises the compounds of the above general formulae Ia and Ib, wherein $R^1$, $R^2$ and $R^5$ are defined as hereinbefore in the first, second, third, fourth, fifth, sixth, seventh or eighth embodiment and $R^3$ denotes
  (a) H,
  (b) $C_{1-6}$-alkyl,
  (c) a $C_{3-6}$-cycloalkyl substituted by one or two groups $R^{3.2}$, or
  (d) a $C_{1-3}$-alkyl group wherein each methylene group is substituted by up to two fluorine atoms and each methyl group is substituted by up to three fluorine atoms, $R^{3.2}$ independently of one another denote
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group wherein each methylene group is substituted by up to two fluorine atoms and each methyl group is substituted by up to three fluorine atoms, $R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) an aryl group substituted by one or two groups $R^{4.2}$,
  (f) a $C_{5-6}$-cycloalkyl group which may be fused to a phenyl, thiazole or thienyl group, while the resultant bicyclic group is additionally substituted by one or two groups $R^{4.2}$, $R^{4.1}$ denotes
  (a) H,
  (b) a phenyl group substituted by the groups $R^{4.1.1}$ and $R^{4.1.2}$, $R^{4.1.1}$ denotes
  (a) H,
  (b) halogen, $C_{1-3}$-alkyl, —OH, —O—$C_{1-3}$-alkyl, —CN, —C(O)—O—$R^{4.1.1.3}$,
  (c) a $C_{1-3}$-alkyl- or —O—$C_{1-3}$-alkyl group wherein each methylene group is substituted by up to two fluorine atoms and each methyl group is substituted by up to three fluorine atoms, $R^{4.1.1.3}$ denotes H, $C_{1-3}$-alkyl, $R^{4.1.2}$ denotes
  (a) H,
  (b) halogen, $C_{1-3}$-alkyl, —OH, —O—$C_{1-3}$-alkyl,
  (c) a $C_{1-3}$-alkyl or —O—$C_{1-3}$-alkyl group wherein each methylene group is substituted by up to two fluorine atoms and each methyl group is substituted by up to three fluorine atoms, or $R^{4.2}$ independently of one another denote
  (a) H,
  (b) halogen, $C_{1-3}$-alkyl, —OH, —O—$C_{1-3}$-alkyl, —CN, —NH$_2$, —O—C(O)—$C_{1-3}$-alkyl,
  (c) a $C_{1-3}$-alkyl or —O—$C_{1-3}$-alkyl group wherein each methylene group is substituted by up to two fluorine atoms and each methyl group is substituted by up to three fluorine atoms, $R^3$ and $R^4$ together with the nitrogen atom to which they are bound denote:
  (a) a saturated 5- or 6-membered heterocyclic group which is substituted at a carbon atom by a group $R^{4.3}$ or by two groups $R^{4.3}$ and $R^{4.4}$,
  (b) a saturated 5- or 6-membered heterocyclic group which is substituted at two adjacent carbon atoms by in each case a group $R^{4.3}$ and $R^{4.4}$,
  (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
(d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
(e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$ and is selected from among

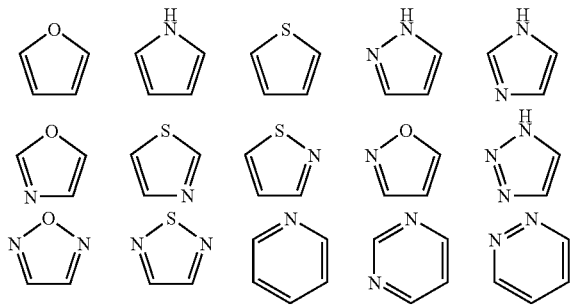

(f) a heteroaryl group which is substituted at 1, 2 or 3 carbon atoms by in each case a group $R^{4.5}$,
$R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN
$R^{4.3.1}$ denotes H, $C_{1-3}$-alkyl-O—C(O)—, —NH$_2$, ($C_{1-4}$-alkyl)-NH—, ($C_{1-4}$-alkyl)$_2$N—, morpholinyl, thiomorpholinyl, piperidinyl, pyrrolidinyl, azetidinyl,
$R^{4.4}$ denotes
(a) H, $C_{1-3}$-alkyl, —OH, —O—$C_{1-3}$-alkyl or
(b) a $C_{1-3}$-alkyl- or —O—$C_{1-3}$-alkyl group wherein each methylene group is substituted by up to two fluorine atoms and each methyl group is substituted by up to three fluorine atoms,
$R^{4.3}$ and $R^{4.4}$ together with the carbon atoms to which they are bound also denote a $C_{3-6}$-cycloalkyl or heterocyclyl group, and
$R^{4.5}$ independently of one another denote
(a) H,
(b) halogen, $C_{1-3}$-alkyl, —OH, —O—$C_{1-3}$-alkyl, —NH$_2$, —CN,
(c) a $C_{1-3}$-alkyl- or —O—$C_{1-3}$-alkyl group wherein each methylene group is substituted by up to two fluorine atoms and each methyl group is substituted by up to three fluorine atoms, or
(d) phenyl,
the tautomers, the diastereomers, the enantiomers, the hydrates, the mixtures thereof and the salts thereof as well as the hydrates of the salts, particularly the physiologically acceptable salts thereof with inorganic or organic acids or bases.

A tenth embodiment of the present invention comprises the compounds of the above general formulae Ia and Ib, wherein $R^1$, $R^2$ and $R^5$ are defined as hereinbefore in the first, second, third, fourth, fifth, sixth, seventh or eighth embodiment and $R^3$ denotes
(a) H,
(b) $C_{1-6}$-alkyl,
(c) a $C_{3-6}$-cycloalkyl group substituted by one or two groups $R^{3.2}$, or
(d) a $C_{1-3}$-alkyl group wherein each methylene group is substituted by up to two fluorine atoms and each methyl group is substituted by up to three fluorine atoms,
$R^{3.2}$ independently of one another denote
(a) H,
(b) halogen, $C_{1-3}$-alkyl, —OH, —O—$C_{1-3}$-alkyl,
(c) a $C_{1-3}$-alkyl- or —O—$C_{1-3}$-alkyl group wherein each methylene group is substituted by up to two fluorine atoms and each methyl group is substituted by up to three fluorine atoms,
$R^4$ denotes
(a) H,
(b) $C_{1-6}$-alkylene-$R^{4.1}$,
(c) a $C_{3-6}$-cycloalkyl group substituted by one or two groups $R^{4.2}$,
(d) a $C_{5-7}$-cycloalkenyl group substituted by one or two groups $R^{4.2}$,
(e) a phenyl group substituted by one or two groups $R^{4.2}$,
(f) a $C_{5-6}$-cycloalkyl group which may be fused to a phenyl, thiazolyl or thienyl group, while the resultant bicyclic group is additionally substituted by one or two groups $R^{4.2}$,
$R^{4.1}$ denotes
(a) H,
(b) a phenyl group substituted by the groups $R^{4.1.1}$ and $R^{4.1.2}$,
$R^{4.1.1}$ denotes
(a) H,
(b) halogen, $C_{1-3}$-alkyl, —OH, —O—$C_{1-3}$-alkyl, —CN, —C(O)—O—$R^{4.1.13}$,
(c) a $C_{1-3}$-alkyl- or —O—$C_{1-3}$-alkyl group wherein each methylene group is substituted by up to two fluorine atoms and each methyl group is substituted by up to three fluorine atoms,
$R^{4.1.1.3}$ denotes H, $C_{1-3}$-alkyl,
$R^{4.1.2}$ denotes
(a) H,
(b) halogen, $C_{1-3}$-alkyl, —OH, —O—$C_{1-3}$-alkyl,
(c) a $C_{1-3}$-alkyl or —O—$C_{1-3}$-alkyl group wherein each methylene group is substituted by up to two fluorine atoms and each methyl group is substituted by up to three fluorine atoms, or
$R^{4.2}$ denotes
(a) H,
(b) halogen, $C_{1-3}$-alkyl, —OH, —O—$C_{1-3}$-alkyl, —CN, —NH$_2$,
(c) a $C_{1-3}$-alkyl- or —O—$C_{1-3}$-alkyl group wherein each methylene group is substituted by up to two fluorine atoms and each methyl group is substituted by up to three fluorine atoms, or
$R^3$ and $R^4$ together with the nitrogen atom to which they are bound denote:
(a) a saturated 5- or 6-membered heterocyclic group which is selected from among piperidinyl, piperidinonyl, morpholinyl, thiomorpholinyl, piperazinyl, pyrrolidinyl and pyrrolidinonyl, and which is substituted at a carbon atom by a group $R^{4.3}$ or by two groups $R^{4.3}$ and $R^{4.4}$,
(b) a saturated 5- or 6-membered heterocyclic group which is selected from among piperidinyl, piperidinonyl, morpholinyl, thiomorpholinyl, piperazinyl, pyrrolidinyl and pyrrolidinonyl, and which is substituted at two adjacent carbon atoms by in each case a group $R^{4.3}$ and $R^{4.4}$,
(c) a saturated 5-, 6- or 7-membered heterocyclic group which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, and which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, while the fused-on cycloalkyl or heterocyclyl group is substituted by 1, 2 or 3 groups $R^{4.5}$, (d) a monounsaturated 5-, 6- or 7-membered heterocyclic group which is selected from among

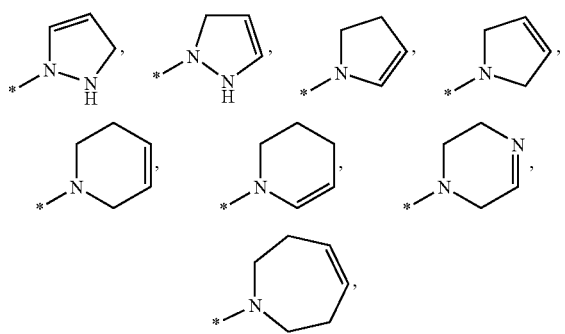

and which is substituted at a carbon atom by a group $R^{4.3}$ or by two groups $R^{4.3}$ and $R^{4.4}$ and is additionally fused to a phenyl group, the fused-on phenyl group being substituted by 1, 2 or 3 groups $R^{4.5}$, (e) a monounsaturated 5-, 6- or 7-membered heterocyclic group which is selected from among

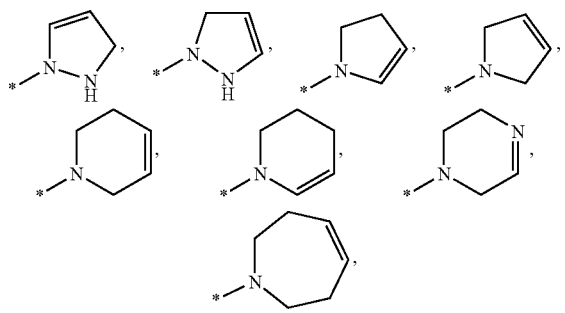

and which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, and is selected from among

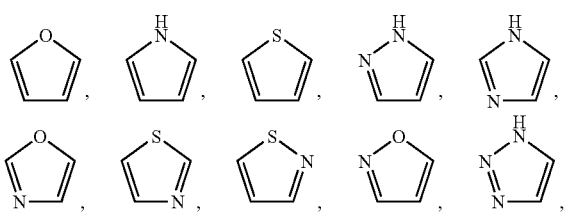

-continued

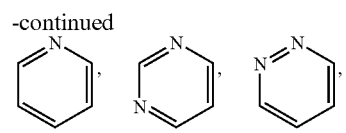

(f) a heteroaryl group which is selected from among indole, isoindole, azaindole, indazole and benzimidazole, and which is substituted at 1, 2 or 3 carbon atoms by a group $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, $R^{4.3.1}$ denotes H, $C_{1-3}$-alkyl-O—C(O), —$NH_2$, ($C_{1-4}$-alkyl)-NH, ($C_{1-4}$-alkyl)$_2$N, morpholinyl, thiomorpholinyl, piperidinyl, pyrrolidinyl, azetidinyl, $R^{4.4}$ denotes (a) H, $C_{1-3}$-alkyl, —OH, —O—$C_{1-3}$-alkyl or (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl group or a heterocyclyl group which is selected from among azetidinyl, pyrrolidinyl, piperidinyl and azepanyl, and $R^{4.5}$ independently of one another denote (a) H, (b) halogen, $C_{1-3}$-alkyl, —OH, —O—$C_{1-3}$-alkyl, —$NH_2$, —CN, (c) a $C_{1-3}$-alkyl- or —O—$C_{1-3}$-alkyl group wherein each methylene group is substituted by up to two fluorine atoms and each methyl group is substituted by up to three fluorine atoms, or (d) phenyl, the tautomers, the diastereomers, the enantiomers, the hydrates, the mixtures thereof and the salts thereof as well as the hydrates of the salts, particularly the physiologically acceptable salts thereof with inorganic or organic acids or bases.

An eleventh embodiment of the present invention comprises the compounds of the above general formulae Ia and Ib, wherein $R^1$, $R^2$ and $R^5$ are defined as hereinbefore in the first, second, third, fourth, fifth, sixth, seventh or eighth embodiment and $R^3$ denotes (a) H, (b) $C_{1-3}$-alkyl, (c) a $C_{1-3}$-alkyl group wherein each methylene group is substituted by up to two fluorine atoms and each methyl group is substituted by up to three fluorine atoms, and $R^4$ denotes H or a group selected from

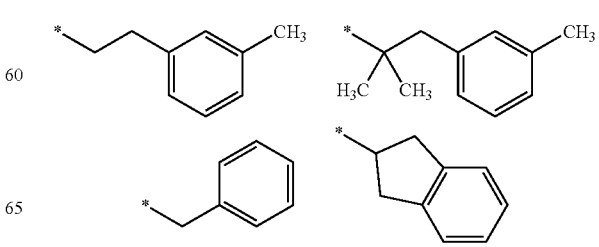

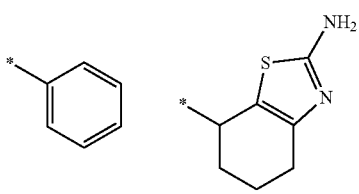
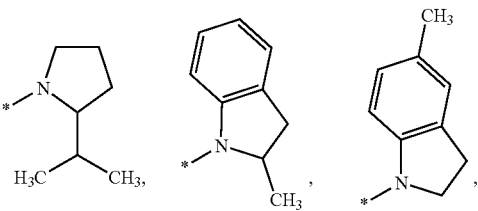
$R^3$ and $R^4$ together with the nitrogen atom to which they are bound denote a group selected from
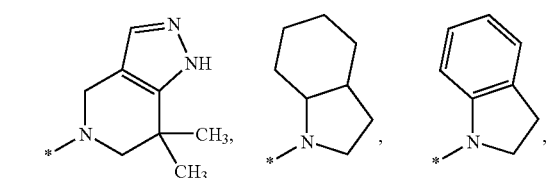
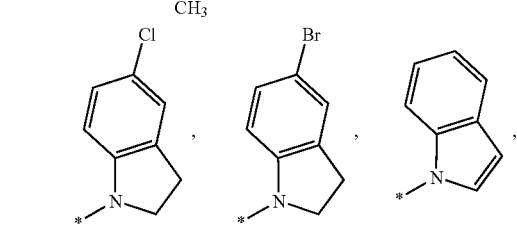
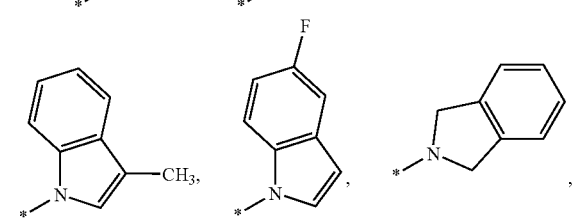
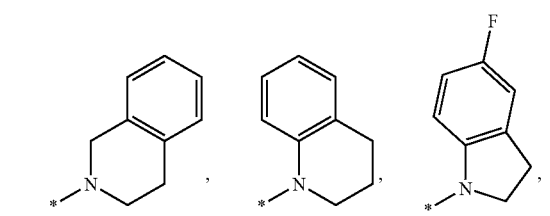
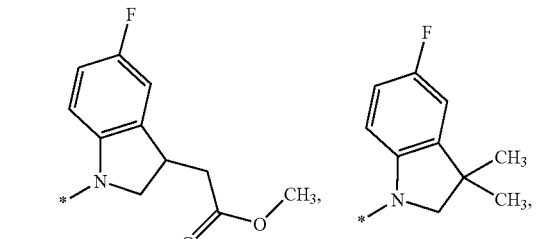
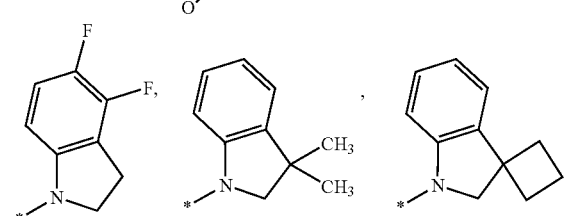
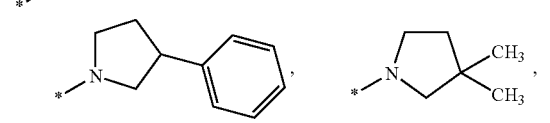
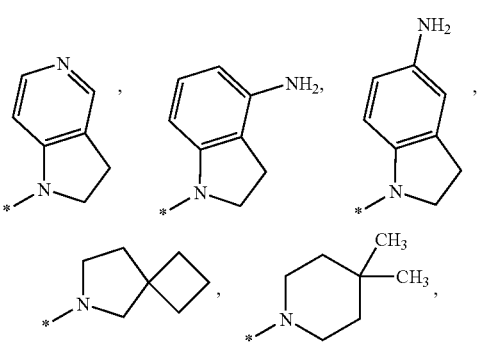
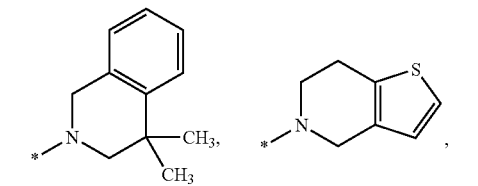
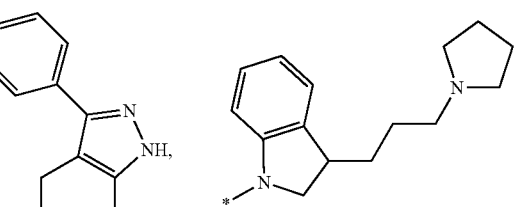
the tautomers, the diastereomers, the enantiomers, the hydrates, the mixtures thereof and the salts thereof as well as the hydrates of the salts, particularly the physiologically acceptable salts thereof with inorganic or organic acids or bases.

A twelfth embodiment of the present invention comprises the compounds of the above general formulae Ia and Ib, wherein $R^1$, $R^2$, $R^3$ and $R^4$ are defined as hereinbefore in the first, second, third, fourth, fifth, sixth, seventh, eighth, ninth, tenth or eleventh embodiment and $R^5$ denotes H or $C_{1-3}$-alkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A thirteenth embodiment of the present invention comprises the compounds of general formulae Ia and Ib wherein $R^1$ denotes a group selected from

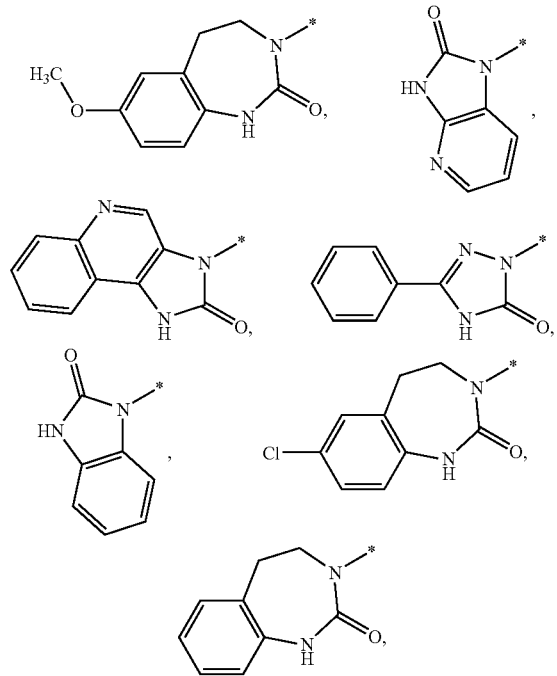

$R^2$ denotes H,
$R^3$ denotes
  (a) H,
  (b) $C_{1-3}$-alkyl,
  (c) a $C_{1-3}$-alkyl group wherein each methylene group is substituted by up to two fluorine atoms and each methyl group is substituted by up to three fluorine atoms, and
$R^4$ denotes H or a group selected from

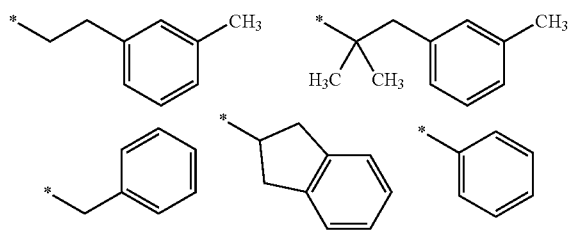

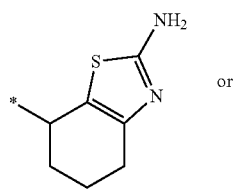

or $R^3$ and $R^4$ together with the nitrogen atom to which they are bound denote a group selected from

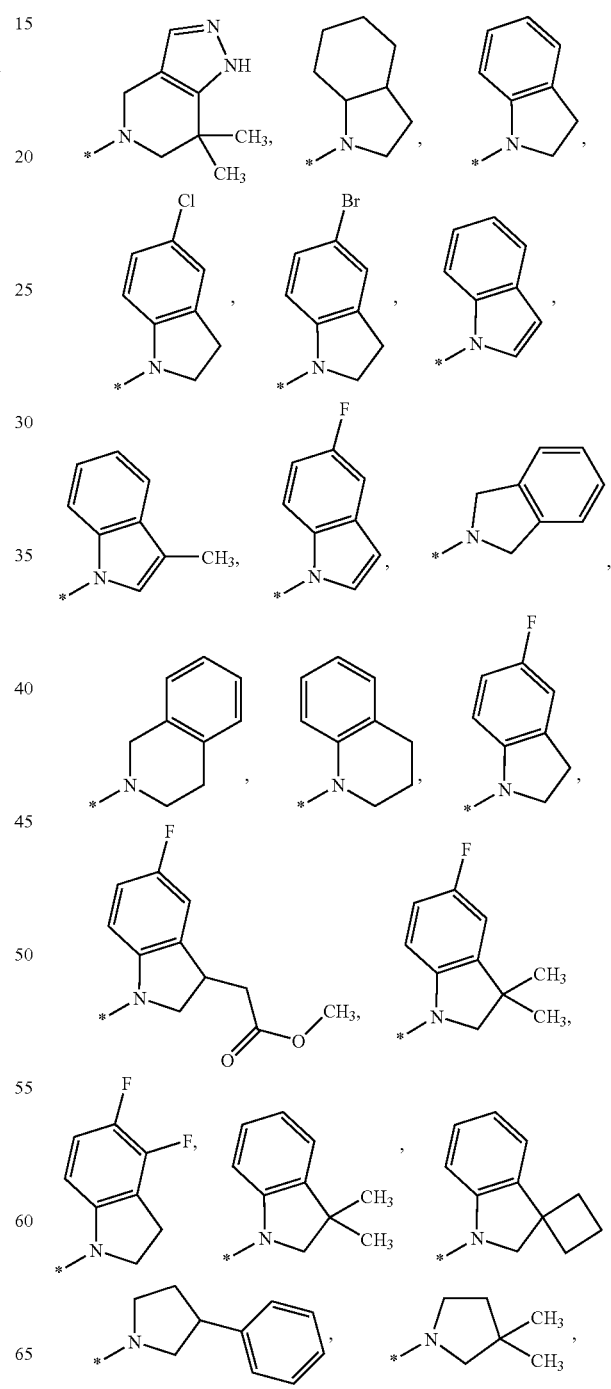

-continued

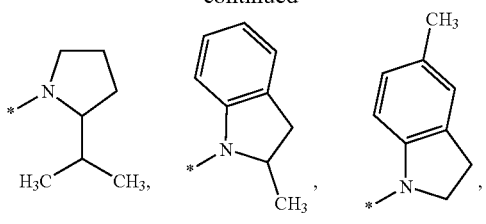

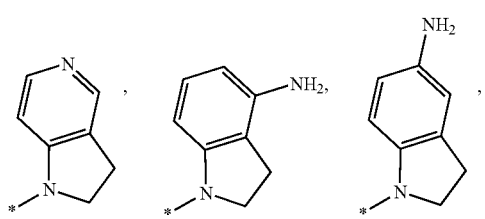

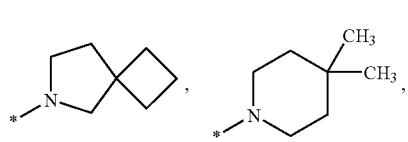

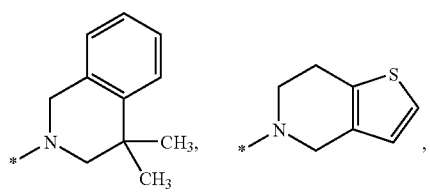

-continued

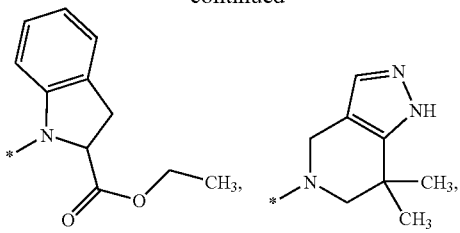

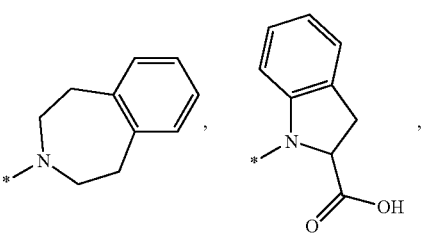

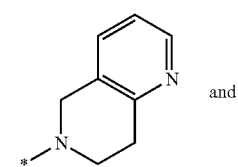

and $R^5$ denotes H or $C_{1-3}$-alkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

The following compounds are mentioned as examples of most particularly preferred compounds of the above general formulae Ia and Ib:

| No. | Structure |
|---|---|
| (1) | 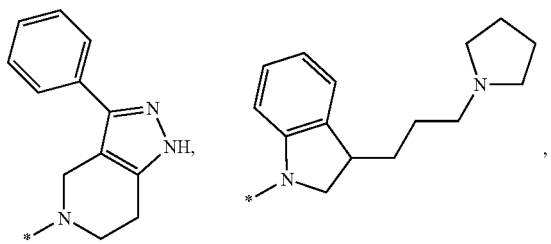 |

-continued
| No. | Structure |
|---|---|
| (2) | 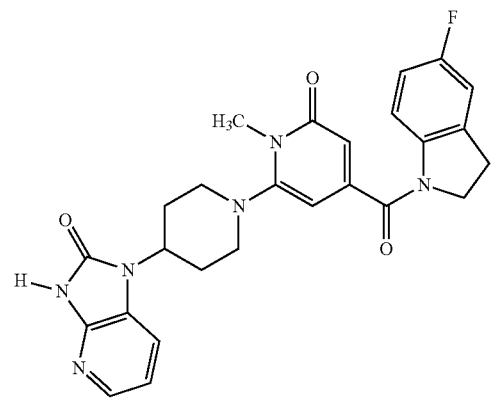 |
| (3) | 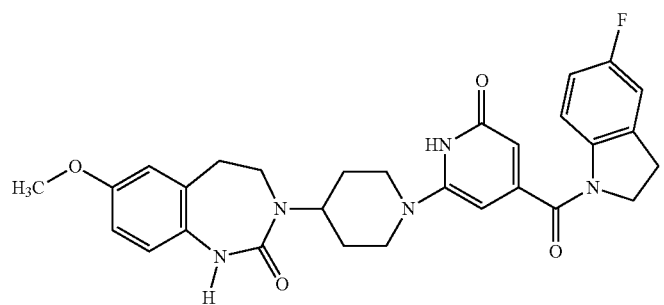 |
| (4) | 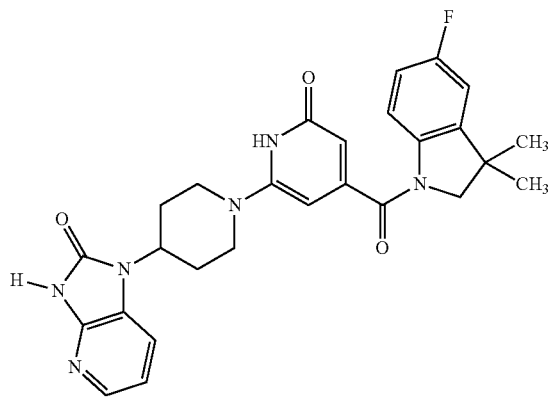 |
| (5) | 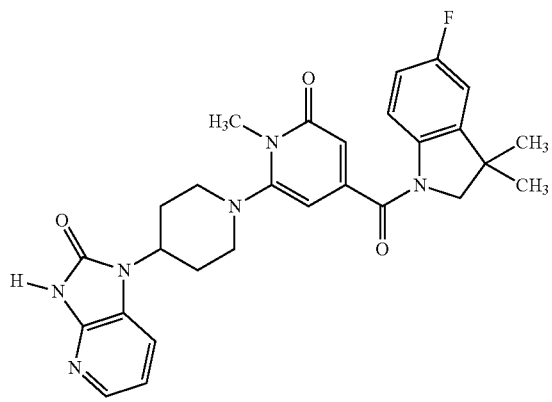 |

-continued
| No. | Structure |
|---|---|
| (6) | 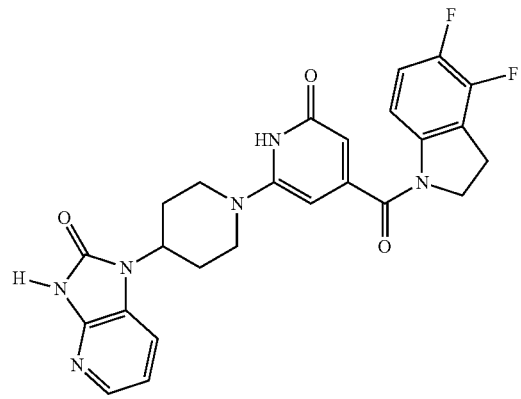 |
| (7) | 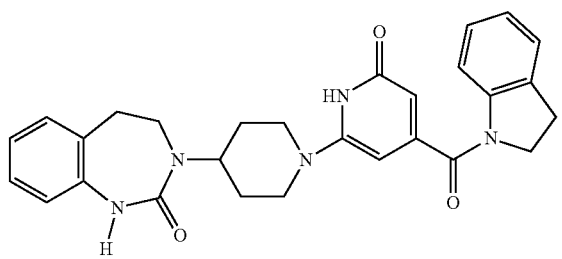 |
| (8) | 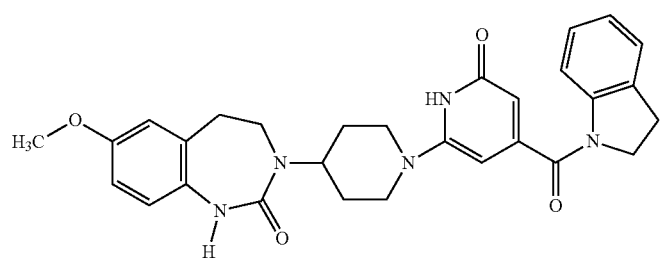 |
| (9) | 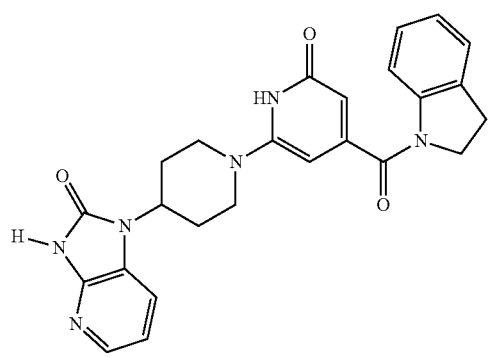 |

-continued
| No. | Structure |
|---|---|
| (10) | 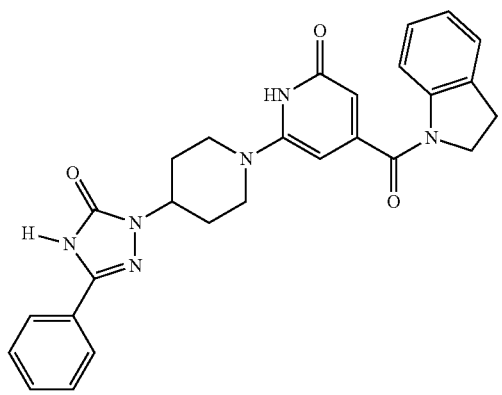 |
| (11) | 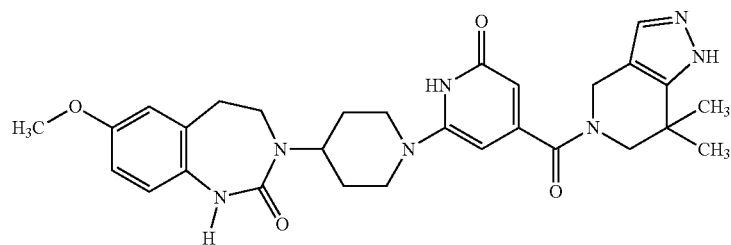 |
| (12) | 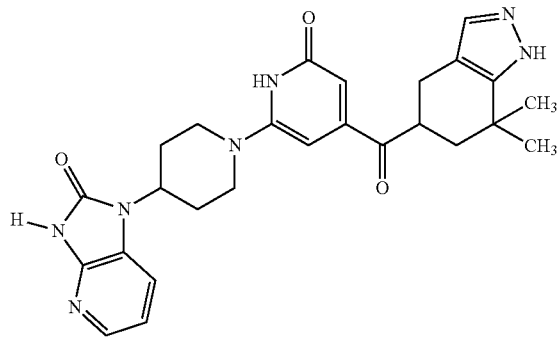 |
| (13) | 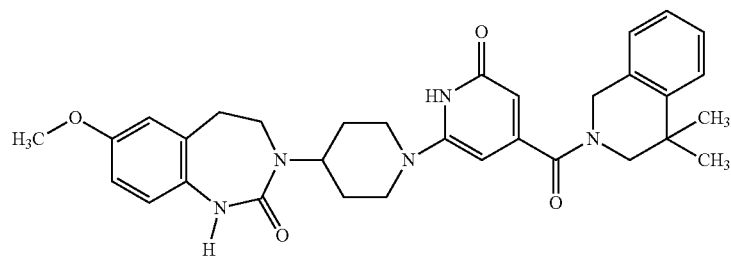 |
| (14) | 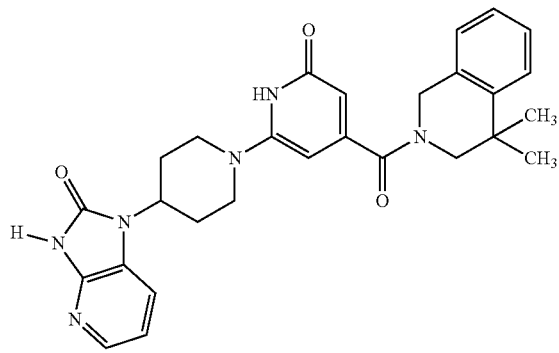 |

| No. | Structure |
|---|---|
| (15) | 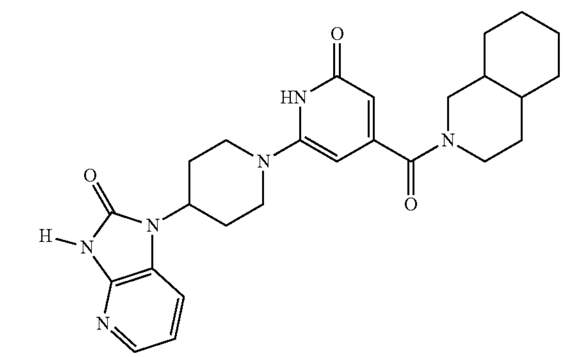 |
| (16) | 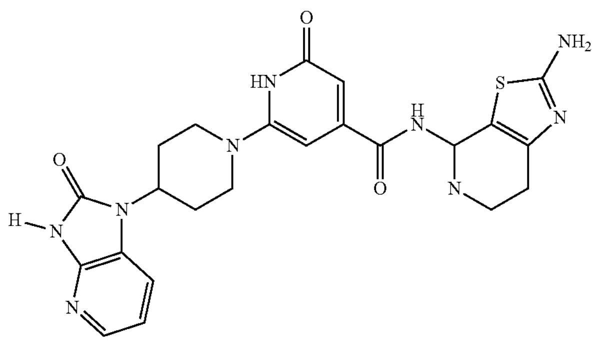 |
| (17) | | the enantiomers, the diastereomers, the hydrates, the mixtures thereof and the salts thereof as well as the hydrates of the salts, particularly the physiologically acceptable salts thereof with inorganic or organic acids or bases.

TERMS AND DEFINITIONS USED

The present specification of the invention is to be interpreted in accordance with the conventions and rules of chemical bonds.

The compounds included in this invention are those that are also chemically stable.

Unless otherwise stated, all the substituents are independent of one another. If for example there are a plurality of $C_{1-4}$-alkyl groups as substituents in one group, in the case of three $C_{1-4}$-alkyl substituents, independently of one another, one may represent methyl, one ethyl and one n-propyl.

Within the scope of this application, in the definition of possible substituents, these may also be represented in the form of a structural formula. If present, an asterisk (*) in the structural formula of the substituent is to be understood as being the linking point to the rest of the molecule. For example a phenyl group is shown as follows:

Moreover, the atom of the substituent that follows the linking point is understood as being the atom at position number 1.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are a part of other groups) are meant branched and unbranched alkyl groups with 1 to 3 carbon atoms, by the term "$C_{1-4}$-alkyl" are meant branched and unbranched alkyl groups with 1 to 4 carbon atoms and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, pentyl, neopentyl or n-hexyl. The abbreviations may optionally also be used for the above-mentioned groups Me, Et, n-Pr, i-Pr, n-Bu, i-Bu, t-Bu, etc. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are a part of other groups) are meant branched and unbranched alkylene groups with 1 to 6 carbon atoms and by the term "$C_{1-3}$-alkylene" are meant branched and unbranched alkylene groups with 1 to 3 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definition propylene includes all the possible isomeric forms of the groups in question with the same number of carbons. Thus, for example, propyl also includes 1-methylethylene and butylene includes 1-methylpropylene, 1,1-dimethylethylene, 1,2-dimethylethylene.

The definition for $C_0$-alkylene denotes a bond.

By the term "$C_{2-6}$-alkenyl" (including those which are a part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they comprise at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are a part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they comprise at least one triple bond. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example propynyl includes 1-propynyl and 2-propynyl, butynyl includes 1-, 2- and 3-butynyl, 1-methyl-1-propynyl, 1-methyl-2-propynyl etc.

By the term "$C_{3-6}$-cycloalkyl" (including those which are a part of other groups) are meant cyclic alkyl groups with 3 to 6 carbon atoms and by the term "$C_{5-6}$-cycloalkyl" are meant cyclic alkyl groups with 5 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{5-6}$-cycloalkenyl" (including those which are a part of other groups) are meant cyclic alkenyl groups with 5 or 6 carbon atoms, which contain an unsaturated bond. Examples include: cyclopentenyl or cyclohexenyl. Unless otherwise stated, the cyclic alkenyl groups may be substituted by one or more groups selected from among methyl, ethyl, iso-propyl, tert-butyl, hydroxy, fluorine, chlorine, bromine and iodine.

By the term "heterocyclyl" or "heterocyclic group" are meant, unless otherwise described in the definitions, stable 5-, 6- or 7-membered monocyclic or 8-, 9-, 10- or 11-membered bicyclic heterocyclic ring systems, which do not form an aromatic ring system in at least one ring and in addition to carbon atoms may carry one to four heteroatoms selected from among nitrogen, oxygen and sulphur. The two nitrogen atoms and also sulphur atoms may optionally be oxidised and nitrogen atoms may be quaternised. The heterocyclic ring may contain one or two carbonyl, thiocarbonyl or cyanoimino groups adjacent to a nitrogen atom. The heterocycles mentioned previously may be linked to the rest of the molecule via a carbon atom or a nitrogen atom.

Unless otherwise stated, the heterocycles may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, COO—$C_{1-3}$-alkyl, preferably CO—O-methyl or CO—O-ethyl,
while the groups may be identical or different.

The following compounds are mentioned by way of example, but the invention is not restricted to them: azetidine, oxetane, thietane, thietane dioxide, tetrahydrofuran, dihydrofuran, dioxolane, imidazolidine, imidazoline, imidazolidinone, dihydroimidazolone, oxazoline, oxazolidine, oxazolidinone, pyrrolidinone, dihydropyrazole, pyrrolidine, pyrroline, morpholine, tetrahydropyridine, dihydropyran, tetrahydropyran, dioxane, piperazine, piperidine, piperazinone, piperidinone, pyran, thiomorpholine-S-oxide, thiomorpholine-S-dioxide, thiomorpholine, dihydroxazine, morpholinedione, morpholinethione, perhydrothiazinedioxide, ε-caprolactam, oxazepanone, diazepanone, thiazepanone, perhydroazepine, dihydroquinazolinone, dihydroindole, dihydroisoindole, benzoxazolone, benzimidazolone, chromanone, tetrahydroquinoline, tetrahydrobenzoxazole, tetrahydrobenzisoxazole, tetrahydrobenzothiophene, tetrahydrothieno-pyridine, tetrahydrobenzofuran, tetrahydrooxazolopyridine, tetrahydro-isoxazolopyridine.

The following heterocycles are preferred according to the invention:

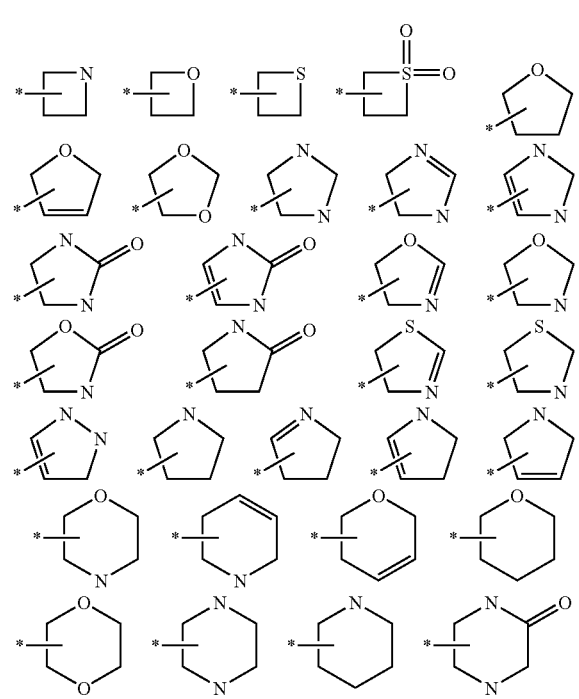

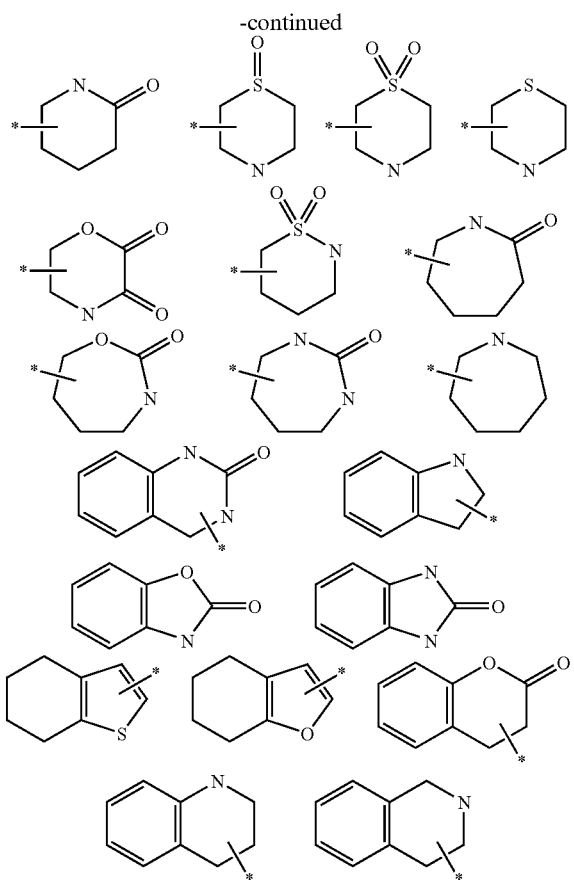

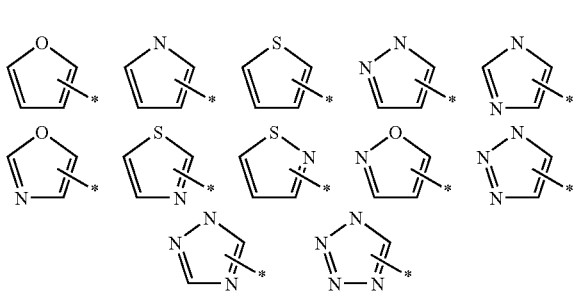

The following six-membered heterocyclic aromatic groups are preferred according to the invention:

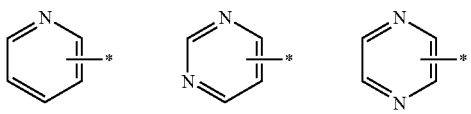

Examples of 9- or 10-membered bicyclic heteroaryl rings are as follows, but the invention is not restricted to these: indole, isoindole, indazole, indolizine, benzofuran, benzthiophene, benzimidazole, benzoxazole, benzothiazole, benzotriazole, benzisoxazole, benzisothiazole, quinoline, isoquinoline, cinnoline, phthalazine, quinoxaline, quinazoline, pyridopyrimidine, pyridopyrazine, pyridopyridazine, pyrimidopyrimidine, pteridine, purine, quinolizine, benzoxazolecarbonitrile, quinoline, isoquinolizine, quinolizine, pteridine, purine, quinolizine, benzoxazole-carbonitrile.

The following bicyclic heteroaryl rings are preferred according to this invention:

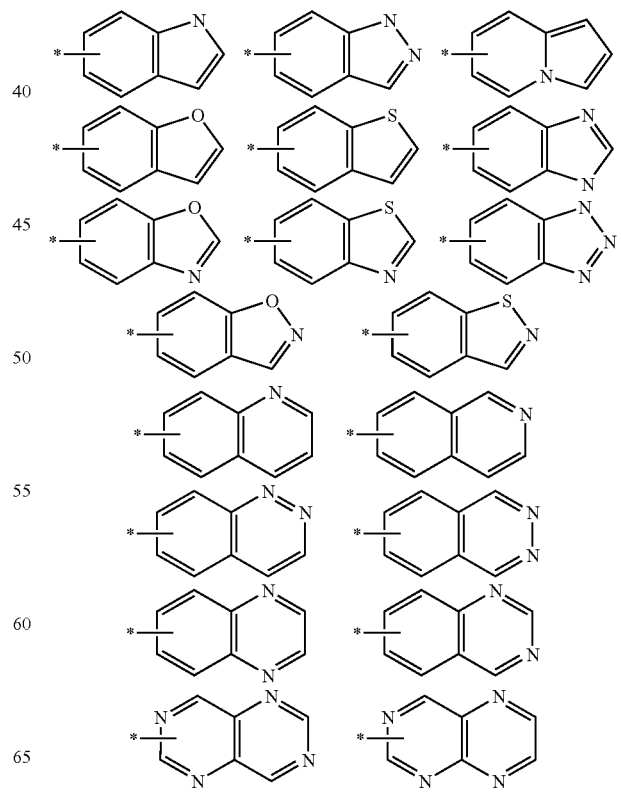

By the term "aryl" (including those which are a part of other groups) are meant monocyclic aromatic ring systems with 6 carbon atoms or bicyclic aromatic ring systems with 10 carbon atoms. Examples include phenyl, 1-naphthyl or 2-naphthyl; the preferred aryl group is phenyl.

Unless otherwise stated, the aromatic groups may be substituted by one or more groups selected from among:

(a) OH, $NO_2$, CN, $OCF_3$, $OCHF_2$, $OCH_2F$, $NH_2$, (b) halogen, preferably fluorine or chlorine, (c) $C_{1-6}$-alkyl, preferably $C_{1-3}$-alkyl, particularly preferably ethyl, methyl, iso-propyl or tert-butyl, (d) —$SO_2$—O—$C_{1-3}$-alkyl, preferably —O-methyl, (e) —O—$C_{1-3}$-alkyl, preferably —O-methyl or —O-ethyl, (f) COOH, CO—O—$C_{1-3}$-alkyl, preferably CO—O-methyl or CO—O-ethyl, while the groups may be identical or different.

By the term "heteroaryl" are meant stable five- or six-membered heterocyclic aromatic groups or 8- to 10-membered bicyclic heteroaryl rings that may contain in each ring one, two or three heteroatoms, selected from among oxygen, sulphur and nitrogen, and additionally sufficient conjugated double bonds to form an aromatic system. Examples of five- or six-membered heterocyclic aromatic groups are as follows, but the invention is not restricted to these:

furan, pyrrole, thiophene, pyrazole, imidazole, oxazole, thiazole, isothiazole, isoxazole, oxadiazole, triazole, tetrazole, furazan, thiadiazole, pyridine, pyrimidine, pyrazine, pyridazine, triazine.

The following five-membered heterocyclic aromatic groups are preferred according to the invention:

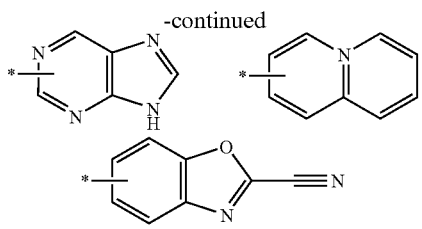

Unless otherwise stated, the heteroaryls previously mentioned may be substituted by one or more groups selected from among:
(a) OH, NO$_2$, CN, OCF$_3$, OCHF$_2$, OCH$_2$F, NH$_2$,
(b) halogen, preferably fluorine or chlorine,
(c) C$_{1-6}$-alkyl, preferably C$_{1-3}$-alkyl, particularly preferably ethyl, methyl, iso-propyl or tert-butyl,
(d) —SO$_2$—O—C$_{1-3}$-alkyl, preferably —O-methyl,
(e) —O—C$_{1-3}$-alkyl, preferably —O-methyl or —O-ethyl,
(f) COOH, CO—O—C$_{1-3}$-alkyl, preferably CO—O-methyl or CO—O-ethyl, while the groups may be identical or different.

Bicyclic heteroaryl rings may preferably be substituted in the phenyl group.

By the term "halogen" are meant fluorine, chlorine, bromine or iodine atoms.

Compounds of general formulae Ia and Ib may have acid groups, mainly carboxyl groups, and/or basic groups such as e.g. amino functions. Compounds of general formulae Ia and Ib may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form.

However, the application also includes the individual diastereomeric pairs of antipodes or mixtures thereof, which are obtained if there is more than one chiral element in the compounds of general formulae Ia and Ib, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids.

So-called prodrugs of compounds of general formulae Ia and Ib are also encompassed by this invention. The term prodrug is used to denote any molecule that releases the active principle of general formulae Ia and Ib in-vivo after administration to mammals. The prodrug may have little or no pharmacological activity per se, but releases the active principle of general formulae Ia and Ib in-vivo after administration and this has the activity described. Prodrugs for compounds of general formulae Ia and Ib may be prepared by modifying suitable functional groups in the compound of general formulae Ia and Ib, as known to the skilled man in this field. (H. Bundgaard (Editor), Design of Prodrugs. (1986), Elsevier)

This invention also includes those metabolites that are derived from the compounds of general formulae Ia and Ib. By metabolites are meant, in this context, compounds that are formed in-vivo from the compound of general formulae Ia and Ib after administration. Examples of metabolites include:
  methyl groups of the compound of general formulae Ia and Ib may be converted into the corresponding hydroxymethyl groups. (—CH$_3$→—CH$_2$OH)
  alkoxy groups of the compound of general formulae Ia and Ib may be converted into the corresponding hydroxyl groups. (—OR→—OH)
  secondary amines of the compound of general formulae Ia and Ib may be converted into the corresponding primary amines. (—NR$_1$R$_2$→—NHR$_1$ or —NHR$_2$)
  nitrogen atoms of the compound of general formulae Ia and Ib may be converted into the corresponding nitrogen oxides. (=N—→=N$^+$—(O$^-$)—)

METHODS OF PREPARATION

The invention also relates to a process for preparing the compounds of general formulae Ia and Ib

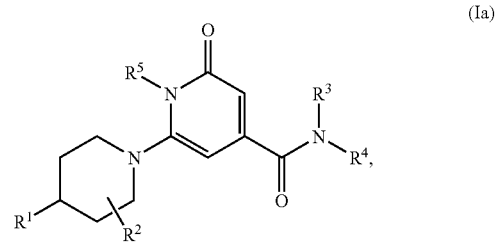

(Ia)

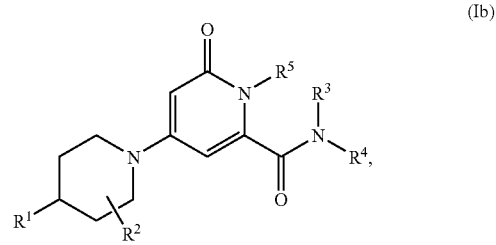

(Ib)

wherein R$^1$, R$^2$, R$^3$, R$^4$ and R$^5$ are as hereinbefore defined.

Some methods of preparing the compounds of general formula Ia according to the invention are illustrated in the following synthesis schemes and Examples.

The regioisomeric compounds of general formula Ib, wherein R$^1$, R$^2$, R$^3$, R$^4$ and R$^5$ are as hereinbefore defined may be prepared analogously to the methods described hereinafter. In some cases the order of carrying out the reaction schemes may be varied in order to simplify the reactions or prevent unwanted by-products. The Examples that follow are provided to make the invention fully comprehensible. The Examples are intended to illustrate the invention and should in no way restrict it.

The compounds according to the invention may be prepared according to the schemes and specific examples provided or corresponding modifications thereof. Modifications to these reactions which are known to the skilled man but not described in detail here may also be implemented. The general methods of preparing the compounds according to the invention will become apparent to the skilled man from a study of the following schemes.

Starting compounds are commercially available or are prepared by processes which are described in the literature, known in the art or as described herein. Before the reaction is carried out corresponding functional groups in the compounds may be protected by conventional protective groups. These protective groups may be cleaved again at a suitable stage within the reaction sequence using methods familiar to the skilled man.

In the reactions described below, any reactive groups present such as hydroxy, carboxy, amino, alkylamino, amide or imino groups may be protected during the reaction by conventional protective groups that are cleaved again after the reaction.

For example
a suitable protective group for a hydroxy group may be the methoxy, benzyloxy, trimethylsilyl, acetyl, benzoyl, tert.-butyl, trityl, benzyl or tetrahydropyranyl group,
suitable protective groups for a carboxyl group may be the trimethylsilyl, methyl, ethyl, tert.-butyl, benzyl or tetrahydropyranyl group, and
suitable protective groups for an amide group may be the N-methoxymethyl-(MOM), N-benzyloxymethyl (BOM), N-(trimethylsilyl)ethoxymethyl (SEM), N-tert-butyldimethylsiloxymethyl, N-tert-butyldimethylsilyl (TBDMS), N-triisopropylsilyl-(TIPS), N-benzyl, N-4-methoxybenzyl (PMB), N-triphenylmethyl (Trt), N-tert-butoxycarbonyl (BOC), N-benzyloxycarbonyl (Cbz) or N-trimethylsilylethylsulphonyl (SES)
a suitable protective group for an amino, alkylamino or imino group may be the acetyl, trifluoroacetyl, benzoyl, ethoxycarbonyl, tert.-butoxycarbonyl, benzyloxycarbonyl, benzyl, methoxybenzyl or 2,4-dim ethoxybenzyl group and additionally, for the amino group, the phthalyl group.

Other protective groups and their cleavage are described in T. W. Greene, P. G. M. Wuts, "Protective Groups in Organic Synthesis", Wiley, 1991 and 1999.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is conveniently cleaved in the presence of boron tribromide in a solvent such as methylene chloride at temperatures between −35 and −25° C. Alternatively a methoxy group may also be cleaved using Brønsted acids with or without a solvent. Preferably pyridine hydrochloride is used at elevated temperatures without a solvent.

A 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

A methoxymethyl group may be cleaved in the presence of an acid such as concentrated hydrochloric acid in a solvent such as dimethoxyethane. Alternatively an acid such as trifluoroacetic acid may also be used without a solvent.

An N-(trimethylsilyl)ethoxymethyl group may be cleaved in the presence of TBAF and 1,3-dimethyl-3,4,5,6-tetrahydro-2(1H)-pyrimidone. Alternatively the SEM protective group may also be cleaved with an acid such as hydrogen chloride in an organic solvent such as dioxane or ethanol.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine at temperatures between 0 and 100° C., preferably at ambient temperature and under an inert gas, or by treating with a catalytic amount of tris-(triphenylphosphine)-rhodium (I)chloride in a solvent such as aqueous ethanol and optionally in the presence of a base such as 1,4-diazabicyclo[2,2,2] octane at temperatures between 20 and 70° C.

The following methods of preparing the compounds of general formula Ia according to the invention wherein $R^1$, $R^2$, $R^3$, $R^4$ and $R^5$ are as hereinbefore defined and their precursors have proved particularly suitable:

Scheme 1:

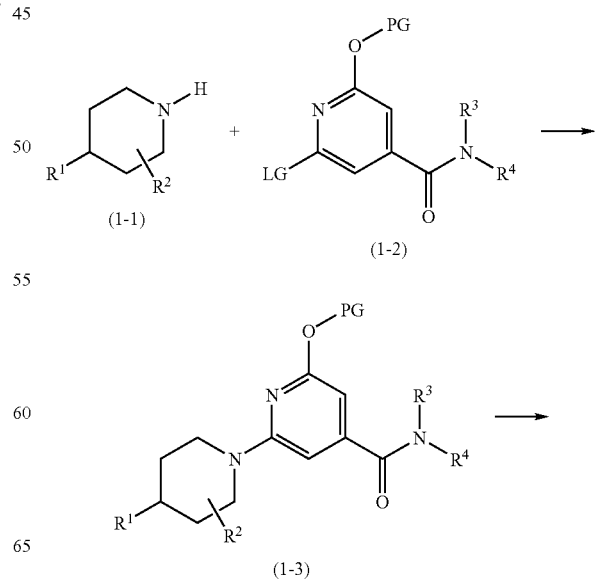

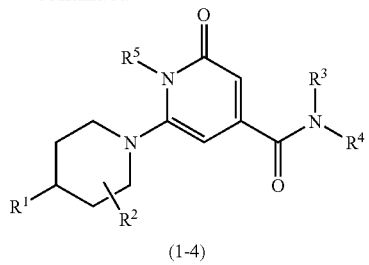

(1-4)

Scheme 2:

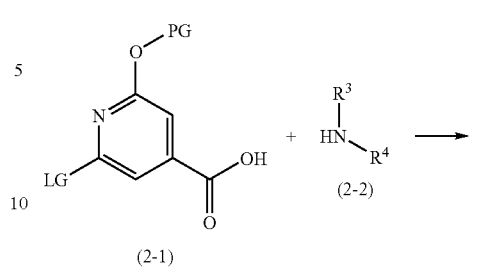

(2-1)    (2-2)

(2-3)

The preparation of a compound of general formula (I-4), wherein $R^1$, $R^2$, $R^3$ and $R^4$ are as hereinbefore defined and $R^5$ denotes a hydrogen atom, is shown in Scheme 1. A compound of general formula (1-1), wherein $R^1$ and $R^2$ are as hereinbefore defined, may be reacted with a compound of general formula (1-2), wherein $R^3$ and $R^4$ are as hereinbefore defined, LG denotes a leaving group and PG denotes a protective group. The leaving group LG may be halides, preferably chlorides and bromides, —$SO_2CH_3$, —$OSO_2CH_3$, —$OSO_2C_6H_4$—$CH_3$ or —S—$CH_3$ (—S—$CH_3$ requires further reaction with an organic peroxide in order to be able to be converted into the actual leaving group) etc., but the list is not restrictive. It is most particularly preferable to use chlorides. Protective groups PG for the hydroxy functionality are known to the skilled man or are described in the literature (T. W. Greene, P. G. M. Wuts, "Protective Groups in Organic Synthesis", Wiley, 1999). The methoxy protecting group is most particularly preferred.

The reaction may be carried out in an inert solvent using an auxiliary base in a temperature range from 0° C. to the reflux temperature of the solvent. The reaction is carried out in a suitable inert solvent, such as tetrahydrofuran, toluene, xylene, dialkylformamide (particularly preferably dimethylformamide), cyclic amides (particularly preferably N-methylpyrrolidone), 1,4-dioxane, acetonitrile or in mixtures of solvents. Examples of suitable auxiliary bases are tertiary amines such as triethylamine or ethyldiisopropylamine, alkali metal carbonates such as potassium carbonate or sodium carbonate, sodium hydride (NaH) or lithium diisopropylamide (LDA). The inert solvent used must be compatible with the base used. Preferably the reaction is carried out in N-methylpyrrolidone, at temperatures between ambient temperature and the reflux temperature of the solvent in the presence of potassium carbonate as auxiliary base. Starting from a compound of general formula (I-3), wherein $R^1$, $R^2$, $R^3$ and $R^4$ are as hereinbefore defined and PG denotes a protective group, a compound of general formula (1-4), wherein $R^1$, $R^2$, $R^3$ and $R^4$ are as hereinbefore defined and $R^5$ denotes a hydrogen atom, may be obtained by ether cleavage as shown in Scheme 1. Ethers can be cleaved with Brønsted acids or Lewis acids. It is most preferable to react compounds of general formula (I-3) with pyridine hydrochloride without a solvent at elevated temperatures. Protective groups PG for the hydroxy functionality are known to the skilled man or are described in the literature (T. W. Greene, P. G. M. Wuts, "Protective Groups in Organic Synthesis", Wiley, 1999). The methoxy protecting group is most particularly preferred.

Compounds of general formula (2-3), wherein $R^3$ and $R^4$ are as hereinbefore defined, LG represents a leaving group and PG represents a protective group, may be synthesised analogously to Scheme 2. The leaving group LG may be halides, preferably chlorides and bromides, —$SO_2CH_3$, —$OSO_2CH_3$, —$OSO_2C_6H_4$—$CH_3$ or —S—$CH_3$ (—S—$CH_3$ requires further reaction with an organic peroxide in order to be able to be converted into the actual leaving group) etc., but the list is not restrictive. It is most particularly preferable to use chlorides. Protective groups PG for the hydroxy functionality are known to the skilled man or are described in the literature (T. W. Greene, P. G. M. Wuts, "Protective Groups in Organic Synthesis", Wiley, 1999). It is most preferable to protect the hydroxy functionality with a methoxy protecting group.

Carboxylic acids of general formula (2-1) wherein PG represents a protective group and LG denotes a leaving group, may be reacted with compounds of general formula (2-2), wherein $R^3$ and $R^4$ are as hereinbefore defined, using standard peptide coupling reagents and a base in an inert solvent to obtain amides of general formula (2-3) (cf e.g. Houben-Weyl, Methoden der Organischen Chemie, vol. 15/2). Inert solvents that may be used are dimethylformamide, N-methylpyrrolidone, dim ethoxyethane, dichloromethane, acetonitrile or mixtures of solvents. The preferred solvent is dimethylformamide. Suitable bases are, in particular, amine bases such as e.g. triethylamine or diisopropylethylamine. Suitable coupling reagents may be for example 1H-benzotriazol-1-yl-oxy-tripyrrolidino-phosphonium-hexafluorophosphate (PyBOP), dicyclohexylcarbodiimide (DCC), diisopropylcarbodiimide (DIC), ethyl-(3-dimethylaminopropyl)-carbodiimide, O-(1H-benzo-triazol-1-yl)-N,N—N,N-tetramethyl-uronium hexafluorophosphate (HBTU) or tetrafluoroborate (TBTU) or 1H-benzotriazol-1-yl-oxy-tris-(dimethylamino)-phosphonium hexafluorophosphate (BOP). The use of TBTU is particularly preferred. The activation of the carboxyl group may also be carried out using a corresponding acid anhydride or acid chloride. The reaction is generally carried out in a temperature range from −20° C. to the reflux temperature of the solvent at normal pressure. It is particularly preferable to use diisopropylethylamine as base and dimethylformamide as solvent.

The compounds of general formula (3-3), wherein $R^1$, $R^2$, $R^3$ and $R^4$ are as hereinbefore defined and $R^5$ denotes a $C_{1-6}$-alkyl group, may be synthesised analogously to Scheme 3.

Scheme 3:

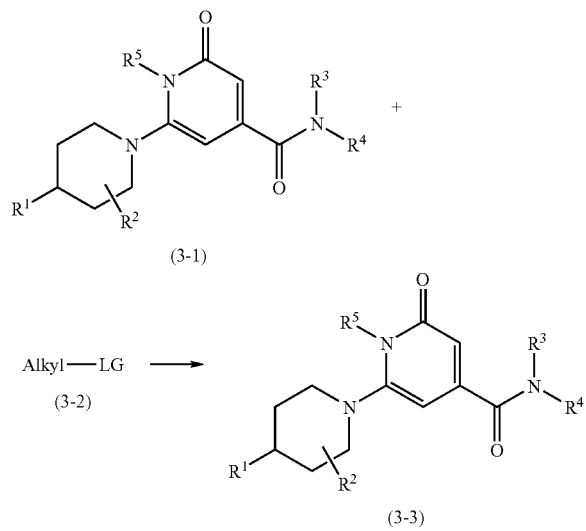

A compound of general formula (3-1), wherein $R^1$, $R^2$, $R^3$ and $R^4$ are as hereinbefore defined and $R^5$ denotes a hydrogen atom, may be reacted with a compound of general formula (3-2), wherein alkyl denotes a $C_{1-6}$-alkyl group and LG denotes a leaving group. The leaving group used may be halides, preferably bromides and iodides, —$OSO_2CH_3$, —$OSO_2C_6H_4$—$CH_3$, etc., although this list is not restrictive. The use of iodides is most particularly preferred. The use of methyl iodides is most particularly preferred. The reaction may be carried out in an inert solvent using an auxiliary base in a temperature range from 0° C. to the reflux temperature of the solvent. Dimethylformamide, N-methylpyrrolidone, dimethylsulphoxide, acetonitrile or mixtures of solvents may be used as inert solvents. The preferred solvent is dimethylsulphoxide. Suitable auxiliary bases may be alkali metal carbonates such as potassium carbonate, sodium carbonate or caesium carbonate. The inert solvent used must be compatible with the base used. The use of caesium carbonate is particularly preferred.

In some cases the end product may be further derivatised, e.g. by manipulation of the substituents. These manipulations may be, inter alia, those which are generally known to the skilled man, such as oxidation, reduction, alkylation, acylation and hydrolysis, but need not be restricted to the above.

The new compounds of general formulae Ia and Ib according to the invention may contain one or more chiral centres. If for example there are two chiral centres present, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formulae Ia and Ib may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formulae Ia and Ib is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium-carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formulae Ia and Ib may also be obtained by performing the syntheses described above with a suitable reaction component in the (R) or (S) configuration.

The new compounds of general formulae Ia and Ib and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC membranes (~20 μg protein) are incubated for 180 minutes at ambient temperature with 50 pM $^{125}$I-iodotyrosyl-Calcitonin-Gene-Related Peptide and increasing concentrations of the test substances in a total volume of 250 it (assay buffer: 10 mM tris, 50 mM NaCl, 5 mM $MgCl_2$, 1 mM EDTA, pH=7.4). The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity after the presence of 1 μM BIBN4096BS during incubation.

The concentration binding curves are analysed using computer-aided non-linear curve fitting.

The compounds mentioned hereinbefore show $K_i$ values ≦50 μm in the test described.

B. CGRP Antagonism in SK-N-MC Cells

SK-N-MC cells (~1000 cells per well) are incubated for 30 minutes in the presence of increasing concentrations of CGRP and different concentrations of the test substance.

The cAMP contents of the samples are determined using an AlphaScreen cAMP assay kit (Perkin Elmer) and the $pA_2$ values of antagonistically acting substances are determined graphically.

The compounds according to the invention exhibit CGRP-antagonistic properties in the in vitro test model described, in a dosage range between $10^{-12}$ and $10^{-4}$ M.

To demonstrate that the compounds of general formulae Ia and Ib exhibit good to very good CGRP-antagonistic activities with different structural elements, the following Table gives the $K_i$ values obtained according to the test procedure described above. It should be noted that the compounds were selected for their different structural elements and not in order to emphasise specific compounds:

| Example | $K_i$ [nM] |
| --- | --- |
| (2) | 480 |
| (3) | 8.4 |
| (4) | 3.8 |

INDICATIONS

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for the treatment of irritable bowel syndrome (IBS) and for the preventive and acute-therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from ⅕ of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

COMBINATIONS

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistics, corticosteroids, calcium antagonists, $5\text{-HT}_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. MGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQtype blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. Sst2 receptor agonists may be added.

The dosage of these active substances is expediently 1/5 of the lowest usually recommended dose to 1/1 of the normally recommended dose, i.e. for example 20 to 100 mg of sumatriptan.

FORMULATIONS

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. In amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formulae Ia and Ib according to the preferred embodiments above.

It is particularly preferable if the compounds of general formulae Ia and Ib are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of general formulae Ia and Ib are administered by inhalation, particularly preferably if they are administered once or twice a day. For this purpose, the compounds of general formulae Ia and Ib have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

EXPERIMENTAL SECTION

As a rule IR, $^1$H-NMR and/or mass spectra have been obtained for the compounds prepared. Unless stated otherwise, $R_f$ values are determined using ready-made TLC silica gel plates 60 F254 (E. Merck, Darmstadt, Item no. 1.05714) without chamber saturation.

The ratios given for the eluants relate to units by volume of the particular solvents. The units by volume given for $NH_3$ relate to a concentrated solution of $NH_3$ in water.

Eluant Systems Used for TLC:
  eluant A: DCM/cyclohexane/MeOH/$NH_4OH$=70/15/15/2
  eluant B: petroleum ether/ethyl acetate=2/1

Unless stated otherwise, the acid, base and salt solutions used in working up the reaction solutions are aqueous systems of the specified concentrations. Silica gel made by Millipore (MATREX™, 35-70 µm) is used for chromatographic purifications.

The HPLC data provided are measured under the parameters listed below and using the columns mentioned:

Columns Used:

(column temperature: 30° C.; injection volume: 5 μL; detection at 254 nm)

| | |
|---|---|
| S1 | Zorbax column (Agilent Technologies), SB (Stable Bond) C18; 3.5 μm; 4.6 × 75 mm |
| S2 | Waters Sunfire, SB (Stable Bond) C18; 3.5 μm; 4.6 × 75 mm |
| S3 | Agilent Bonus C18; 5 μm, 4.6 × 75 mm |
| S4 | Zorbax column (Agilent Technologies), SB (Stable Bond) C18; 1.8 μm; 3.0 × 30 mm |
| S5 | Zorbax column (Agilent Technologies), SB (Stable Bond) C18; 5 μm; 4.6 × 75 mm |
| S6 | Waters Symmetry C18; 3.5 μm; 4.6 × 75 mm |
| S7 | Waters XBridge C18; 3.5 μm; 4.6 × 75 mm (basic column) |

Solvents Used:

for the columns S1 to S6 (acid conditions) the following solvents were used:

solvent A: water (with 0.1% formic acid)

solvent B: acetonitrile (with 0.1% formic acid)

for the column S7 (basic conditions) the following solvents were used:

solvent A: water (with 0.1% NH$_4$OH)

solvent B: acetonitrile (with 0.1% NH$_4$OH)

(the percentages given relate to the total volume)

Gradients:

| gradient (flow) | time [min] | % A | % B |
|---|---|---|---|
| G1 | 0.0 | 95 | 5 |
| (0.8 mL/min) | 8.0 | 50 | 50 |
| | 9.0 | 10 | 90 |
| | 10.0 | 10 | 90 |
| | 11.0 | 95 | 5 |
| G2 | 0.00 | 95 | 5 |
| (1.6 mL/min) | 0.10 | 95 | 5 |
| | 1.75 | 5 | 95 |
| | 1.90 | 5 | 95 |
| | 1.95 | 95 | 5 |
| | 2.00 | 95 | 5 |
| G3 | 0.00 | 95 | 5 |
| (1.6 mL/min) | 4.50 | 10 | 90 |
| | 5.00 | 10 | 90 |
| | 5.50 | 95 | 5 |
| G4 | 0.00 | 95 | 5 |
| (1.6 mL/min) | 4.00 | 50 | 50 |
| | 4.50 | 10 | 90 |
| | 5.00 | 10 | 90 |
| | 5.50 | 95 | 5 |
| G5 | 0.00 | 90 | 10 |
| (1.6 mL/min) | 4.50 | 10 | 90 |
| | 5.50 | 10 | 90 |
| G6 | 0.0 | 95 | 5 |
| (0.8 mL/min) | 9.0 | 10 | 90 |
| | 10.0 | 10 | 90 |
| | 11.0 | 95 | 5 |
| G7 | 0.00 | 95 | 5 |
| (1.6 mL/min) | 2.00 | 50 | 50 |
| | 2.25 | 10 | 90 |
| | 2.50 | 10 | 90 |
| | 2.75 | 95 | 5 |

Methods:

| method | column | gradient |
|---|---|---|
| method A | S1 | G4 |
| method B | S2 | G4 |
| method C | S4 | G2 |
| method D | S6 | G4 |
| method E | S1 | G3 |
| method F | S3 | G3 |
| method G | S5 | G4 |
| method H | S1 | G5 |
| method K | S2 | G3 |
| method L | S1 | G2 |
| method M | S7 | G3 |
| method N | S2 | G1 |
| method O | S4 | G7 |

In preparative HPLC purifications, the products are collected either under mass control or by UV detection. The fractions containing product are combined and freeze-dried. The following columns may be used for preparative HPLC separations:

| | |
|---|---|
| S8 | Agilent Zorbax SB C18, 50 × 150 mm, 5 μm |
| S9 | Agilent Zorbax Stable Bond, 50 × 140 mm, 7 μm |
| S10 | Waters Sunfire C18, 30 × 100 mm, 5 μm |
| S11 | Waters Symmetry 50 × 140 mm, 7 μm |
| S12 | Agilent Zorbax Stable Bond C18, 30 × 100 mm, 5 μm, |

The following solvent systems may be used for the preparative HPLC separation:

solvent A: water (with 0.1% formic acid)
solvent B: acetonitrile (with 0.1% formic acid)
solvent A: water (with 0.15% formic acid)
solvent B: acetonitrile (with 0.15% formic acid)
solvent A: water (with 0.3% formic acid)
solvent B: acetonitrile
solvent A: water (with 0.3% formic acid)
solvent B: acetonitrile (with 0.3% formic acid)
solvent A: water (with 0.1% NH$_4$OH)
solvent B: acetonitrile (with 0.1% NH$_4$OH)

The percentages given relate in each case to the total volume.

In the absence of any more information regarding the configuration, it is unclear whether there are pure enantiomers involved or whether partial or even total racemisation has taken place.

The following abbreviations are used in the test descriptions:

AcOH acetic acid
BINAP 2,2'-bis-(diphenylphosphino)-1,1'-binaphthyl
BOC tert.-butyloxycarbonyl
CAD circulating air dryer
CDI 1,1'-carbonyldiimidazole
conc. concentrated
Cyc cyclohexane
DCM dichloromethane
DIPE diisopropylether
DIPEA diisopropylethylamine
DMF N,N-dimethylformamide
dppf 1,1'-bis-(diphenylphosphino)ferrocene
of th. of theory
d-water deionised water
EI electron jet ionisation (in MS)
eq equivalents ESI electrospray ionisation (in MS)
EtOAc ethyl acetate
EtOH ethanol
h hour(s)
HCl hydrogen chloride
HPLC High Performance Liquid Chromatography
HPLC-MS HPLC coupled mass spectrometry
i.vac. in vacuo (under vacuum)
M molar
mmol millimol
mL millilitre
μL microlitre
MeOH methanol
MS mass spectrometry
MW molecular weight [g/mol]
NaOAc sodium acetate
NaOH sodium hydroxide
NH$_4$OH ammonium hydroxide (aqueous ammonia solution, 30%)
NMP N-methylpyrrolidine
PE petroleum ether
quant. quantitative
R$_f$ retention factor (in TLC)
R$_t$ retention time (in HPLC)
RT ambient temperature
TBTU O-(benzotriazol-1-yl)-N,N,N',N'-tetramethyluronium tetrafluoroborate
TEA triethylamine
TFA trifluoroacetic acid
THF tetrahydrofuran
TLC thin layer chromatography
XantPhos 4,5-bis(diphenylphosphino)-9.9-dimethylxanthene
XPhos 2-dicyclohexylphosphino-2',4',6'-triisopropylbiphenyl Preparation of the Starting Compounds Intermediate 1a 1-piperidin-4-yl-1,3-dihydroimidazo[4,5-b]pyridin-2-one-dihydrochloride

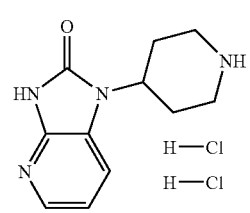

This compound and its precursors were synthesised as described in International Application WO 2005/013894.
ESI-MS: m/z=219 (M+H)$^+$
R$_f$: 0.11 (silica gel, DCM/MeOH/NH$_4$OH=80:20:2)

Intermediate 1b

1-Piperidin-4-yl-1,3-dihydroimidazo[4,5-b]pyridin-2-one

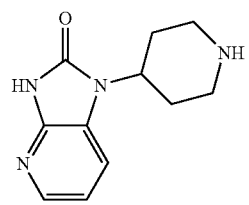

Step 1: Benzyl 4-(2-chloro-pyridin-3-yl-amino)-piperidine-1-carboxylate

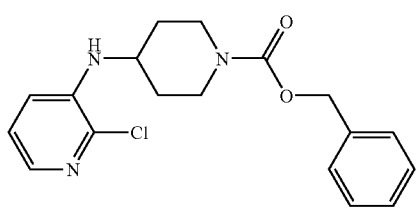

560 mL (7.25 mol) TFA were added dropwise at about 15° C. to 930 g (3.99 mol) of N-benzyloxycarbonyl-4-piperidone and 466 g (3.63 mol) of 2-chloro-3-aminopyridine in 9.5 L of isopropyl acetate. 922 g (4.35 mol) of sodium triacetoxyborohydride were added batchwise. The mixture was stirred until the reaction was complete. At RT the reaction mixture was combined with 860 mL sodium hydroxide solution (2 mol/L). The organic phase was separated off, washed with 5 L water and concentrated by evaporation.
Yield: 1250 g (crude, quant.)
ESI-MS: m/z=346 (M+H)$^+$ Step 2: Benzyl 4-[1-(2-chloro-pyridin-3-yl)-ureido]-piperidine-1-carboxylate

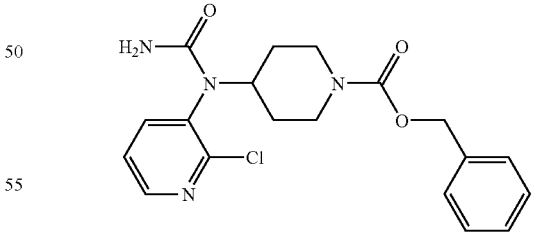

530 mL (6.1 mol) chlorosulphonyl isocyanate were placed in 6 L THF and cooled to −15° C. A solution of 1.25 kg (3.63 mol) benzyl 4-(2-chloro-pyridin-3-yl-amino)-piperidine-1-carboxylate in 7 L of THF was then added to this mixture within one hour in such a way that the temperature of the reaction mixture did not exceed −7° C. The mixture was stirred for 90 minutes at about −8° C. and then 700 mL of water were added dropwise within 30 minutes. The mixture was stirred for 30 minutes at about 10° C. and then 8.1 L sodium hydroxide solution (2 mol/L) were slowly added. The reaction mixture was then heated to 50° C. and the phases were separated. The organic phase was washed with 2 L of water. Then 10 L of solvent were distilled off from the organic phase, 15 L of butyl acetate were added to the residue and from this another 8 L were distilled off again. The product was crystallised by slow cooling to 0° C. The precipitate was suction filtered, washed with 2 L butyl acetate and dried at 40° C.

Yield: 1108 g (79% of th.)
ESI-MS: m/z=389/391(M+H)$^+$

Step 3: Benzyl 4-(2-oxo-2,3-dihydro-imidazo[4,5-b]pyridin-1-yl)-piperidine-1-carboxylate

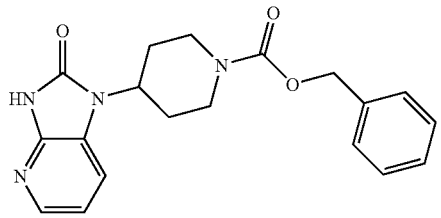

1108 g (2.85 mol) of benzyl 4-[1-(2-chloro-pyridin-3-yl)-ureido]-piperidine-1-carboxylate were refluxed with 720 g (8.57 mol) sodium hydrogen carbonate in 14.5 L of tert-amyl alcohol. 3 L of solvent were distilled off. The reaction mixture was cooled to 35° C. and mixed with 11 mL water. Then 13 g (0.058 mol) palladium acetate and 49 g (0.115 mol) 1,4-bis-(diphenylphosphino)-butane (DPPB) were added and the mixture was heated to reflux temperature. It was stirred at 100° C. until the reaction was complete, then cooled to RT and 7.5 L of water were added. The organic phase was separated off, washed with 5 L water and then evaporated down. Two lots of 3 L of isopropyl acetate were added to the oily residue and it was distilled off. Then the residue was dissolved hot in 7 L of isopropyl acetate and the mixture was slowly cooled to ambient temperature. The solid that crystallised out was suction filtered, washed with 2 L isopropyl acetate and tert.-butyl-methylether and dried at 50° C.

Yield: 690 g (69% of th.)
ESI-MS: m/z=353 (M+H)$^+$

Step 4: 1-Piperidin-4-yl-1,3-dihydro-imidazol-[4,5-b]pyridin-2-one

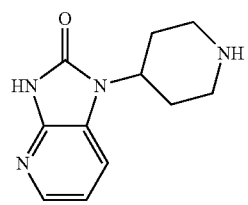

690 g (1.96 mol) benzyl 4-(2-oxo-2,3-dihydro-imidazo[4,5-b]pyridin-1-yl)-piperidine-1-carboxylate were dissolved in 5.4 L methanol and hydrogenated at 60° C. with the addition of 46 g Pd/C (10%; 6.6% by weight) at a hydrogen pressure of 60 psi until the uptake of hydrogen was complete. The catalyst was filtered off. 4 L of methanol were distilled off from the filtrate. 2 L of methylcyclohexane were added and another 1.5 L of solvent were distilled off. The suspension thus obtained was suction filtered, the residue was washed with methylcyclohexane and dried at 40° C.

Yield: 446 g (100% of th.)
ESI-MS: m/z=219 (M+H)$^+$

Intermediate 2

7-methoxy-3-piperidin-4-yl-1,3,4,5-tetrahydro-1,3-benzodiazepin-2-one

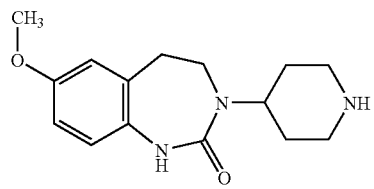

Step 1: (5-methoxy-2-nitrophenyl)-acetonitrile

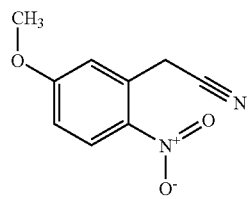

24.0 g (214 mmol) potassium-tert-butoxide in 100 mL DMF were slowly added dropwise to a solution of 13.2 g (86.0 mmol) 4-nitroanisole and 18.0 g (107 mmol) of 4-chlorophenoxy-acetonitrile in 50 mL DMF. The reaction mixture was stirred for 30 min at −10° C. and then poured into 300 g of a 1:1 mixture of conc. HCl and ice. After extraction with EtOAc the organic phase was washed with water, dried and evaporated down i. vac. The residue was treated with a 1:1 mixture PE/EtOAc and the product that crystallised out was suction filtered. After washing with a 1:1 mixture of petroleum ether/EtOAc the crystals were dried in the air.

Yield: 6.5 g (39% of theoretical)
ESI-MS: m/z=210 (M+NH$_4$)$^+$
R$_f$: 0.45 (silica gel; PE/EtOAc=1:1)

Step 2: 2-(5-methoxy-2-nitrophenyl)-ethylamine

Under a nitrogen atmosphere, 200 mL (200 mmol) of a 1M borane in THF solution were slowly added dropwise at RT to 12.6 g (65.7 mmol) (5-methoxy-2-nitrophenyl)-acetonitrile in 380 mL THF. The reaction mixture was refluxed for 2 h. After cooling 30 mL methanol were added dropwise within 20 min. During this time the temperature was maintained at 10° C. to 20° C. with an ice bath. The reaction mixture was left for 30 min at RT with stirring and then within 30 min 45 mL of a 2M aqueous HCl solution were added dropwise thereto. The reaction mixture was concentrated by rotary evaporation i. vac. The residue was diluted with water to approx. 200 mL and extracted with 200 mL EtOAc. The aqueous phase was made alkaline with a 15% (w/v) aqueous potassium carbonate solution and continuously extracted overnight with diethyl ether using a rotary perforator according to Ludwig (Messrs Normag). The organic extract was evaporated to dryness by rotary evaporation.

Yield: 9.98 g (77% of theoretical)
ESI-MS: m/z=197 (M+H)$^+$
R$_t$ (HPLC): 2.1 min (method E)

Step 3: (1-benzylpiperidin-4-yl)-[2-(5-methoxy-2-nitrophenyl)-ethyl]-amine

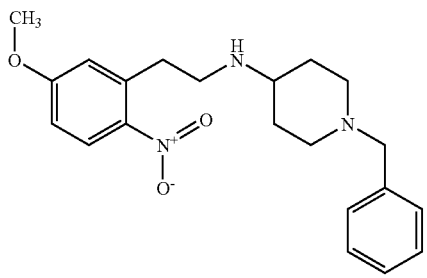

Under a nitrogen atmosphere a mixture of 9.98 g (50.9 mmol) 2-(5-methoxy-2-nitrophenyl)-ethylamine, 9.80 mL (54.9 mmol) N-benzylpiperidone and 6.30 mL (114 mmol) acetic acid in 270 mL dichloromethane was cooled to 0° C. in an ice bath. At this temperature 14.2 g (67.0 mmol) sodium triacetoxyborohydride were added batchwise within 20 min. The reaction mixture was left for a further 4 h at 0° C. and warmed up to RT overnight. Then the mixture was combined with 400 mL of a 15% (w/v) aqueous potassium carbonate solution and stirred for 1 h at RT. The organic phase was separated off, dried and concentrated by rotary evaporation.

Yield: 18.8 g (quantitative)
ESI-MS: m/z=370 (M+H)$^+$
R$_t$ (HPLC): 1.9 min (method E)

Step 4: [2-(2-amino-5-methoxyphenyl)-ethyl]-(1-benzylpiperidin-4-yl)-amine

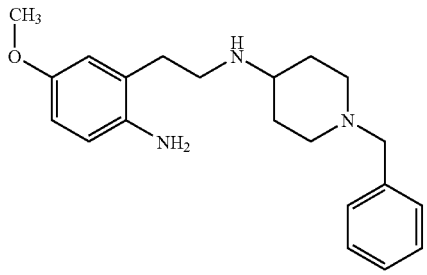

26.0 g (70.3 mmol) (1-benzylpiperidin-4-yl)-[2-(5-methoxy-2-nitrophenyl)-ethyl]-amine were hydrogenated with 5.00 g (2.45 mmol) rhodium charcoal (5%, moistened with water) in 350 mL methanol in a 3 bar hydrogen atmosphere for 3 h at RT. The catalyst was removed by suction filtering and the solution was concentrated by rotary evaporation. The residue was immediately further reacted without any further purification.

Yield: 23.9 g (quantitative)
R$_t$ (HPLC): 0.99 min (method A)

Step 5: 3-(1-benzylpiperidin-4-yl)-7-methoxy-1,3,4,5-tetrahydro-1,3-benzodiazepin-2-one

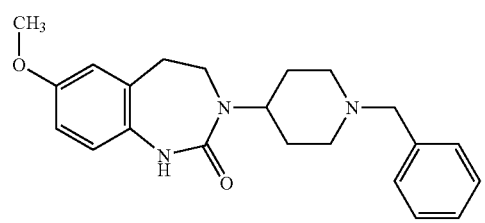

35.0 g (216 mmol) N,N'-carbonyldiimidazole were added to 23.9 g (70.3 mmol) [2-(2-amino-5-methoxyphenyl)-ethyl]-(1-benzylpiperidin-4-yl)-amine in 175 mL DMF and the mixture was stirred for 2 h at 100° C. The reaction mixture was poured onto approx. 1 kg ice water and stirred overnight. The precipitated product was suction filtered, washed with water and dried. The residue was stirred with DIPE and suction filtered. The solid product was washed with DIPE and dried.

Yield: 21.6 g (84% of theoretical)
ESI-MS: m/z=366 (M+H)$^+$
R$_t$ (HPLC): 2.12 min (method E)

Step 6: 7-methoxy-3-piperidin-4-yl-1,3,4,5-tetrahydro-1,3-benzodiazepin-2-one

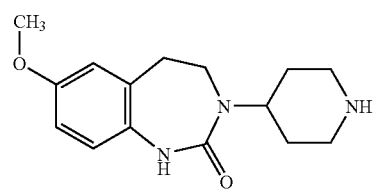

A mixture of 21.6 g (59.2 mmol) 3-(1-benzylpiperidin-4-yl)-7-methoxy-1,3,4,5-tetrahydro-1,3-benzodiazepin-2-one and 2.5 g palladium on charcoal (10%) in 300 mL methanol was hydrogenated in a 3 bar hydrogen atmosphere at 50° C. until the reaction was complete. The catalyst was removed by suction filtering and the mother liquor was concentrated by rotary evaporation. The residue was triturated with DIPE, suction filtered, washed with DIPE and dried.

Yield: 13.2 g (81% of theoretical)
ESI-MS: m/z=276 (M+H)$^+$
R$_t$ (HPLC): 0.73 min (method L)

Intermediate 3

(2-chloro-6-methoxypyridin-4-yl)-(5-fluoro-2,3-dihydroindol-1-yl)-methanone

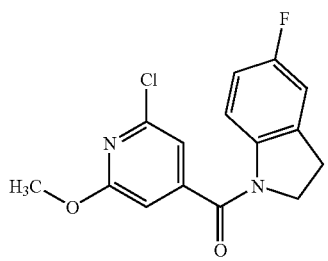

0.965 g (3.00 mmol) TBTU was added at RT to 0.500 g (2.67 mmol) 2-chloro-6-methoxyisonicotinic acid, 0.366 g (2.67 mmol) 5-fluoroindoline and 0.421 mL (3.00 mmol) triethylamine in 10.0 mL DMF. The mixture was stirred for 2 h at RT and then purified by preparative HPLC. The fractions containing the product were combined and evaporated down i. vac.

Yield: 0.700 g (86% of theoretical)
ESI-MS: m/z=307/309 (M+H)$^+$ (Cl)
R$_t$ (HPLC): 1.60 min (method C)

Intermediate 4

5-fluoro-3,3-dimethyl-2,3-dihydro-1H-indole

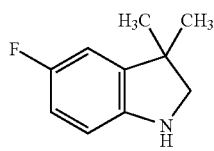

Step 1: 1-acetyl-5-fluoro-1,3-dihydroindol-2-one

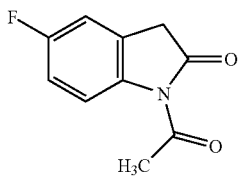

At 170° C. 3.0 g (20 mmol) 5-fluoroindolinone were stirred in 10 mL (98 mmol) acetic anhydride for 3 h. After cooling to RT the mixture was poured onto 200 mL ice water, the precipitated substance was suction filtered and washed with 100 mL water. The solid was recrystallised from water and ethanol. The precipitated product was suction filtered, washed with water and dried i. vac.

Yield: 2.4 g (63% of theory)
ESI-MS: m/z=192 (M+H)$^+$
R$_t$ (HPLC): 1.2 min (method C)

Step 2: 1-acetyl-5-fluoro-3,3-dimethyl-1,3-dihydroindol-2-one

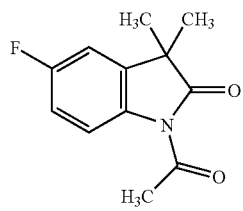

At 0° C. to 5° C., 1.14 g (26.0 mmol) sodium hydride (55% in mineral oil) was added batchwise under an argon atmosphere to 2.40 g (12.4 mmol) 1-acetyl-5-fluoro-1,3-dihydroindol-2-one in 30 mL DMF and the mixture was stirred for 1 h. Then 1.91 mL (31.0 mmol) methyl iodide were added dropwise and the mixture was stirred overnight at RT. The reaction mixture was poured onto water and the precipitated substance was suction filtered. The solid was washed with water and dried i. vac.

Yield: 2.1 g (76% of theory)
ESI-MS: m/z=222 (M+H)$^+$
R$_t$ (HPLC): 1.48 min (method C)

Step 3:
5-fluoro-3,3-dimethyl-1,3-dihydroindol-2-one

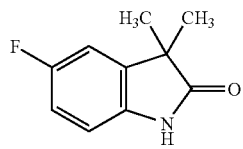

2.10 g (9.49 mmol) 1-acetyl-5-fluoro-3,3-dimethyl-1,3-dihydro-indol-2-one in 20 mL isopropanol were refluxed with 50 mL of a 6M aqueous HCl solution for 1 h. After cooling the isopropanol was eliminated i. vac. The residue was diluted with water and cooled with ice. The precipitated substance was suction filtered and washed with water. The solid was dried i. vac.

Yield: 1.40 g (82% of theory)
ESI-MS: m/z=180 (M+H)$^+$
R$_t$ (HPLC): 1.14 min (method C)

Step 4: 5-fluoro-3,3-dimethyl-2,3-dihydro-1H-indole

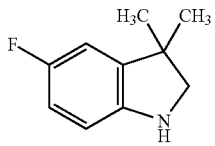

Under an argon atmosphere a solution of 9.30 mL (9.30 mmol) of a 1M solution of lithium aluminium hydride in THF and 10 mL THF was slowly added dropwise to 1.40 g (7.81 mmol) 5-fluoro-3,3-dimethyl-1,3-dihydroindol-2-one in 50 mL THF. Then the reaction mixture was heated to 70° C. for 1 h. After cooling 2 mL water were added. The solution was dried on sodium sulphate and filtered off. The solvent was eliminated i. vac.

Yield: 1.30 g (quant.)
ESI-MS: m/z=166 (M+H)+
R$_t$ (HPLC): 0.75 min (method C)

Intermediate 5

(2-chloro-6-methoxypyridin-4-yl)-(5-fluoro-3,3-dimethyl-2,3-dihydroindol-1-yl)-methanone

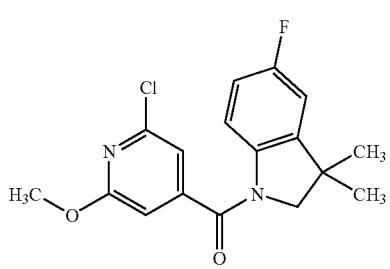

This compound was obtained analogously to (2-chloro-6-methoxypyridin-4-yl)-(5-fluoro-2,3-dihydroindol-1-yl)-methanone from 0.500 g (2.67 mmol) 2-chloro-6-methoxy-isonicotinic acid, 0.439 g (2.66 mmol) 5-fluoro-3,3-dimethyl-2,3-dihydro-1H-indole and 0.421 mL (3.00 mmol) triethylamine in 10.0 mL DMF.
Yield: 0.600 g (67% of theory)
ESI-MS: m/z=335/337 (M+H)+ (Cl)
R$_t$ (HPLC): 1.73 min (method C)

Intermediate 6

1-[4'-(5-fluoro-2,3-dihydroindole-1-carbonyl)-6'-methoxy-3,4,5,6-tetrahydro-2H-[1,2']bipyridinyl-4-yl]-1,3-dihydroimidazo[4,5-b]pyridin-2-one

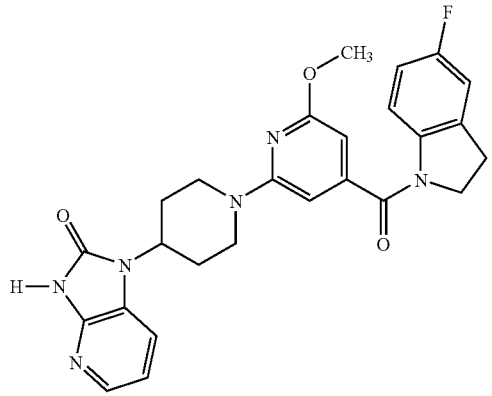

A mixture of 0.361 g (1.24 mmol) 1-piperidin-4-yl-1,3-dihydroimidazo[4,5-b]pyridin-2-one dihydrochloride, 0.380 mg (1.24 mmol) (2-chloro-6-methoxypyridin-4-yl)-(5-fluoro-2,3-dihydroindol-1-yl)-methanone and 514 mg (3.72 mmol) potassium carbonate in 3.0 mL NMP was stirred for 8 h at 130° C. After cooling the reaction mixture to RT the precipitate formed was filtered off and purified by preparative HPLC. The fractions containing the product were combined and evaporated down i. vac.
Yield: 0.090 g (15% of theoretical)
ESI-MS: m/z=489 (M+H)+
R$_t$ (HPLC): 1.50 min (method C)

Intermediate 7

3-[4'-(5-fluoro-2,3-dihydroindole-1-carbonyl)-6'-methoxy-3,4,5,6-tetrahydro-2H-1,2'-bipyridinyl-4-yl]-7-methoxy-1,3,4,5-tetrahydro-1,3-benzodiazepin-2-one

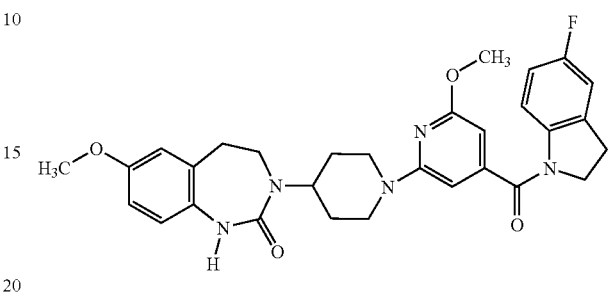

A mixture of 0.633 g (2.30 mmol) 7-methoxy-3-piperidin-4-yl-1,3,4,5-tetrahydro-1,3-benzodiazepin-2-one, 0.700 mg (2.28 mmol) (2-chloro-6-methoxypyridin-4-yl)-(5-fluoro-2,3-dihydroindol-1-yl)-methanone and 954 mg (6.90 mmol) potassium carbonate in 5.0 mL NMP was stirred for 8 h at 130° C. After cooling the reaction mixture to RT the precipitate formed was filtered off and purified by preparative HPLC. The fractions containing the product were combined and evaporated down i. vac. The residue obtained was digested in DMF and the product remaining as a solid was suction filtered and dried i. vac. The mother liquor was again purified by preparative HPLC, the fractions containing product were combined and evaporated down i. vac. The residue was triturated with ethanol, the solid product was suction filtered and dried i. vac.
Yield: 0.490 g (39% of theoretical)
ESI-MS: m/z=546 (M+H)+
R$_t$ (HPLC): 1.50 min (method C)

Intermediate 8

1-[4'-(5-fluoro-3,3-dimethyl-2,3-dihydroindole-1-carbonyl)-6'-methoxy-3,4,5,6-tetrahydro-2H-[1,2']bipyridinyl-4-yl]-1,3-dihydroimidazo[4,5-b]pyridin-2-one

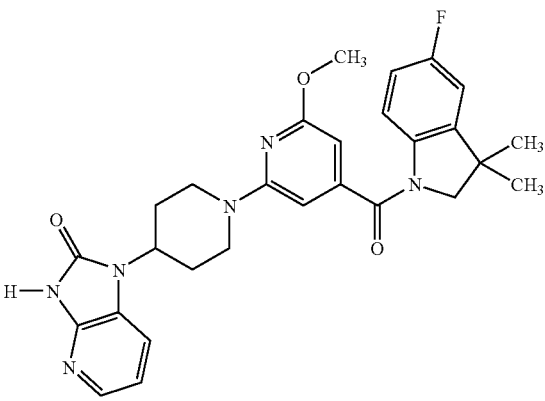

This compound was obtained analogously to 1-[4'-(5-fluoro-2,3-dihydroindole-1-carbonyl)-6'-methoxy-3,4,5,6- tetrahydro-2H-[1,2']bipyridinyl-4-yl]-1,3-dihydroimidazo[4,5-b]pyridin-2-one from 262 mg (0.900 mmol) 1-piperidin-4-yl-1,3-dihydroimidazo[4,5-b]pyridin-2-one dihydrochloride, 300 mg (0.90 mmol) (2-chloro-6-methoxy-pyridin-4-yl)-(5-fluoro-3,3-dimethyl-2,3-dihydroindol-1-yl)-methanone and 373 mg (2.70 mmol) potassium carbonate in 3.0 mL NMP.

Yield: 40 mg (9% of theoretical)

ESI-MS: m/z=517 (M+H)+

$R_t$ (HPLC): 1.62 min (method C)

Intermediate 9

1-[4'-(4,5-Difluoro-2,3-dihydro-indole-1-carbonyl)-6'-methoxy-3,4,5,6-tetrahydro-2H-[1,2']bipyridinyl-4-yl]-1,3-dihydro-imidazo[4,5-b]pyridin-2-one

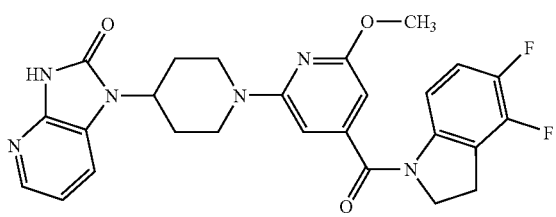

Step 1: (2-Chloro-6-methoxy-pyridin-4-yl)-(4,5-difluoro-2,3-dihydro-indol-1-yl)-methanone

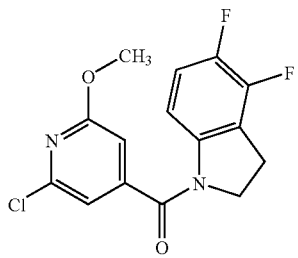

1.22 g (3.80 mmol) TBTU were added at RT to 0.685 g (3.65 mmol) 2-chloro-6-methoxyisonicotinic acid, 0.700 g (3.65 mmol) 4,5-fluoroindoline-dihydrochloride and 1.12 mL (8.00 mmol) triethylamine in 10.0 mL DMF. The mixture was stirred for 2 h at RT and then poured onto 200 mL of potassium carbonate solution (aqueous, 7%). The precipitate formed was suction filtered, washed with water and dried i. vac.

Yield: 1.05 g (89% of th.)

ESI-MS: m/z=325/327 (M+H)+ (Cl)

$R_t$ (HPLC): 1.66 min (method C)

Step 2: 1-[4'-(4,5-Difluoro-2,3-dihydro-indole-1-carbonyl)-6'-methoxy-3,4,5,6-tetra-hydro-2H-[1,2']bipyridinyl-4-yl]-1,3-dihydro-imidazo[4,5-b]pyridin-2-one

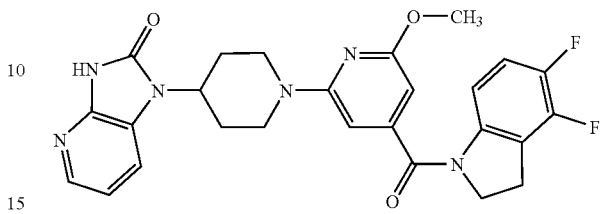

0.982 g (4.50 mmol) 1-Piperidin-4-yl-1,3-dihydroimidazo[4,5-b]pyridin-2-one and 500 mg (1.54 mmol) (2-chloro-6-methoxy-pyridin-4-yl)-(4,5-difluoro-2,3-dihydro-indol-1-yl)-methanone in 3.0 mL NMP were stirred for 12 h at 130° C. After the reaction mixture had cooled to RT the precipitate formed was filtered off and purified by preparative HPLC. The product-containing fractions were combined and lyophilised.

Yield: 0.250 g (32% of th.)

ESI-MS: m/z=507 (M+H)+

$R_t$ (HPLC): 1.59 min (method C)

Intermediate 10

1-[6'-(5-Fluoro-2,3-dihydro-indole-1-carbonyl)-2'-methoxy-3,4,5,6-tetrahydro-2H-[1,4']bipyridinyl-4-yl]-1,3-dihydro-imidazo[4,5-b]pyridin-2-one

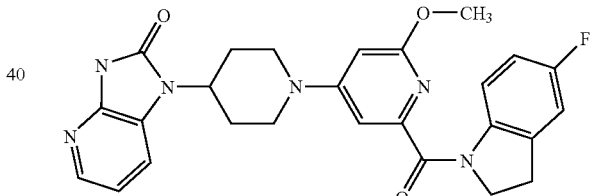

Step 1: (4-Chloro-6-methoxy-pyridin-2-yl)-(5-fluoro-2,3-dihydro-indol-1-yl)-methanone

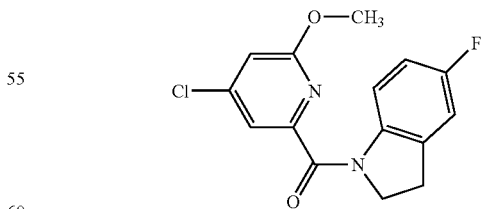

550 mg (2.93 mmol) 4-chloro-6-methoxy-pyridine-2-carboxylate, 411 mg (3.00 mmol) 5-fluoroindoline, 1.06 g (3.30 mmol) TBTU and 927 µL (6.60 mmol) triethylamine in 5.00 mL DMF were stirred for 3 h at RT. The reaction mixture was purified by HPLC. The product-containing fractions were combined and evaporated down using the rotary evaporator.

Yield: 450 mg (50% of th.)
ESI-MS: m/z=307/309 (M+H)+ (CI)
R_t (HPLC): 1.7 min (method C)

Step 2: 1-[6'-(5-Fluoro-2,3-dihydro-indole-1-carbonyl)-2'-methoxy-3,4,5,6-tetrahydro-2H-[1,4']bipyridinyl-4-yl]-1,3-dihydro-imidazo[4,5-b]pyridin-2-one

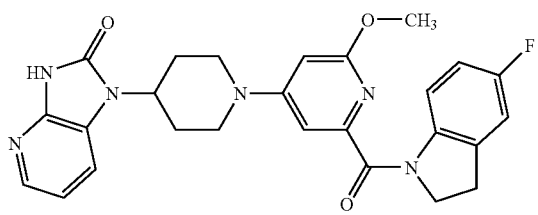

436 mg (2.00 mmol) 1-Piperidin-4-yl-1,3-dihydro-imidazo[4,5-b]pyridin-2-one and 200 mg (0.652 mmol) of (4-chloro-6-methoxy-pyridin-2-yl)-(5-fluoro-2,3-dihydro-indol-1-yl)-methanone in 2 mL NMP were stirred overnight at 120° C. The reaction mixture was purified by preparative HPLC. The product-containing fractions were combined and evaporated down using the rotary evaporator.

Yield: 62 mg (20% of th.)
ESI-MS: m/z=487 (M−H)−
R_t (HPLC): 1.7 min (method C)

Preparation of the End Compounds

Example 1

4'-(5-fluoro-2,3-dihydroindole-1-carbonyl)-4-(2-oxo-2,3-dihydroimidazo[4,5-b]pyridin-1-yl)-3,4,5,6-tetrahydro-2H,1'H-[1,2']bipyridinyl-6'-one

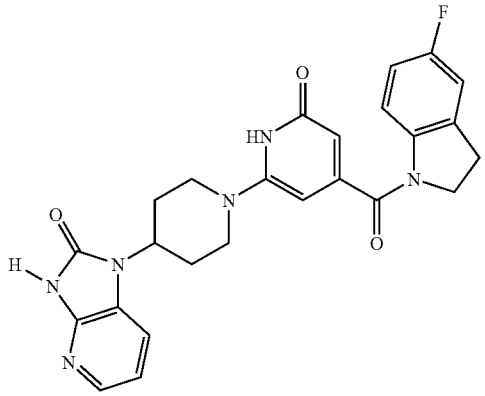

A well stirred mixture of 20 mg (0.041 mmol) 1-[4'-(5-fluoro-2,3-dihydroindole-1-carbonyl)-6'-methoxy-3,4,5,6-tetrahydro-2H-[1,2']bipyridinyl-4-yl]-1,3-dihydroimidazo[4,5-b]pyridin-2-one and 100 mg (0.865 mmol) pyridine hydrochloride was kept in a melt for 7 min using a hot air blower. After the reaction mixture had cooled it was dissolved in DMF and purified by preparative HPLC. The fractions containing the product were combined and lyophilised.

Yield: 11 mg (57% of theoretical)
ESI-MS: m/z=476 (M+H)+
R_t (HPLC): 1.17 min (method C)

Example 2

4'-(5-fluoro-2,3-dihydroindole-1-carbonyl)-1'-methyl-4-(2-oxo-2,3-dihydroimidazo[4,5-b]-pyridin-1-yl)-3,4,5,6-tetrahydro-2H,1'H-[1,2']bipyridinyl-6'-one

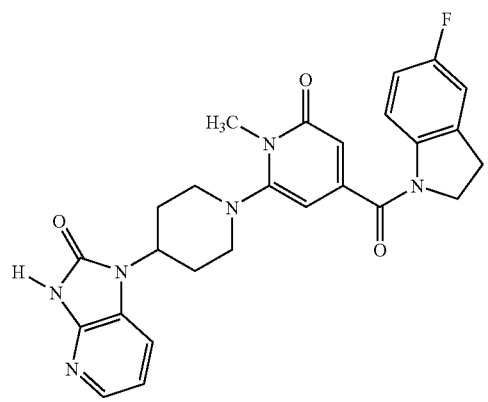

50 mg (0.11 mmol) of 4'-(5-fluoro-2,3-dihydroindole-1-carbonyl)-4-(2-oxo-2,3-dihydroimidazo[4,5-b]pyridin-1-yl)-3,4,5,6-tetrahydro-2H,1'H-[1,2']bipyridinyl-6'-one were placed in 0.50 mL DMSO at RT. To this were added 88 mg (0.27 mmol) caesium carbonate and the mixture was stirred for 15 min. Then a solution of 6.5 μL (0.11 mmol) methyl iodide in DMSO was added and the mixture was stirred for 2 h at RT. More methyl iodide was added (3.3 μL, 0.055 mmol) and the mixture was stirred for a further 2 h at RT. The reaction mixture was purified by preparative HPLC. The fractions containing the product were combined and lyophilised.

Yield: 15 mg (29% of theoretical)
ESI-MS: m/z=489 (M+H)+
R_t (HPLC): 1.88 min (method O)

Example 3

3-[4'-(5-fluoro-2,3-dihydroindole-1-carbonyl)-6'-oxo-3,4,5,6,1',6'-hexahydro-2H-1,2'-bipyridinyl-4-yl]-7-methoxy-1,3,4,5-tetrahydro-1,3-benzodiazepin-2-one

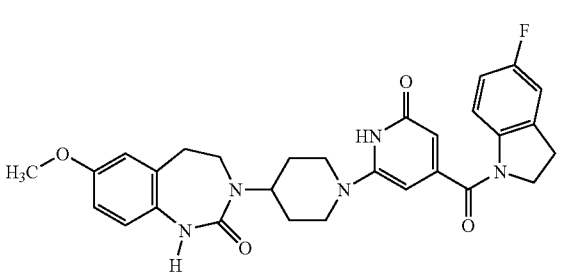

This compound was obtained analogously to 4'-(5-fluoro-2,3-dihydroindole-1-carbonyl)-4-(2-oxo-2,3-dihydroimidazo[4,5-b]pyridin-1-yl)-3,4,5,6-tetrahydro-2H,1'H-[1,2'] bipyridinyl-6'-one from 415 mg (0.761 mmol) 3-[4'-(5-fluoro-2,3-dihydroindole-1-carbonyl)-6'-methoxy-3,4,5,6-tetrahydro-2H-1,2'-bipyridinyl-4-yl]-7-methoxy-1,3,4,5-tetrahydro-1,3-benzodiazepin-2-one and 1.50 g (13.0 mmol) pyridine hydrochloride.

Yield: 39 g (10% of theoretical)
ESI-MS: m/z=532 (M+H)⁺
R_t (HPLC): 4.80 min (method N)

Example 4

4'-(5-fluoro-3,3-dimethyl-2,3-dihydroindole-1-carbonyl)-4-(2-oxo-2,3-dihydroimidazo[4,5-b]-pyridin-1-yl)-3,4,5,6-tetrahydro-2H,1'H-[1,2']bipyridinyl-6'-one

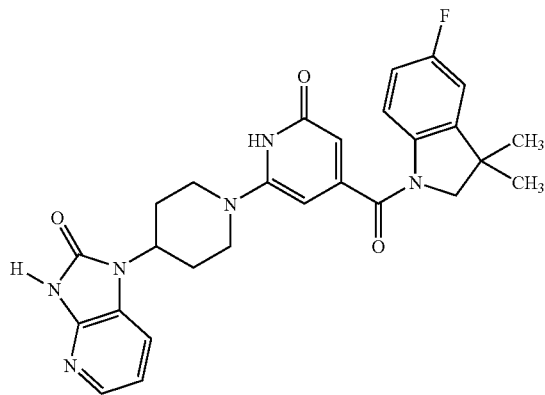

This compound was obtained analogously to 4'-(5-fluoro-2,3-dihydroindole-1-carbonyl)-4-(2-oxo-2,3-dihydroimidazo[4,5-b]pyridin-1-yl)-3,4,5,6-tetrahydro-2H,1'H-[1,2']bipyridinyl-6'-one from 60 mg (0.12 mmol) 1-[4'-(5-fluoro-3,3-dimethyl-2,3-dihydroindole-1-carbonyl)-6'-methoxy-3,4,5,6-tetrahydro-2H-[1,2']bipyridinyl-4-yl]-1,3-dihydroimidazo[4,5-b]pyridin-2-one and 300 mg (2.6 mmol) pyridine hydrochloride.

Yield: 20 mg (34% of theoretical)
ESI-MS: m/z=503 (M+H)⁺
R_t (HPLC): 1.17 min (method C)

Example 5

4'-(5-fluoro-3,3-dim ethyl-2,3-dihydroindole-1-carbonyl)-1'-methyl-4-(2-oxo-2,3-dihydroimidazo[4,5-b]pyridin-1-yl)-3,4,5,6-tetrahydro-2H,1'H-[1,2']bipyridinyl-6'-one

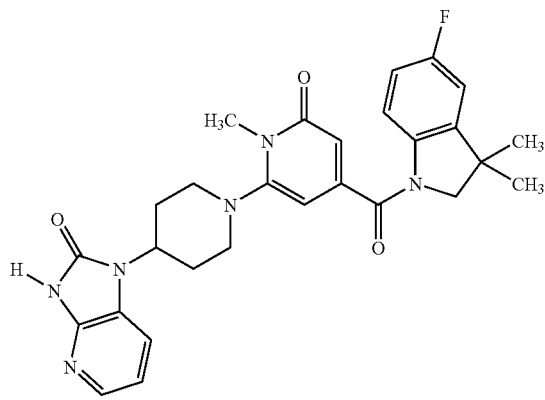

This compound was obtained analogously to 4'-(5-fluoro-2,3-dihydroindole-1-carbonyl)-1'-methyl-4-(2-oxo-2,3-dihydroimidazo[4,5-b]pyridin-1-yl)-3,4,5,6-tetrahydro-2H,1'H-[1,2']bipyridinyl-6'-one from 20 mg (0.040 mmol) of 4'-(5-fluoro-3,3-dimethyl-2,3-dihydroindole-1-carbonyl)-4-(2-oxo-2,3-dihydroimidazo[4,5-b]pyridin-1-yl)-3,4,5,6-tetrahydro-2H,1'H-[1,2']bipyridinyl-6'-one, 3.8 µL (0.060 mmol) methyl iodide and 33 mg (0.10 mmol) caesium carbonate in 0.50 mL DMSO.

Yield: 15 mg (73% of theoretical)
ESI-MS: m/z=517 (M+H)⁺
R_t (HPLC): 2.16 min (method C)

Example 6

4'-(4,5-Difluoro-2,3-dihydro-indole-1-carbonyl)-4-(2-oxo-2,3-dihydro-imidazo[4,5-b]pyridin-1-yl)-3,4,5,6-tetrahydro-2H,1'H-[1,2']bipyridinyl-6'-one

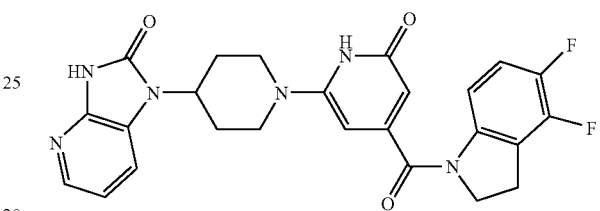

A well stirred mixture of 100 mg (0.197 mmol) 1-[4'-(4,5-difluoro-2,3-dihydro-indole-1-carbonyl)-6'-methoxy-3,4,5,6-tetrahydro-2H-[1,2']bipyridinyl-4-yl]-1,3-dihydro-imidazo[4,5-b]pyridin-2-one and 0.500 g (4.33 mmol) pyridine hydrochloride was kept in a melt for 7 min using a hot air blower. After the reaction had cooled the mixture was dissolved in DMF and purified by preparative HPLC. The product-containing fractions were combined and lyophilised.

Yield: 56 mg (58% of th.)
ESI-MS: m/z=493 (M+H)⁺
R_t (HPLC): 1.27 min (method C)

Example 7

6'-(5-Fluoro-2,3-dihydro-indole-1-carbonyl)-4-(2-oxo-2,3-dihydro-imidazo[4,5-b]pyridin-1-yl)-3,4,5,6-tetrahydro-2H,1'H-[1,4']bipyridinyl-2'-one

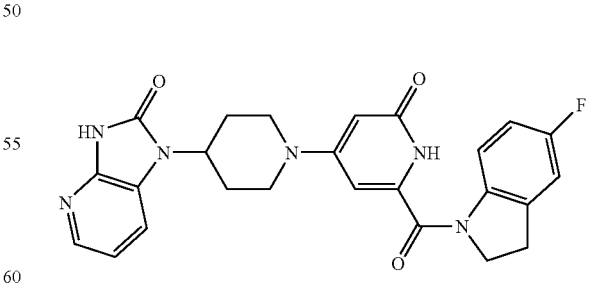

A well stirred mixture of 40 mg (0.082 mmol) 1-[6'-(5-fluoro-2,3-dihydro-indole-1-carbonyl)-2'-methoxy-3,4,5,6-tetrahydro-2H-[1,4']bipyridinyl-4-yl]-1,3-dihydro-imidazo-[4,5-b]pyridin-2-one and 0.020 g (1.7 mmol) pyridine hydrochloride was kept in a melt for 2 min using a hot air blower. After the reaction had cooled the mixture was dissolved in DMF and purified by preparative HPLC. The product-containing fractions were combined and lyophilised.

Yield: 22 mg (57% of th.)
ESI-MS: m/z=475 (M+H)$^+$
$R_t$ (HPLC): 1.1 min (method C)

The following Examples describe the preparation of pharmaceutical formulations that contain as active substance any desired compound of general formulae Ia and Ib:

Example I

Capsules for Powder Inhalation Containing 1 mg of Active Ingredient

Composition:
1 Capsule for Powder Inhalation Contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:
1 Puff Contains:

| | |
|---|---|
| active ingredient | 1.0 mg |
| benzalkonium chloride | 0.002 mg |
| disodium edetate | 0.0075 mg |
| purified water ad | 15.0 μl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:
1 Vial Contains:

| | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metered Dose Aerosol Containing 1 mg of Active Ingredient Composition:
1 Puff Contains:

| | |
|---|---|
| active ingredient | 1.0 mg |
| lecithin | 0.1% |
| propellant gas ad | 50.0 μl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance Per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

Example VII

Injectable Solution Containing 100 mg of Active Substance Per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4*2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

Example VIII

Lyophilisate Containing 10 mg of Active Substance

Composition:

| | |
|---|---|
| Active substance | 10 mg |
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (WfI); transferred into ampoules.

Example IX

Tablets Containing 20 mg of Active Substance

Composition:

| | |
|---|---|
| active substance | 20 mg |
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| | |
|---|---|
| active substance | 20 mg |
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size for 3 hard gelatine capsules in a capsule filling machine.

Example XI

Suppositories Containing 50 mg of Active Substance

Composition:

| | |
|---|---|
| active substance | 50 mg |
| hard fat (adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml

Composition:

| | |
|---|---|
| active substance | 10 mg |
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

The invention claimed is:
1. A compound of the formula Ia or Ib

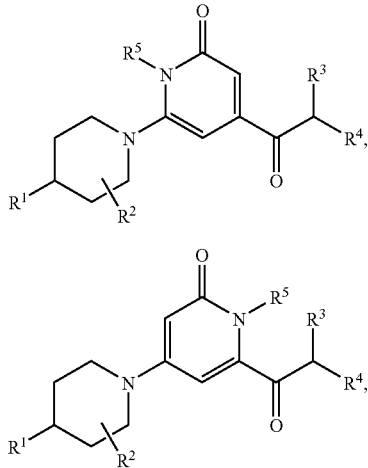

wherein
R$^1$ denotes a group of general formula II

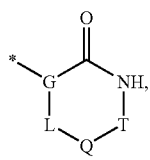

wherein
G-L denotes N, N—C(R$^{1.1}$)$_2$, C=C(R$^{1.1}$), C=N, C(R$^1$), C(R$^{1.1}$)—C(R$^{1.1}$)$_2$, C(R$^{1.1}$)—C(R$^{1.1}$)$_2$—C(R$^{1.1}$)$_2$, C=C(R$^{1.1}$)—C(R$^{1.1}$)$_2$, C(R$^{1.1}$)—C(R$^{1.1}$)=C(R$^{1.1}$), C(R$^{1.1}$)—C(R$^{1.1}$)$_2$—N(R$^{1.2}$), C=C(R$^{1.1}$)—N(R$^{1.2}$), C(R$^{1.1}$)—C(R$^{1.1}$)=N, C(R$^{1.1}$)—N(R$^{1.2}$)—C(R$^{1.1}$)$_2$, C=N—C(R$^{1.1}$)$_2$, C(R$^{1.1}$)—N=C(R$^{1.1}$), C=N—N(R$^{1.1}$)—N(R$^{1.2}$)—N(R$^{1.2}$), C=N—N(R$^{1.2}$), N—C(R$^{1.1}$)$_2$—C(R$^{1.1}$)$_2$, N—C(R$^{1.1}$)=C(R$^{1.1}$), N—C(R$^{1.1}$)$_2$—N(R$^{1.2}$), N—C(R$^{1.1}$)=N, N—N(R$^{1.2}$)—C(R$^{1.1}$)$_2$ or N—N=C(R$^{1.1}$), Q-T denotes C(R$^{1.3}$)$_2$—C(R$^{1.3}$)$_2$, C(R$^{1.3}$)=C(R$^{1.3}$), N=C(R$^{1.3}$), C(R$^{1.3}$)$_2$—C(=O), C(=O)—C(R$^{1.3}$)$_2$, C(R$^{1.3}$)$_2$—S(O)$_m$ or C(R$^{1.3}$)$_2$—N(R$^{1.3}$), while a group C(R$^{1.3}$)$_2$ contained in Q-T may also denote a cyclic group which is C$_{3-6}$-cycloalkyl, C$_{5-6}$-cycloalkenyl or heterocyclyl, or in a group C(R$^{1.3}$)$_2$—C(R$^{1.3}$)$_2$, C(R$^{1.3}$)=C(R$^{1.3}$) or C(R$^{1.3}$)$_2$—N(R$^{1.3}$) contained in Q-T in each case a group R$^{1.3}$ together with an adjacent group R$^{1.3}$ and the atoms to which these groups are bound may also denote a C$_{3-6}$-cycloalkyl, C$_{5-6}$-cycloalkenyl, heterocyclyl, aryl or heteroaryl group, which may be substituted independently of one another by 1, 2 or 3 substituents R$^{1.3.1}$, R$^{1.1}$ denotes
(a) H,
(b) C$_{1-6}$-alkyl, —CN, —OH, —O—C$_{1-3}$-alkyl,
(c) a C$_{1-3}$-alkyl or C$_{1-3}$-alkyl-O— group wherein each methylene group is substituted by up to two fluorine atoms and each methyl group is substituted by up to three fluorine atoms, R$^{1.2}$ denotes H or C$_{1-6}$-alkyl,
R$^{1.3}$ independently of one another denote
(a) H, C$_{1-6}$-alkyl, C$_{2-6}$-alkenyl, C$_{2-6}$-alkynyl, C$_{3-6}$-cycloalkyl,
(b) an aryl group optionally substituted by 1, 2 or 3 substituents R$^{1.3.2}$, wherein the substituents R$^{1.3.2}$ may be identical or different,
(c) a heteroaryl group optionally substituted by 1, 2 or 3 substituents R$^{1.3.2}$, wherein the substituents R$^{1.3.2}$ may be identical or different, or
(d) a heterocyclic group optionally substituted by 1, 2 or 3 substituents R$^{1.3.2}$, wherein the substituents R$^{1.3.2}$ may be identical or different, R$^{1.3.1}$ denotes
(a) H, halogen, C$_{1-6}$-alkyl, C$_{3-6}$-cycloalkyl,
(b) —O—R$^{1.3.1.1}$, —O—C$_{1-6}$-alkylene-NR$^{1.3.1.2}$R$^{1.3.1.3}$, —O—(CH$_2$)$_s$—O—R$^{1.3.1.1}$, —CO$_2$—R$^{1.3.1.1}$, —C(O)—NR$^{1.3.1.2}$R$^{1.3.1.3}$, —O—C(O)—NR$^{1.3.1.2}$R$^{1.3.1.3}$, —NR$^{1.3.1.1}$—C(O)—NR$^{1.3.1.2}$R$^{1.3.1.3}$, —NR$^{1.3.1.2}$—C(O)—R$^{1.3.1.3}$, —NR$^{1.3.1.2}$—C(O)—O—R$^{1.3.1.3}$, —SO$_2$—NR$^{1.3.1.2}$R$^{1.3.1.3}$, —NR$^{1.3.1.2}$—SO$_2$—R$^{1.3.1.3}$, —S(O)$_m$—R$^{1.3.1.2}$, —CN, —NR$^{1.3.1.2}$R$^{1.3.1.3}$, —NR$^{1.3.1.1}$—C(O)—NR$^{1.3.1.2}$R$^{1.3.1.3}$, —O—C(O)—R$^{1.3.1.1}$,
(c) a C$_{1-3}$-alkyl or C$_{1-3}$-alkyl-O— group wherein each methylene group is substituted by up to two fluorine atoms and each methyl group is substituted by up to three fluorine atoms,
(d) an aryl group substituted by 1, 2 or 3 substituents R$^{1.3.1.1}$, wherein the substituents R$^{1.3.1.1}$ may be identical or different,
(e) a heteroaryl group substituted by 1, 2 or 3 substituents R$^{1.3.1.1}$, wherein the substituents R$^{1.3.1.1}$ may be identical or different,
(f) a heterocyclic group substituted by 1, 2 or 3 substituents R$^{1.3.1.1}$, wherein the substituents R$^{1.3.1.1}$ may be identical or different, R$^{1.3.2}$ denotes
(a) halogen, C$_{1-6}$-alkyl, C$_{3-6}$-cycloalkyl,
(b) —O—R$^{1.3.2.1}$, —O—(CH$_2$)$_s$—O—R$^{1.3.2.1}$, —CO$_2$R$^{1.3.2.1}$, —C(O)—NR$^{1.3.2.2}$R$^{1.3.2.3}$, —O—(CO)—NR$^{1.3.2.2}$R$^{1.3.2.3}$, —N(R$^{1.3.2.1}$)—C(O)—NR$^{1.3.2.2}$R$^{1.3.2.3}$, —N(R$^{1.3.2.2}$)—C(O)—R$^{1.3.2.3}$, —N(R$^{1.3.2.2}$)—C(O)—O—R$^{1.3.2.3}$, —SO$_2$—NR$^{1.3.2.2}$R$^{1.3.2.3}$, —N(R$^{1.3.2.2}$)—SO$_2$—R$^{1.3.2.3}$, —S(O)$_m$—R$^{1.3.2.2}$, —CN, —NR$^{1.3.2.2}$R$^{1.3.2.3}$, —N(R$^{1.3.2.1}$)—C(O)—NR$^{1.3.2.2}$R$^{1.3.2.3}$, —O—C(O)—R$^{1.3.2.1}$ or
(c) a C$_{1-3}$-alkyl group wherein each methylene group is substituted by up to two fluorine atoms and each methyl group is substituted by up to three fluorine atoms, R$^{1.3.1.1}$ denotes
(a) H,
(b) C$_{1-6}$-alkyl, C$_{3-6}$-cycloalkyl, aryl, heteroaryl, benzyl which may be substituted by a group R$^{1.3.1.1.1}$, or
(c) a C$_{1-3}$-alkyl group wherein each methylene group is substituted by up to two fluorine atoms and each methyl group is substituted by up to three fluorine atoms, R$^{1.3.1.1.1}$ denotes halogen, HO— or C$_{1-6}$-alkyl-O—,
R$^{1.3.1.2}$ denotes
(a) H,
(b) C$_{1-6}$-alkyl, C$_{3-6}$-cycloalkyl, aryl, heteroaryl or benzyl, wherein the groups may be unsubstituted or substituted by halogen, HO— or C$_{1-6}$-alkyl-O—, or (c) a $C_{1-3}$-alkyl group wherein each methylene group is substituted by up to two fluorine atoms and each methyl group is substituted by up to three fluorine atoms, $R^{1.3.1.3}$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$ or fluorine, wherein the substituents $R^{1.3.1.1}$ are independent of one another, $R^{1.3.2.1}$ denotes
(a) H,
(b) $C_{1-6}$-alkyl, $C_{3-6}$-cycloalkyl, aryl, heteroaryl, benzyl which may be substituted by a group $R^{1.3.2.1.1}$, or
(c) a $C_{1-3}$-alkyl group wherein each methylene group is substituted by up to two fluorine atoms and each methyl group is substituted by up to three fluorine atoms, $R^{1.3.2.1.1}$ denotes halogen, HO— or $C_{1-6}$-alkyl-O—, $R^{1.3.2.2}$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^{1.3.2.3}$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$ or fluorine, wherein the substituents $R^{1.3.2.1}$ are independent of one another, m denotes one of the numbers 0, 1 or 2,
s denotes one of the numbers 1, 2 or 3, $R^2$ denotes
(a) H,
(b) F, —CN, $C_{1-3}$-alkyl, —$CO_2$—$R^{2.1}$ or
(c) a $C_{1-3}$-alkyl group wherein each methylene group is substituted by up to two fluorine atoms and each methyl group is substituted by up to three fluorine atoms, $R^{2.1}$ denotes H or $C_{1-6}$-alkyl, $R^3$ denotes
(a) H,
(b) $C_{1-6}$-alkylene-$R^{3.1}$,
(c) a $C_{3-6}$-cycloalkyl group substituted by one or two groups $R^{3.2}$,
(d) a $C_{5-7}$-cycloalkenyl group substituted by one or two groups $R^{3.2}$,
(e) an aryl group substituted by one or two groups $R^{3.2}$,
(f) a heterocyclyl group substituted by one or two groups $R^{3.2}$,
(g) a $C_{5-7}$-cycloalkyl group which may be fused to an aryl or heteroaryl group and is additionally substituted by one or two groups $R^{3.2}$,
(h) a heteroaryl group substituted by one or two groups $R^{3.2}$, or
(i) a $C_{1-3}$-alkyl group wherein each methylene group is substituted by up to two fluorine atoms and each methyl group is substituted by up to three fluorine atoms, $R^{3.1}$ denotes
(a) H,
(b) an aryl group substituted by the groups $R^{3.1.1}$ and $R^{3.1.2}$, or
(c) a heteroaryl group substituted by the groups $R^{3.1.1}$ and $R^{3.1.2}$, $R^{3.1.1}$ denotes
(a) H,
(b) halogen, $C_{1-3}$-alkyl, —OH, —CN, —O—$C_{1-3}$-alkyl, —O—C(O)—$C_{1-3}$-alkyl, —$NR^{3.1.1.1}R^{3.1.1.2}$, —S(O)$_m$—$C_{1-3}$-alkyl, —$NR^{3.1.1.1}$—C(O)—$C_{1-3}$-alkyl, —C(O)—$NR^{3.1.1.1}R^{3.1.12}$, —C(O)—O—$R^{3.1.1.3}$, —$NR^{3.1.1.1}$—C(O)—O—$C_{1-3}$-alkyl, —O—C(O)—$NR^{3.1.1.1}R^{3.1.12}$, or
(c) a $C_{1-3}$-alkyl- or —O—$C_{1-3}$-alkyl group wherein each methylene group is substituted by up to two fluorine atoms and each methyl group is substituted by up to three fluorine atoms, $R^{3.1.1.1}$ denotes H, $C_{1-3}$-alkyl and
$R^{3.1.1.2}$ denotes H, $C_{1-3}$-alkyl, or
$R^{3.1.1.1}$ and $R^{3.1.1.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$, $R^{3.1.1.3}$ denotes H, $C_{1-3}$-alkyl, $R^{3.1.2}$ denotes
(a) H,
(b) halogen, $C_{1-3}$-alkyl, —OH, —CN, —O—$C_{1-3}$-alkyl,
(c) a $C_{1-3}$-alkyl- or —O—$C_{1-3}$-alkyl group wherein each methylene group is substituted by up to two fluorine atoms and each methyl group is substituted by up to three fluorine atoms, or $R^{3.2}$ independently of one another denote
(a) H,
(b) halogen, $C_{1-3}$-alkyl, —OH, —CN, —O—$C_{1-3}$-alkyl, —O—C(O)—$C_{1-3}$-alkyl, —$NR^{3.2.1}R^{3.2.2}$, —S(O)$_m$—$C_{1-3}$-alkyl, —$NR^{3.2.1}$—C(O)—$C_{1-3}$-alkyl, —C(O)—$NR^{3.2.1}R^{3.2.2}$, —C(O)—O—$R^{3.2.3}$, —$NR^{3.2.1}$—C(O)—O—$C_{1-3}$-alkyl, —O—C(O)—$NR^{3.2.1}R^{3.2.2}$,
(c) a $C_{1-3}$-alkyl- or —O—$C_{1-3}$-alkyl group wherein each methylene group is substituted by up to two fluorine atoms and each methyl group is substituted by up to three fluorine atoms, $R^{3.2.1}$ denotes H, $C_{1-3}$-alkyl and
$R^{3.2.2}$ denotes H, $C_{1-3}$-alkyl, or
$R^{3.2.1}$ and $R^{3.2.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$, $R^{3.2.3}$ denotes H, $C_{1-3}$-alkyl, $R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{6-7}$-cycloalkenyl group substituted by one or two groups $R^{4.2}$,
  (e) an aryl group substituted by one or two groups $R^{4.2}$,
  (f) a heterocyclyl group substituted by one or two groups $R^{4.2}$,
  (g) a $C_{6-7}$-cycloalkyl group which may be fused to an aryl or heteroaryl group, while the resultant bicyclic group is additionally substituted by one or two groups $R^{4.2}$,
  (h) a heteroaryl group substituted by one or two groups $R^{4.2}$, or
  (i) a $C_{1-3}$-alkyl group wherein each methylene group is substituted by up to two fluorine atoms and each methyl group is substituted by up to three fluorine atoms, $R^{4.1}$ denotes
  (a) H,
  (b) an aryl group substituted by the groups $R^{4.1.1}$ and $R^{4.1.2}$, or
  (c) a heteroaryl group substituted by the groups $R^{4.1.1}$ and $R^{4.1.2}$, $R^{4.1.1}$ denotes
  (a) H,
  (b) halogen, $C_{1-3}$-alkyl, —OH, —CN, —O—$C_{1-3}$-alkyl, —O—C(O)—$C_{1-3}$-alkyl, —NR$^{4.1.1.1}$R$^{4.1.1.2}$, —S(O)$_m$—$C_{1-3}$-alkyl, —NR$^{4.1.1.1}$—C(O)—$C_{1-3}$-alkyl, —C(O)—NR$^{4.1.1.1}$R$^{4.1.1.2}$, —C(O)—O—R$^{4.1.1.3}$, —NR$^{4.1.1.1}$—C(O)—O—$C_{1-3}$-alkyl, —O—C(O)—NR$^{4.1.1.1}$R$^{4.1.1.2}$, or
  (c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.1}$ denotes H, $C_{1-3}$-alkyl and
$R^{4.1.1.2}$ denotes H, $C_{1-3}$-alkyl, or
$R^{4.1.1.1}$ and $R^{4.1.1.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$, $R^{4.1.1.3}$ denotes H, $C_{1-3}$-alkyl, $R^{4.1.2}$ denotes
  (a) H,
  (b) halogen, $C_{1-3}$-alkyl, —OH, —CN, —O—$C_{1-3}$-alkyl, or
  (c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ independently of one another denote
  (a) H,
  (b) halogen, $C_{1-3}$-alkyl, —OH, —CN, —O—$C_{1-3}$-alkyl, —O—C(O)—$C_{1-3}$-alkyl, —NR$^{4.2.1}$R$^{4.2.2}$, —S(O)$_m$—$C_{1-3}$-alkyl, —NR$^{4.2.1}$—C(O)—$C_{1-3}$-alkyl, —C(O)—NR$^{4.2.1}$R$^{4.2.2}$, —C(O)—O—R$^{4.2.3}$, —NR$^{4.2.1}$—C(O)—O—$C_{1-3}$-alkyl, —O—C(O)—NR$^{4.2.1}$R$^{4.2.2}$, or
  (c) a $C_{1-3}$-alkyl or —O—$C_{1-3}$-alkyl group wherein each methylene group is substituted by up to two fluorine atoms and each methyl group is substituted by up to three fluorine atoms, $R^{4.2.1}$ denotes H, $C_{1-3}$-alkyl and
$R^{4.2.2}$ denotes H, $C_{1-3}$-alkyl, or
$R^{4.2.1}$ and $R^{4.2.2}$ together with the nitrogen atom to which they are bound also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$, $R^{4.2.3}$ denotes H, $C_{1-3}$-alkyl, $R^3$ and $R^4$ together with the nitrogen atom to which they are bound denote:
  (a) a saturated 5-, 6- or 7-membered heterocyclic group which is substituted at a carbon atom by a group $R^{4.3}$ or by two groups $R^{4.3}$ and $R^{4.4}$,
  (b) a saturated 5-, 6- or 7-membered heterocyclic group which is substituted at two adjacent carbon atoms by in each case a group $R^{4.3}$ and $R^{4.4}$,
  (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
  (d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
  (e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or
  (f) a heteroaryl group which is substituted at 1, 2 or 3 carbon atoms by in each case a group $R^{4.5}$, $R^{4.3}$ independently of one another denote
  (a) H, $C_{1-3}$-alkyl, $C_{2-6}$-alkynyl, aryl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, or
  (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3.1}$ denotes H, $C_{1-3}$-alkyl-O—C(O)—, —NH$_2$, ($C_{1-4}$-alkyl)-NH, ($C_{1-4}$-alkyl)$_2$N, $C_{3-6}$-cycloalkyl, heterocyclyl, heteroaryl, aryl, $R^{4.4}$ denotes
  (a) H, $C_{1-3}$-alkyl-, —OH, —O—$C_{1-3}$-alkyl or
  (b) a $C_{1-3}$-alkyl or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl-, $C_{5-6}$-cycloalkenyl- or heterocyclyl group, $R^{4.5}$ independently of one another denote
  (a) H,
  (b) halogen, $C_{1-3}$-alkyl, —OH, —O—$C_{1-3}$-alkyl, —S(O)$_m$—$C_{1-3}$-alkyl, —NR$^{4.5.2}$R$^{4.5.3}$, —CN, —C(O)—O—R$^{4.5.1}$, —C(O)—NR$^{4.5.2}$R$^{4.5.3}$,
  (c) a $C_{1-3}$-alkyl or —O—$C_{1-3}$-alkyl group wherein each methylene group is substituted by up to two fluorine atoms and each methyl group is substituted by up to three fluorine atoms, or
  (d) aryl, heteroaryl,
$R^{4.5.1}$ denotes H, $C_{1-3}$-alkyl,
$R^{4.5.2}$ denotes H, $C_{1-3}$-alkyl,
$R^{4.5.3}$ denotes H, $C_{1-3}$-alkyl, or
$R^{4.5.2}$ and $R^{4.5.3}$ together with the nitrogen atom to which they are bound also denote a group which is selected from morpholinyl, thiomorpholinyl, piperidinyl, peridonyl, piperazinyl, pyrrolidinyl and azetidinyl, while the group may additionally be substituted by one or two substituents selected from F, —OH, —OCF$_3$, $C_{1-3}$-alkyl and CF$_3$,
$R^5$ denotes H, —CH$_2$—R$^{5.1}$ or benzyl, and
$R^{5.1}$ denotes a $C_{1-3}$-alkyl group wherein each methylene group is substituted by up to two fluorine atoms and each methyl group is substituted by up to three fluorine atoms,
or a tautomer or salt thereof.

2. A compound of the formula Ia or Ib according to claim 1, wherein
$R^1$ denotes a group of general formula II

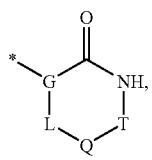

wherein
  G-L denotes N, N—C(R$^{1.1}$)$_2$, C=C(R$^{1.1}$), C=N, C(R$^1$), C(R$^{1.1}$)—C(R$^{1.1}$)$_2$, C(R$^{1.1}$)—C(R$^{1.1}$)$_2$—C(R$^{1.1}$)$_2$, C=C(R$^{1.1}$)—C(R$^{1.1}$)$_2$, C(R$^{1.1}$)—C(R$^{1.1}$)=C(R$^{1.1}$), C(R$^{1.1}$)—C(R$^{1.1}$)$_2$—N(R$^{1.2}$), C=C(R$^{1.1}$)—N(R$^{1.2}$), C(R$^{1.1}$)—C(R$^{1.1}$)$_2$=N, C(R$^{1.1}$)—N(R$^{1.2}$)—C(R$^{1.1}$)$_2$, C=N—C(R$^{1.1}$)$_2$, C(R$^{1.1}$)—N=C(R$^{1.1}$), C=N—N(R$^{1.1}$)—N(R$^{1.2}$)—N(R$^{1.2}$), C=N—N(R$^{1.2}$), N—C(R$^{1.1}$)$_2$—C(R$^{1.1}$)$_2$, N—C(R$^{1.1}$)=C(R$^{1.1}$), N—C(R$^{1.1}$)$_2$—N(R$^{1.2}$), N—C(R$^{1.1}$)=N, N—N(R$^{1.2}$)—C(R$^{1.1}$)$_2$ or N—N=C(R$^{1.1}$),
  Q-T denotes C(R$^{1.3}$)$_2$—C(R$^{1.3}$)$_2$, C(R$^{1.3}$)=C(R$^{1.3}$), N=C(R$^{1.3}$), C(R$^{1.3}$)$_2$—C(=O), C(=O)—C(R$^{1.3}$)$_2$, C(R$^{1.3}$)$_2$—S(O)$_m$ or C(R$^{1.3}$)$_2$—N(R$^{1.3}$),
  while a group C(R$^{1.3}$)$_2$ contained in Q-T may also denote a cyclic group which is selected from among cyclobutyl, cyclopentyl, cyclohexyl, cyclopentenyl, cyclohexenyl, dioxanyl, morpholinyl, thiomorpholinyl, thiomorpholinyl-S-oxide, thiomorpholinyl-S-dioxide, azetidinyl, pyrrolidinyl, piperidinyl, tetrahydrofuranyl, tetrahydropyranyl and piperazinyl, or
  in a group C(R$^{1.3}$)$_2$—C(R$^{1.3}$)$_2$, C(R$^{1.3}$)=C(R$^{1.3}$) or C(R$^{1.3}$)$_2$—N(R$^{1.3}$) contained in Q-T in each case a group R$^{1.3}$ together with an adjacent group R$^{1.3}$ and the atoms to which these groups are bound may also denote a group selected from cyclobutyl, cyclopentyl, cyclohexyl, cyclopentenyl, cyclohexenyl, dioxanyl, phenyl, napthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-S-oxide, thiomorpholinyl-S-dioxide, 1H-quinolinyl-2-one, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another denote by 1, 2 or 3 substituents R$^{1.3.1}$,
$R^{1.1}$ denotes
  (a) H,
  (b) $C_{1-6}$-alkyl, —CN, —OH, —O—$C_{1-3}$-alkyl, or
  (c) a $C_{1-3}$-alkyl or $C_{1-3}$-alkyl-O— group wherein each methylene group is substituted by up to two fluorine atoms and each methyl group is substituted by up to three fluorine atoms,
$R^{1.2}$ denotes H or $C_{1-6}$-alkyl,
$R^{1.3}$ independently of one another denote
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents R$^{1.3.2}$, wherein the substituents R$^{1.3.2}$ may be identical or different,
  (c) a heteroaryl group optionally substituted by 1, 2 or 3 substituents R$^{1.3.2}$, wherein the substituents R$^{1.3.2}$ may be identical or different, or
  (d) a heterocyclic group optionally substituted by 1, 2 or 3 substituents R$^{1.3.2}$, wherein the substituents R$^{1.3.2}$ may be identical or different,
$R^{1.3.1}$ denotes
  (a) H, halogen, $C_{1-6}$-alkyl, $C_{3-6}$-cycloalkyl,
  (b) —O—R$^{1.3.1.1}$, —O—$C_{1-6}$-alkylene-NR$^{1.3.1.2}$R$^{1.3.1.3}$, —O—(CH$_2$)$_s$—O—R$^{1.3.1.1}$, —CO$_2$—R$^{1.3.1.1}$, —C(O)—NR$^{1.3.1.2}$R$^{1.3.1.3}$, —O—C(O)—NR$^{1.3.1.2}$R$^{1.3.1.3}$, —NR$^{1.3.1.1}$—C(O)—NR$^{1.3.1.2}$R$^{1.3.1.3}$, —NR$^{1.3.1.2}$—C(O)—R$^{1.3.1.3}$, —NR$^{1.3.1.2}$—C(O)—O—R$^{1.3.1.3}$, —SO$_2$—NR$^{1.3.1.2}$R$^{1.3.1.3}$, —NR$^{1.3.1.2}$—SO$_2$—R$^{1.3.1.3}$, —S(O)$_m$—R$^{1.3.1.2}$, —CN, —NR$^{1.3.1.2}$R$^{1.3.1.3}$, —NR$^{1.3.1.1}$—C(O)—NR$^{1.3.1.2}$R$^{1.3.1.3}$, —O—C(O)—R$^{1.3.1.1}$ or
  (c) a $C_{1-3}$-alkyl or $C_{1-3}$-alkyl-O— group wherein each methylene group is substituted by up to two fluorine atoms and each methyl group is substituted by up to three fluorine atoms,
  (d) an aryl group substituted by 1, 2 or 3 substituents R$^{1.3.1.1}$, wherein the substituents R$^{1.3.1.1}$ may be identical or different,
  (e) a heteroaryl group substituted by 1, 2 or 3 substituents R$^{1.3.1.1}$, wherein the substituents R$^{1.3.1.1}$ may be identical or different,
  (f) a heterocyclic group substituted by 1, 2 or 3 substituents R$^{1.3.1.1}$, wherein the substituents R$^{1.3.1.1}$ may be identical or different,
$R^{1.3.2}$ denotes
  (a) halogen, $C_{1-6}$-alkyl, $C_{3-6}$-cycloalkyl,
  (b) —O—R$^{1.3.2.1}$, —O—(CH$_2$)$_s$—O—R$^{1.3.2.1}$, —CO$_2$R$^{1.3.2.1}$, —C(O)—NR$^{1.3.2.2}$R$^{1.3.2.3}$, —O—(CO)—NR$^{1.3.2.2}$R$^{1.3.2.3}$, —N(R$^{1.3.2.1}$)—C(O)—NR$^{1.3.2.2}$R$^{1.3.2.3}$, —N(R$^{1.3.2.2}$)—C(O)—R$^{1.3.2.3}$, —N(R$^{1.3.2.2}$)—C(O)—O—R$^{1.3.2.3}$, —SO$_2$—NR$^{1.3.2.2}$R$^{1.3.2.3}$, —N(R$^{1.3.2.2}$)—SO$_2$—R$^{1.3.2.3}$, —S(O)$_m$—R$^{1.3.2.2}$, —CN, —NR$^{1.3.2.2}$R$^{1.3.2.3}$, —N(R$^{1.3.2.1}$)—C(O)—NR$^{1.3.2.2}$R$^{1.3.2.3}$, —O—C(O)—R$^{1.3.2.1}$ or (c) a $C_{1-3}$-alkyl group wherein each methylene group is substituted by up to two fluorine atoms and each methyl group is substituted by up to three fluorine atoms, $R^{1.3.1.1}$ denotes
  (a) H,
  (b) $C_{1-6}$-alkyl, $C_{3-6}$-cycloalkyl, aryl, heteroaryl, benzyl which may be substituted by a group $R^{1.3.1.1.1}$, or
  (c) a $C_{1-3}$-alkyl group wherein each methylene group is substituted by up to two fluorine atoms and each methyl group is substituted by up to three fluorine atoms, $R^{1.3.1.1.1}$ denotes halogen, HO— or $C_{1-6}$-alkyl-O—, $R^{1.3.1.2}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, $R^{1.3.1.3}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or $R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$ or fluorine, wherein the substituents $R^{1.3.1.1}$ are independent of one another, $R^{1.3.2.1}$ denotes
  (a) H,
  (b) $C_{1-6}$-alkyl, $C_{3-6}$-cycloalkyl, aryl, heteroaryl, benzyl which may be substituted by a group $R^{1.3.2.1.1}$, or
  (c) a $C_{1-3}$-alkyl group wherein each methylene group is substituted by up to two fluorine atoms and each methyl group is substituted by up to three fluorine atoms, $R^{1.3.2.1.1}$ denotes halogen, HO— or $C_{1-6}$-alkyl-O—, $R^{1.3.2.2}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, $R^{1.3.2.3}$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or $R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$ or fluorine, wherein the substituents $R^{1.3.2.1}$ are independent of one another, m denotes one of the numbers 0, 1 or 2,
s denotes one of the numbers 1, 2 or 3,
or a tautomer or salt thereof.

3. A compound of the formula Ia or Ib according to claim 1, wherein
$R^1$ denotes a group of the formula wherein
Q-T denotes $C(R^{1.3})_2$—$C(R^{1.3})_2$, $C(R^{1.3})$=$C(R^{1.3})$, N=$C(R^{1.3})$, $C(R^{1.3})_2$—C(=O), C(=O)—$C(R^{1.3})_2$, $C(R^{1.3})_2$—$S(O)_m$ or $C(R^{1.3})_2$—$N(R^{1.3})$, while in a group $C(R^{1.3})_2$—$C(R^{1.3})_2$, $C(R^{1.3})$=$C(R^{1.3})$ or $C(R^{1.3})_2$—$N(R^{1.3})$ contained in Q-T in each case a group $R^{1.3}$ together with an adjacent group $R^{1.3}$ and the atoms to which these groups are bound may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-S-oxide, thiomorpholinyl-S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another denote by 1, 2 or 3 substituents $R^{1.3.1}$, $R^{1.1}$ denotes
  (a) H,
  (b) $C_{1-6}$-alkyl, —CN, —OH, —O—$C_{1-3}$-alkyl, or
  (c) a $C_{1-3}$-alkyl- or $C_{1-3}$-alkyl-O— group wherein each methylene group is substituted by up to two fluorine atoms and each methyl group is substituted by up to three fluorine atoms, $R^{1.3}$ independently of one another denote
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents $R^{1.3.2}$, wherein the substituents $R^{1.3.2}$ may be identical or different,
  (c) a heteroaryl group optionally substituted by 1, 2 or 3 substituents $R^{1.3.2}$, wherein the substituents $R^{1.3.2}$ may be identical or different, or
  (d) a heterocyclic group optionally substituted by 1, 2 or 3 substituents $R^{1.3.2}$, wherein the substituents $R^{1.3.2}$ may be identical or different, $R^{1.3.1}$ denotes
(a) H, halogen, $C_{1-6}$-alkyl, $C_{3-6}$-cycloalkyl,
(b) —O—$R^{1.3.1.1}$, —O—$C_{1-6}$-alkylene-$NR^{1.3.1.2}R^{1.3.1.3}$, —$CO_2$—$R^{1.3.1.1}$, —C(O)—$NR^{1.3.1.2}R^{1.3.1.3}$, —$SO_2$—$NR^{1.3.1.2}R^{1.3.1.3}$, —$NR^{1.3.1.2}$—$SO_2$—$R^{1.3.1.3}$, —$S(O)_m$—$R^{1.3.1.2}$, —CN, —$NR^{1.3.1.2}R^{1.3.1.3}$, —O—C(O)—$R^{1.3.1.1}$, or
(c) a $C_{1-3}$-alkyl or $C_{1-3}$-alkyl-O— group wherein each methylene group is substituted by up to two fluorine atoms and each methyl group is substituted by up to three fluorine atoms, $R^{1.3.2}$ denotes
(a) halogen, $C_{1-6}$-alkyl, $C_{3-6}$-cycloalkyl,
(b) —O—$R^{1.3.2.1}$, —O—$(CH_2)_s$—O—$R^{1.3.2.1}$, —$CO_2R^{1.3.2.1}$, —$S(O)_m$—$R^{1.3.2.2}$, —CN, —O—C(O)—$R^{1.3.2.1}$ or
(c) a $C_{1-3}$-alkyl group wherein each methylene group is substituted by up to two fluorine atoms and each methyl group is substituted by up to three fluorine atoms, $R^{1.3.1.1}$ denotes
(a) H,
(b) $C_{1-6}$-alkyl, $C_{3-6}$-cycloalkyl, aryl, heteroaryl, benzyl which may be substituted by a group $R^{1.3.1.1.1}$, or
(c) a $C_{1-3}$-alkyl group wherein each methylene group is substituted by up to two fluorine atoms and each methyl group is substituted by up to three fluorine atoms, $R^{1.3.1.1.1}$ denotes halogen, HO— or $C_{1-6}$-alkyl-O—, $R^{1.3.1.2}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^{1.3.1.3}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$, wherein the substituents $R^{1.3.1.1}$ are independent of one another, $R^{1.3.2.1}$ denotes
(a) H,
(b) $C_{1-6}$-alkyl, $C_{3-6}$-cycloalkyl, aryl, heteroaryl, benzyl which may be substituted by a group $R^{1.3.2.1.1}$, or
(c) a $C_{1-3}$-alkyl group wherein each methylene group is substituted by up to two fluorine atoms and each methyl group is substituted by up to three fluorine atoms, $R^{1.3.2.1.1}$ denotes halogen, HO— or $C_{1-6}$-alkyl-O—, $R^{1.3.2.2}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^{1.3.2.3}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$, wherein the substituents $R^{1.3.2.1}$ are independent of one another, m denotes one of the numbers 0, 1 or 2 and
s denotes one of the numbers 1, 2 or 3,
or a tautomer or salt thereof.

4. A compound of the formula Ia or Ib according to claim 1, wherein
$R^1$ denotes a group of the formula

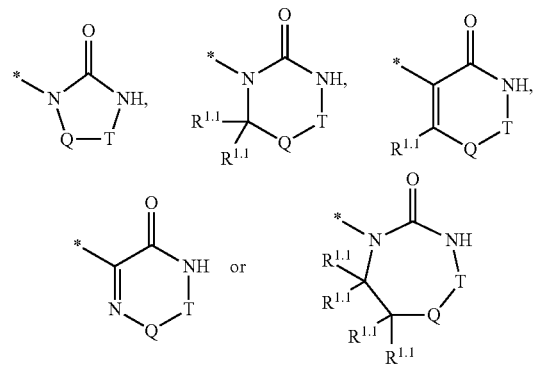

wherein
Q-T denotes $C(R^{1.3})_2$—$C(R^{1.3})_2$, $C(R^{1.3})$=$C(R^{1.3})$, N=$C(R^{1.3})$, $C(R^{1.3})_2$—C(=O), C(=O)—$C(R^{1.3})_2$, $C(R^{1.3})_2$—$S(O)_m$ or $C(R^{1.3})_2$—$N(R^{1.3})$, while in a group $C(R^{1.3})_2$—$C(R^{1.3})_2$, $C(R^{1.3})$=$C(R^{1.3})$ or $C(R^{1.3})_2$—$N(R^{1.3})$ contained in Q-T in each case a group $R^{1.3}$ together with an adjacent group $R^{1.3}$ and the atoms to which these groups are bound may also denote a group selected from cyclopentyl, cyclohexyl, cyclopentenyl, cyclohexenyl, dioxanyl, phenyl, naphthyl, thienyl, pyridyl, pyrazinyl, pyridazinyl, quinolinyl, isoquinolinyl, morpholinyl, pyrrolidinyl, piperidinyl, tetrahydrofuranyl, tetrahydropyranyl and piperazinyl, which may be substituted independently of one another denote by 1, 2 or 3 substituents $R^{1.3.1}$, $R^{1.1}$ denotes
(a) H,
(b) $C_{1-6}$-alkyl, —CN, —OH, —O—$C_{1-3}$-alkyl, or
(c) a $C_{1-3}$-alkyl- or $C_{1-3}$-alkyl-O— group wherein each methylene group is substituted by up to two fluorine atoms and each methyl group is substituted by up to three fluorine atoms, $R^{1.3}$ denotes
(a) H, $C_{1-6}$-alkyl, $C_{3-6}$-cycloalkyl,
(b) an aryl group optionally substituted by 1, 2 or 3 substituents $R^{1.3.2}$, wherein the substituents $R^{1.3.2}$ may be identical or different,
(c) a heteroaryl group optionally substituted by 1, 2 or 3 substituents $R^{1.3.2}$, wherein the substituents $R^{1.3.2}$ may be identical or different, or
(d) a heterocyclic group optionally substituted by 1, 2 or 3 substituents $R^{1.3.2}$, wherein the substituents $R^{1.3.2}$ may be identical or different, $R^{1.3.1}$ denotes
(a) H, halogen, $C_{1-6}$-alkyl, $C_{3-6}$-cycloalkyl,
(b) —O—$R^{1.3.1.1}$, —O—$C_{1-6}$-alkylene-$NR^{1.3.1.2}R^{1.3.1.3}$, —$CO_2$—$R^{1.3.1.1}$, —C(O)—$NR^{1.3.1.2}R^{1.3.1.3}$, —$SO_2$—$NR^{1.3.1.2}R^{1.3.1.3}$, —$NR^{1.3.1.2}$—$SO_2$—$R^{1.3.1.3}$, —S(O)$_m$—$R^{1.3.1.2}$, —CN, —$NR^{1.3.1.2}R^{1.3.1.3}$, —O—C(O)—$R^{1.3.1.1}$, or
(c) a $C_{1-3}$-alkyl group wherein each methylene group is substituted by up to two fluorine atoms and each methyl group is substituted by up to three fluorine atoms, $R^{1.3.2}$ denotes
(a) halogen, $C_{1-6}$-alkyl, $C_{3-6}$-cycloalkyl,
(b) —O—$R^{1.3.2.1}$, —O—$(CH_2)_s$—$OR^{1.3.2.1}$, —$CO_2R^{1.3.2.1}$, —S(O)$_m$—$R^{1.3.2.2}$, —CN, —O—C(O)—$R^{1.3.2.1}$ or
(c) a $C_{1-3}$-alkyl group wherein each methylene group is substituted by up to two fluorine atoms and each methyl group is substituted by up to three fluorine atoms, $R^{1.3.1.1}$ denotes
(a) H,
(b) $C_{1-6}$-alkyl, $C_{3-6}$-cycloalkyl, aryl, heteroaryl, benzyl which may be substituted by a group $R^{1.3.1.1.1}$, or
(c) a $C_{1-3}$-alkyl group wherein each methylene group is substituted by up to two fluorine atoms and each methyl group is substituted by up to three fluorine atoms, $R^{1.3.1.1.1}$ denotes halogen, HO— or $C_{1-6}$-alkyl-O—,
$R^{1.3.1.2}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^{1.3.1.3}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.1.2}$ and $R^{1.3.1.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.1.1}$, wherein the substituents $R^{1.3.1.1}$ are independent of one another, $R^{1.3.2.1}$ denotes
(a) H,
(b) $C_{1-6}$-alkyl, $C_{3-6}$-cycloalkyl, aryl, heteroaryl, benzyl which may be substituted by a group $R^{1.3.2.1.1}$, or
(c) a $C_{1-3}$-alkyl group wherein each methylene group is substituted by up to two fluorine atoms and each methyl group is substituted by up to three fluorine atoms, $R^{1.3.2.1.1}$ denotes halogen, HO— or $C_{1-6}$-alkyl-O—,
$R^{1.3.2.2}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^{1.3.2.3}$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by 1, 2 or 3 substituents $R^{1.3.2.1}$, wherein the substituents $R^{1.3.2.1}$ are independent of one another, m denotes one of the numbers 0, 1 or 2 and
s denotes one of the numbers 1, 2 or 3,
or a tautomer or salt thereof.

5. A compound of the formula Ia or Ib according to claim 1, wherein
$R^1$ denotes a group of the formula

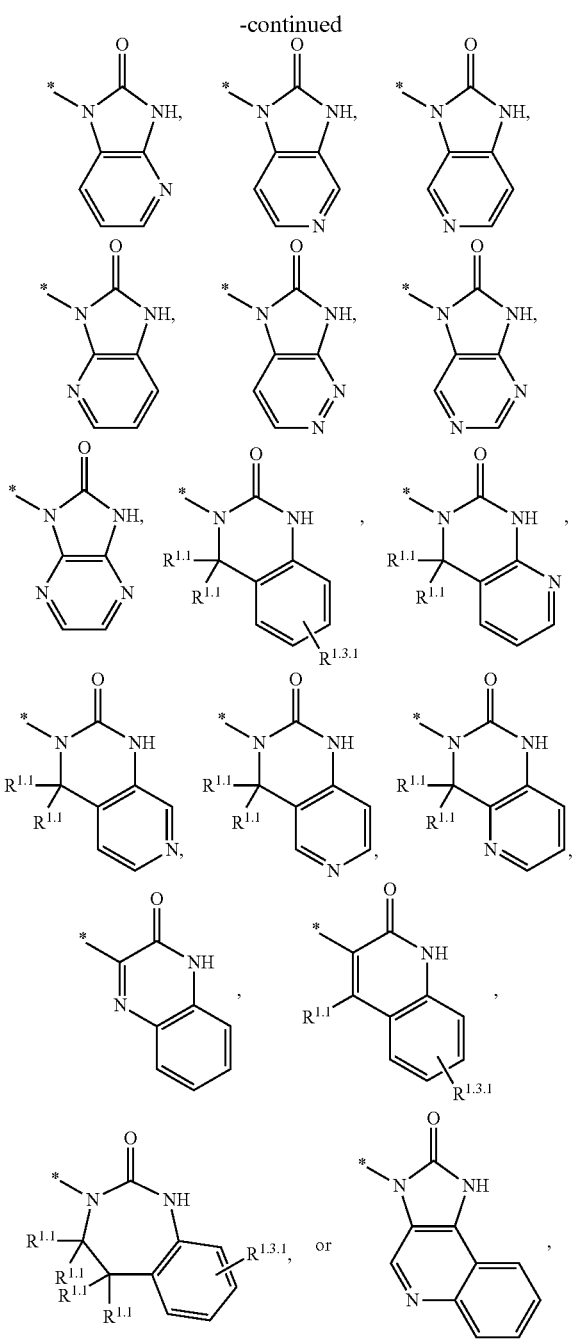

wherein
R$^{1.1}$ denotes
  (a) H,
  (b) C$_{1-3}$-alkyl, —OH, —O—C$_{1-3}$-alkyl, or
  (c) a C$_{1-3}$-alkyl- or C$_{1-3}$-alkyl-O— group wherein each methylene group is substituted by up to two fluorine atoms and each methyl group is substituted by up to three fluorine atoms,
R$^{1.3}$ independently of one another denote
  (a) H, C$_{1-6}$-alkyl, C$_{3-6}$-cycloalkyl,
  (b) a phenyl group optionally substituted by 1, 2 or 3 substituents R$^{1.3.2}$, wherein the substituents R$^{1.3.2}$ may be identical or different,
  (c) a heteroaryl group optionally substituted by 1, 2 or 3 substituents R$^{1.3.2}$ which is selected from among ben-zimidazole, benzothiophene, furan, imidazole, indole, isoxazole, oxazole, pyrazine, pyrazole, pyridazine, pyridine, pyrimidine, pyrrole, thiazole, thiophene and triazole, wherein the substituents R$^{1.3.2}$ may be identical or different, or
  (d) a heterocyclic group optionally substituted by 1, 2 or 3 substituents R$^{1.3.2}$, wherein the substituents R$^{1.3.2}$ may be identical or different,
R$^{1.3.1}$ denotes
  (a) H, halogen, C$_{1-6}$-alkyl, C$_{3-6}$-cycloalkyl,
  (b) —O—R$^{1.3.1.1}$, —O—C$_{1-6}$-alkylene-NR$^{1.3.1.2}$R$^{1.3.1.3}$, —CO$_2$R$^{1.3.1.1}$, —C(O)—NR$^{1.3.1.2}$R$^{1.3.1.3}$, —SO$_2$—NR$^{1.3.1.2}$R$^{1.3.1.3}$, —NR$^{1.3.1.2}$—SO$_2$—R$^{1.3.1.3}$, —S(O)$_m$—R$^{1.3.1.2}$, —CN, —NR$^{1.3.1.2}$R$^{1.3.1.3}$, —O—C(O)—R$^{1.3.1.1}$ or
  (c) a C$_{1-3}$-alkyl or C$_{1-3}$-alkyl-O— group wherein each methylene group is substituted by up to two fluorine atoms and each methyl group is substituted by up to three fluorine atoms,
R$^{1.3.2}$ denotes
  (a) halogen, C$_{1-6}$-alkyl, C$_{3-6}$-cycloalkyl,
  (b) —O—R$^{1.3.2.1}$, —O—(CH$_2$)$_s$—O—R$^{1.3.2.1}$, —CO$_2$R$^{1.3.2.1}$, —S(O)$_m$—R$^{1.3.2.2}$, —CN, —O—C(O)—R$^{1.3.2.1}$ or
  (c) a C$_{1-3}$-alkyl group wherein each methylene group is substituted by up to two fluorine atoms and each methyl group is substituted by up to three fluorine atoms,
R$^{1.3.1.1}$ denotes
  (a) H,
  (b) C$_{1-6}$-alkyl, C$_{3-6}$-cycloalkyl, aryl, heteroaryl, benzyl which may be substituted by a group R$^{1.3.1.1.1}$, or
  (c) a C$_{1-3}$-alkyl group wherein each methylene group is substituted by up to two fluorine atoms and each methyl group is substituted by up to three fluorine atoms,
R$^{1.3.1.1.1}$ denotes HO— or C$_{1-6}$-alkyl-O—,
R$^{1.3.1.2}$ denotes
  (a) H, or
  (b) C$_{1-3}$-alkyl, phenyl or benzyl, wherein the groups may be unsubstituted or substituted by halogen, HO— or H$_3$C—O—,
R$^{1.3.1.3}$ denotes
  (a) H, or
  (b) C$_{1-3}$-alkyl, phenyl or benzyl, wherein the groups may be unsubstituted or substituted by halogen, HO— or H$_3$C—O—, or
R$^{1.3.1.2}$ and R$^{1.3.1.3}$ together may also form a ring which is selected from among azetidinyl, pyrrolidinyl, piperidinyl, piperazinyl and morpholinyl, wherein the ring may be unsubstituted or substituted by a substituent R$^{1.3.1.1}$,
R$^{1.3.2.1}$ denotes
  (a) H,
  (b) C$_{1-6}$-alkyl, C$_{3-6}$-cycloalkyl, aryl, heteroaryl, benzyl which may be substituted by a group R$^{1.3.2.1.1}$, or
  (c) a C$_{1-3}$-alkyl group wherein each methylene group is substituted by up to two fluorine atoms and each methyl group is substituted by up to three fluorine atoms,
R$^{1.3.2.1.1}$ denotes HO— or C$_{1-6}$-alkyl-O—,
R$^{1.3.2.2}$ denotes
  (a) H, or
  (b) C$_{1-3}$-alkyl, phenyl or benzyl, wherein the groups may be unsubstituted or substituted by halogen, HO— or H$_3$C—O—, $R^{1.3.2.3}$ denotes
  (a) H, or
  (b) $C_{1-3}$-alkyl, phenyl or benzyl, wherein the groups may be unsubstituted or substituted by halogen, HO— or $H_3C$—O—, or
$R^{1.3.2.2}$ and $R^{1.3.2.3}$ together may also form a ring which is selected from among azetidinyl, pyrrolidinyl, piperidinyl, piperazinyl and morpholinyl, wherein the ring may be unsubstituted or substituted by a substituent $R^{1.3.2.1}$,
m denotes one of the numbers 0, 1 or 2, and
s denotes one of the numbers 1, 2 or 3,
or a tautomer or salt thereof.

6. A compound of the formula Ia or Ib according to claim 1, wherein
$R^1$ denotes

[chemical structures]

or a tautomer or salt thereof.

7. A compound of the formula Ia or Ib according to claim 1, wherein denotes a hydrogen atom,
or a tautomer or salt thereof.

8. A compound of the formula Ia or Ib according to claim 1, wherein
$R^3$ denotes
  (a) H,
  (b) $C_{1-6}$-alkyl,
  (c) a $C_{3-6}$-cycloalkyl group substituted by one or two groups $R^{3.2}$, or
  (d) a $C_{1-3}$-alkyl group wherein each methylene group is substituted by up to two fluorine atoms and each methyl group is substituted by up to three fluorine atoms,
$R^{3.2}$ independently of one another denote
  (a) H,
  (b) halogen, $C_{1-3}$-alkyl, —OH, —O—$C_{1-3}$-alkyl, or
  (c) a $C_{1-3}$-alkyl- or —O—$C_{1-3}$-alkyl group wherein each methylene group is substituted by up to two fluorine atoms and each methyl group is substituted by up to three fluorine atoms, $R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) an aryl group substituted by one or two groups $R^{4.2}$,
  (f) a $C_{5-7}$-cycloalkyl group which may be fused to an aryl or heteroaryl group, while the resultant bicyclic group is additionally substituted by one or two groups $R^{4.2}$, or
  (g) a heteroaryl group substituted by one or two groups $R^{4.2}$,
$R^{4.1}$ denotes
  (a) H,
  (b) a phenyl group substituted by the groups $R^{4.1.1}$ and $R^{4.1.2}$, or
  (c) a heteroaryl group substituted by the groups $R^{4.1.1}$ and $R^{4.1.2}$,
$R^{4.1.1}$ denotes
  (a) H,
  (c) halogen, $C_{1-3}$-alkyl, —OH, —CN, —O—$C_{1-3}$-alkyl, —$NR^{4.1.1.1}R^{4.1.1.2}$, —S—$C_{1-3}$-alkyl, —$NR^{4.1.1.1}$—C(O)—$C_{1-3}$-alkyl, —C(O)—$NR^{4.1.1.1}R^{4.1.1.2}$, —C(O)—O—$R^{4.1.1.3}$, or
  (d) a $C_{1-3}$-alkyl or —O—$C_{1-3}$-alkyl group wherein each methylene group is substituted by up to two fluorine atoms and each methyl group is substituted by up to three fluorine atoms,
$R^{4.1.1.1.1}$ denotes H, or $C_{1-3}$-alkyl,
$R^{4.1.1.2}$ denotes H, or $C_{1-3}$-alkyl, or
$R^{4.1.1.1}$ and $R^{4.1.1.2}$ together with the nitrogen atom to which they are bound also denote a group selected from morpholinyl, thiomorpholinyl, piperidinyl, piperazinyl, pyrrolidinyl and azetidinyl,
$R^{4.1.1.3}$ denotes H, or $C_{1-3}$-alkyl,
$R^{4.1.2}$ denotes
  (a) H,
  (b) halogen, $C_{1-3}$-alkyl, —OH, —O—$C_{1-3}$-alkyl, or
  (c) a $C_{1-3}$-alkyl or —O—$C_{1-3}$-alkyl group wherein each methylene group is substituted by up to two fluorine atoms and each methyl group is substituted by up to three fluorine atoms, or
$R^{4.2}$ independently of one another denote
  (a) H,
  (b) halogen, $C_{1-3}$-alkyl, —OH, —CN, —O—$C_{1-3}$-alkyl, —$NR^{4.2.1}R^{4.2.2}$, —S—$C_{1-3}$-alkyl, —$NR^{4.2.1}$—C(O)—$C_{1-3}$-alkyl, —C(O)—$NR^{4.2.1}R^{4.2.2}$, C(O)—O—$R^{4.2.3}$, or
  (c) a $C_{1-3}$-alkyl or —O—$C_{1-3}$-alkyl group wherein each methylene group is substituted by up to two fluorine atoms and each methyl group is substituted by up to three fluorine atoms,
$R^{4.2.1}$
$R^{4.2.2}$ denotes H, or $C_{1-3}$-alkyl and
$R^{4.2.2}$ denotes H, or $C_{1-3}$-alkyl, or
$R^{4.2.1}$ and $R^{4.2.2}$ together with the nitrogen atom to which they are bound also denote a group which is selected from among morpholinyl, thiomorpholinyl, piperidinyl, piperidonyl, piperazinyl, pyrrolidinyl and azetidinyl, and which may additionally be substituted by one or two groups selected from F, —OH, —O—$C_{1-3}$-alkyl, —$OCF_3$, $C_{1-3}$-alkyl and $CF_3$,
$R^{4.2.3}$ denotes H, or $C_{1-3}$-alkyl,
$R^3$ and $R^4$ together with the nitrogen atom to which they are bound denote:

(a) a saturated 5-, 6- or 7-membered heterocyclic group which is substituted at a carbon atom by a group $R^{4.3}$ or by two groups $R^{4.3}$ and $R^{4.4}$, (b) a saturated 5-, 6- or 7-membered heterocyclic group which is substituted at two adjacent carbon atoms by in each case a group $R^{4.3}$ and $R^{4.4}$, (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$, (d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$, (e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or (f) a heteroaryl group which is substituted at 1, 2 or 3 carbon atoms by a group $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN $R^{4.3.1}$ denotes H, $C_{1-3}$-alkyl-O—C(O)—, —$NH_2$, ($C_{1-4}$-alkyl)-NH—, ($C_{1-4}$-alkyl)$_2$N, or heterocyclyl, $R^{4.4}$ denotes
(a) H, $C_{1-3}$-alkyl, —OH, —O—$C_{1-3}$-alkyl or
(b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl, $C_{5-6}$-cycloalkenyl or heterocyclyl group, $R^{4.5}$ independently of one another denote
(a) H,
(b) halogen, $C_{1-3}$-alkyl, —OH, —O—$C_{1-3}$-alkyl, —$NH_2$, —CN, —C(O)—O—$R^{4.5.1}$, —C(O)—$NR^{4.5.2}R^{4.5.3}$,
(c) a $C_{1-3}$-alkyl- or —O—$C_{1-3}$-alkyl group wherein each methylene group is substituted by up to two fluorine atoms and each methyl group is substituted by up to three fluorine atoms, or
(d) phenyl, $R^{4.5.1}$ denotes H, or $C_{1-3}$-alkyl,
$R^{4.5.2}$ denotes H, or $C_{1-3}$-alkyl and
$R^{4.5.3}$ denotes H, or $C_{1-3}$-alkyl,
or a tautomer or salt thereof.

9. A compound of the formula Ia or Ib according to claim 1, wherein
$R^3$ denotes
(a) H,
(b) $C_{1-6}$-alkyl,
(c) a $C_{3-6}$-cycloalkyl substituted by one or two groups $R^{3.2}$, or
(d) a $C_{1-3}$-alkyl group wherein each methylene group is substituted by up to two fluorine atoms and each methyl group is substituted by up to three fluorine atoms, $R^{3.2}$ independently of one another denote
(a) H,
(b) halogen, $C_{1-3}$-alkyl, —OH, —O—$C_{1-3}$-alkyl, or
(c) a $C_{1-3}$-alkyl or —O—$C_{1-3}$-alkyl group wherein each methylene group is substituted by up to two fluorine atoms and each methyl group is substituted by up to three fluorine atoms, $R^4$ denotes
(a) H,
(b) $C_{1-6}$-alkylene-$R^{4.1}$,
(c) a $C_{3-6}$-cycloalkyl group substituted by one or two groups $R^{4.2}$,
(d) a $C_{5-7}$-cycloalkenyl group substituted by one or two groups $R^{4.2}$,
(e) an aryl group substituted by one or two groups $R^{4.2}$, or
(f) a $C_{5-6}$-cycloalkyl group which may be fused to a phenyl, thiazole or thienyl group, while the resultant bicyclic group is additionally substituted by one or two groups $R^{4.2}$, $R^{4.1}$ denotes
(a) H, or
(b) a phenyl group substituted by the groups $R^{4.1.1}$ and $R^{4.1.2}$, $R^{4.1.1}$ denotes
(a) H,
(b) halogen, $C_{1-3}$-alkyl, —OH, —O—$C_{1-3}$-alkyl, —CN, —C(O)—O—$R^{4.1.1.3}$, or
(c) a $C_{1-3}$-alkyl- or —O—$C_{1-3}$-alkyl group wherein each methylene group is substituted by up to two fluorine atoms and each methyl group is substituted by up to three fluorine atoms, $R^{4.1.1.3}$ denotes H, or $C_{1-3}$-alkyl, $R^{4.1.2}$ denotes
(a) H,
(b) halogen, $C_{1-3}$-alkyl, —OH, —O—$C_{1-3}$-alkyl, or
(c) a $C_{1-3}$-alkyl or —O—$C_{1-3}$-alkyl group wherein each methylene group is substituted by up to two fluorine atoms and each methyl group is substituted by up to three fluorine atoms, or $R^{4.2}$ independently of one another denote
(a) H,
(b) halogen, $C_{1-3}$-alkyl, —OH, —O—$C_{1-3}$-alkyl, —CN, —$NH_2$, —O—C(O)—$C_{1-3}$-alkyl, or
(c) a $C_{1-3}$-alkyl- or —O—$C_{1-3}$-alkyl group wherein each methylene group is substituted by up to two fluorine atoms and each methyl group is substituted by up to three fluorine atoms, $R^3$ and $R^4$ together with the nitrogen atom to which they are bound denote:
(a) a saturated 5- or 6-membered heterocyclic group which is substituted at a carbon atom by a group $R^{4.3}$ or by two groups $R^{4.3}$ and $R^{4.4}$,
(b) a saturated 5- or 6-membered heterocyclic group which is substituted at two adjacent carbon atoms by in each case a group $R^{4.3}$ and $R^{4.4}$,
(c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
(d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
(e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$ and is selected from among

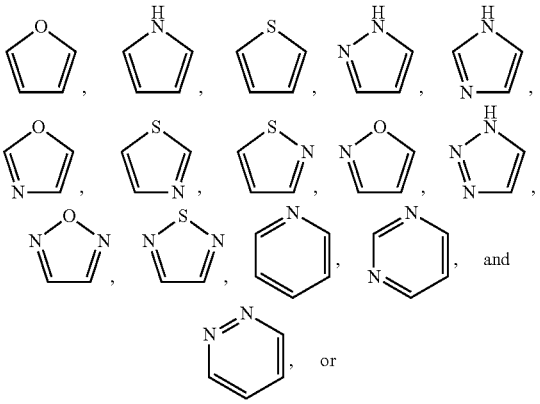

(f) a heteroaryl group which is substituted at 1, 2 or 3 carbon atoms by in each case a group $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN $R^{4.3.1}$ denotes H, $C_{1-3}$-alkyl-O—C(O)—, —$NH_2$, ($C_{1-4}$-alkyl)-NH—, ($C_{1-4}$-alkyl)$_2$N—, morpholinyl, thiomorpholinyl, piperidinyl, pyrrolidinyl, or azetidinyl, $R^{4.4}$ denotes
  (a) H, $C_{1-3}$-alkyl, —OH, —O—$C_{1-3}$-alkyl or
  (b) a $C_{1-3}$-alkyl or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl or heterocyclyl group, and $R^{4.5}$ independently of one another denote
  (a) H,
  (b) halogen, $C_{1-3}$-alkyl, —OH, —O—$C_{1-3}$-alkyl, —$NH_2$, —CN,
  (c) a $C_{1-3}$-alkyl or —O—$C_{1-3}$-alkyl group wherein each methylene group is substituted by up to two fluorine atoms and each methyl group is substituted by up to three fluorine atoms, or
  (d) phenyl, or a tautomer or salt thereof.

10. A compound of the formula Ia or Ib according to claim 1, wherein $R^3$ denotes
  (a) H,
  (b) $C_{1-6}$-alkyl,
  (c) a $C_{3-6}$-cycloalkyl group substituted by one or two groups $R^{3.2}$, or
  (d) a $C_{1-3}$-alkyl group wherein each methylene group is substituted by up to two fluorine atoms and each methyl group is substituted by up to three fluorine atoms, $R^{3.2}$ independently of one another denote
  (a) H,
  (b) halogen, $C_{1-3}$-alkyl, —OH, —O—$C_{1-3}$-alkyl, or
  (c) a $C_{1-3}$-alkyl- or —O—$C_{1-3}$-alkyl group wherein each methylene group is substituted by up to two fluorine atoms and each methyl group is substituted by up to three fluorine atoms, $R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) a phenyl group substituted by one or two groups $R^{4.2}$, or
  (f) a $C_{5-6}$-cycloalkyl group which may be fused to a phenyl, thiazolyl or thienyl group, while the resultant bicyclic group is additionally substituted by one or two groups $R^{4.2}$, $R^{4.1}$ denotes
  (a) H, or
  (b) a phenyl group substituted by the groups $R^{4.1.1}$ and $R^{4.1.2}$, $R^{4.1.1}$ denotes
  (a) H,
  (b) halogen, $C_{1-3}$-alkyl, —OH, —O—$C_{1-3}$-alkyl, —CN, —C(O)—O—$R^{4.1.1.3}$, or
  (c) a $C_{1-3}$-alkyl- or —O—$C_{1-3}$-alkyl group wherein each methylene group is substituted by up to two fluorine atoms and each methyl group is substituted by up to three fluorine atoms, $R^{4.1.1.3}$ denotes H, or $C_{1-3}$-alkyl, $R^{4.1.2}$ denotes
  (a) H,
  (b) halogen, $C_{1-3}$-alkyl, —OH, —O—$C_{1-3}$-alkyl, or
  (c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ denotes
  (a) H,
  (b) halogen, $C_{1-3}$-alkyl, —OH, —O—$C_{1-3}$-alkyl, —CN, —$NH_2$, or
  (c) a $C_{1-3}$-alkyl- or —O—$C_{1-3}$-alkyl group wherein each methylene group is substituted by up to two fluorine atoms and each methyl group is substituted by up to three fluorine atoms, or $R^3$ and $R^4$ together with the nitrogen atom to which they are bound denote:
  (a) a saturated 5- or 6-membered heterocyclic group which is selected from among piperidinyl, piperidinonyl, morpholinyl, thiomorpholinyl, piperazinyl, pyrrolidinyl and pyrrolidinonyl, and which is substituted at a carbon atom by a group $R^{4.3}$ or by two groups $R^{4.3}$ and $R^{4.4}$,
  (b) a saturated 5- or 6-membered heterocyclic group which is selected from among piperidinyl, piperidinonyl, morpholinyl, thiomorpholinyl, piperazinyl, pyrrolidinyl and pyrrolidinonyl, and which is substituted at two adjacent carbon atoms by in each case a group $R^{4.3}$ and $R^{4.4}$,
  (c) a saturated 5-, 6- or 7-membered heterocyclic group which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, and which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, while the fused-on cycloalkyl or heterocyclyl group is substituted by 1, 2 or 3 groups $R^{4.5}$, (d) a monounsaturated 5-, 6- or 7-membered heterocyclic group which is selected from among

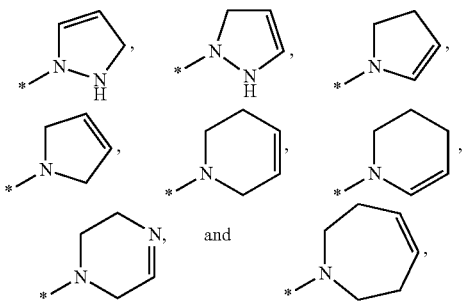

and which is substituted at a carbon atom by a group $R^{4.3}$ or by two groups $R^{4.3}$ and $R^{4.4}$ and is additionally fused to a phenyl group, wherein the fused-on phenyl group is substituted by 1, 2 or 3 groups $R^{4.5}$, (e) a monounsaturated 5-, 6- or 7-membered heterocyclic group which is selected from among

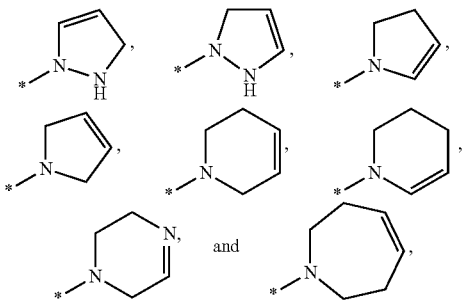

and which is substituted at a carbon atom by a group $R^{4.3}$ or by two groups $R^{4.3}$ and $R^{4.4}$ and is additionally fused to a 5- or 6-membered heteroaryl group, wherein the fused-on heteroaryl group is substituted by 1, 2 or 3 groups $R^{4.5}$ and is selected from among

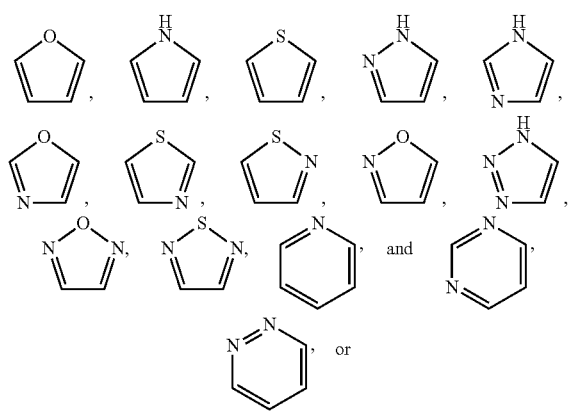

(f) a heteroaryl group which is selected from among indole, isoindole, azaindole, indazole and benzimidazole, and which is substituted at 1, 2 or 3 carbon atoms by a group $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN, $R^{4.3.1}$ denotes H, $C_{1-3}$-alkyl-O—C(O), —$NH_2$, ($C_{1-4}$-alkyl)-NH, ($C_{i-}$4-alkyl)$_2$N, morpholinyl, thiomorpholinyl, piperidinyl, pyrrolidinyl, or azetidinyl, $R^{4.4}$ denotes (a) H, $C_{1-3}$-alkyl, —OH, —O—$C_{1-3}$-alkyl or (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl group or a heterocyclyl group which is selected from among azetidinyl, pyrrolidinyl, piperidinyl and azepanyl, and $R^{4.5}$ independently of one another denote (a) H, (b) halogen, $C_{1-3}$-alkyl, —OH, —O—$C_{1-3}$-alkyl, —$NH_2$, —CN, (c) a $C_{1-3}$-alkyl- or —O—$C_{1-3}$-alkyl group wherein each methylene group is substituted by up to two fluorine atoms and each methyl group is substituted by up to three fluorine atoms, or (d) phenyl, or a tautomer or salt thereof.

11. A compound of the formula Ia or Ib according to claim 1, wherein $R^3$ denotes (a) H, (b) $C_{1-3}$-alkyl, or (c) a $C_{1-3}$-alkyl group wherein each methylene group is substituted by up to two fluorine atoms and each methyl group is substituted by up to three fluorine atoms, and $R^4$ denotes H or a group selected from

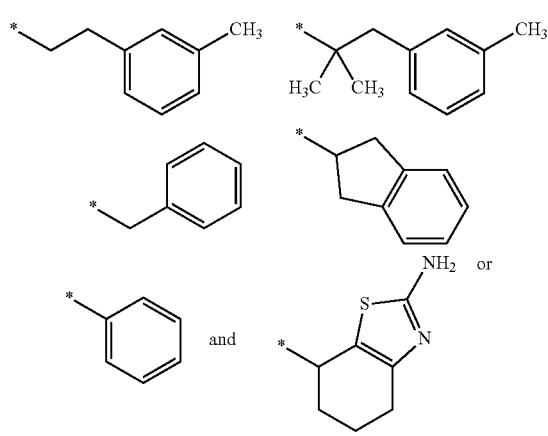

$R^3$ and $R^4$ together with the nitrogen atom to which they are bound denote a group selected from
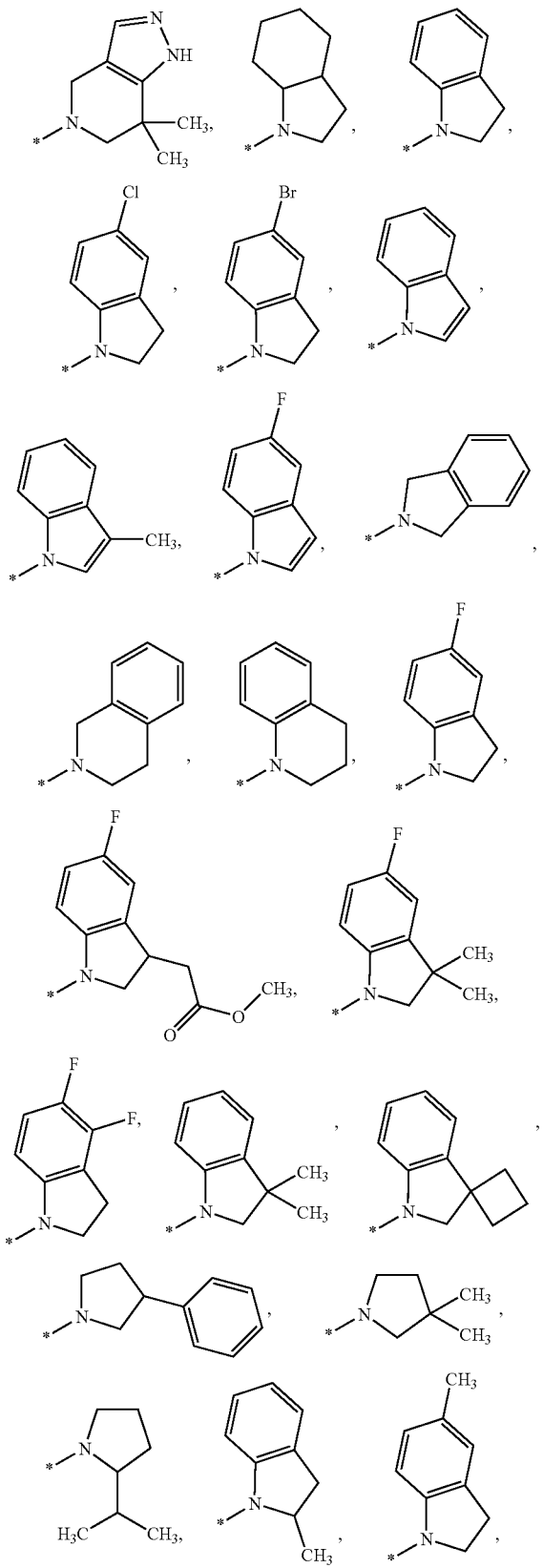
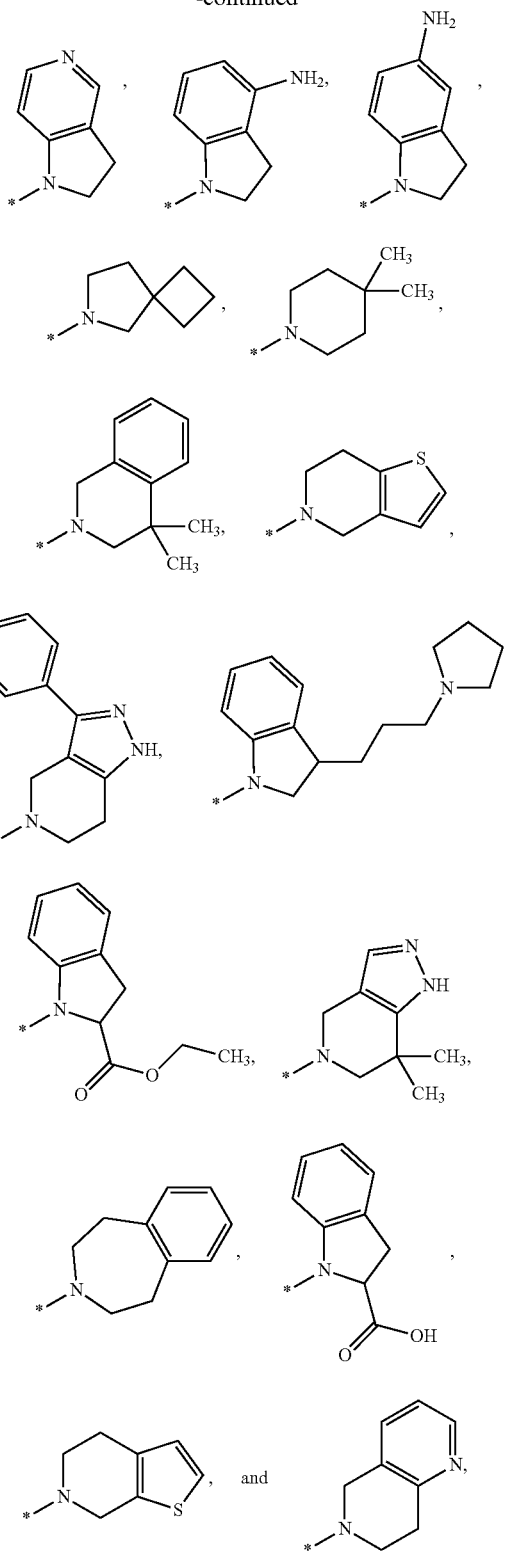
or a tautomer or salt thereof.
12. A compound of the formula Ia or Ib according to claim 1, wherein
$R^5$ denotes H or $C_{1-3}$-alkyl,
or a tautomer or salt thereof.

13. A compound of the formula Ia or Ib according to claim 1, wherein $R^1$ denotes a group selected from

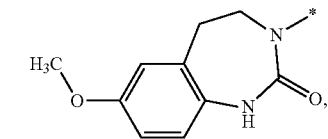 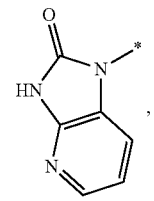

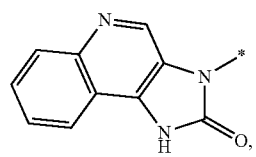 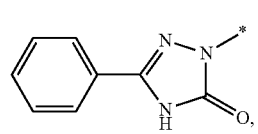

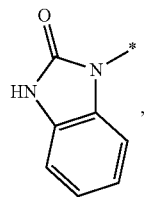 , 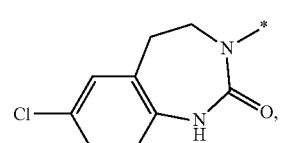 and

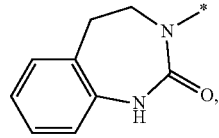

$R^2$ denotes H, $R^3$ denotes
  (a) H,
  (b) $C_{1-3}$-alkyl, or
  (c) a $C_{1-3}$-alkyl group wherein each methylene group is substituted by up to two fluorine atoms and each methyl group is substituted by up to three fluorine atoms, and $R^4$ denotes H or a group selected from

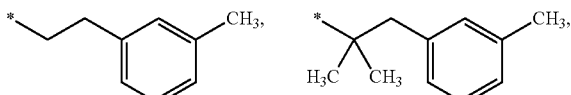

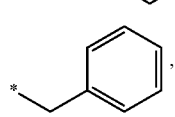 , 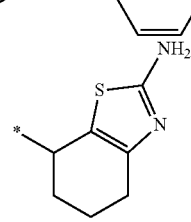 , 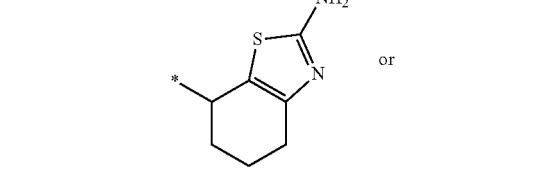 or $R^3$ and $R^4$ together with the nitrogen atom to which they are bound denote a group selected from

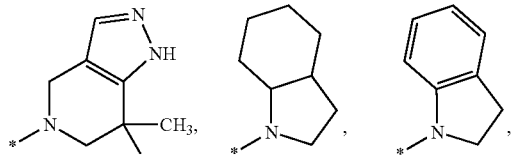

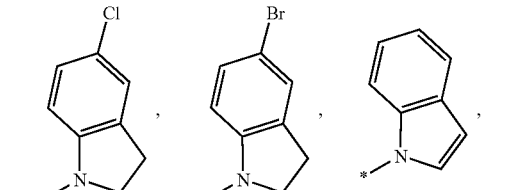

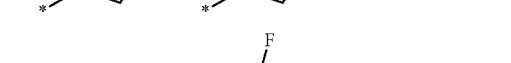

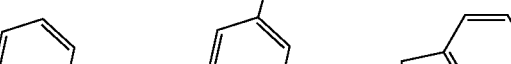

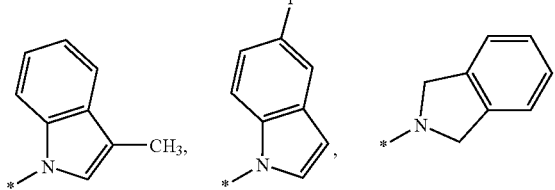

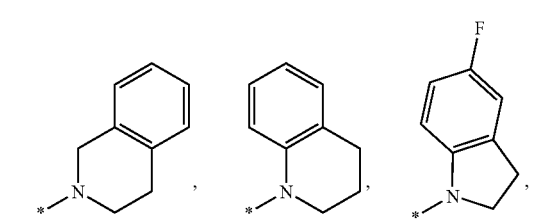

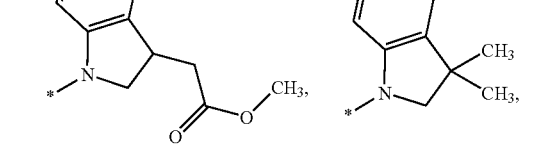

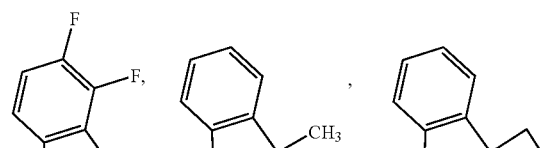

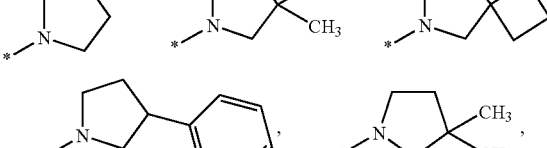

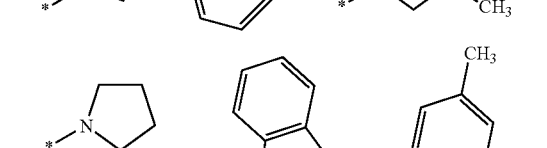

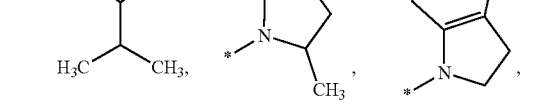

105
-continued
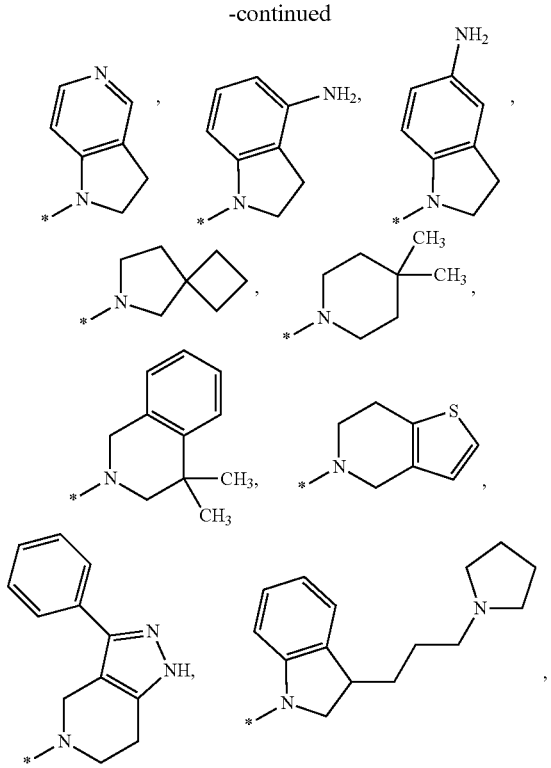
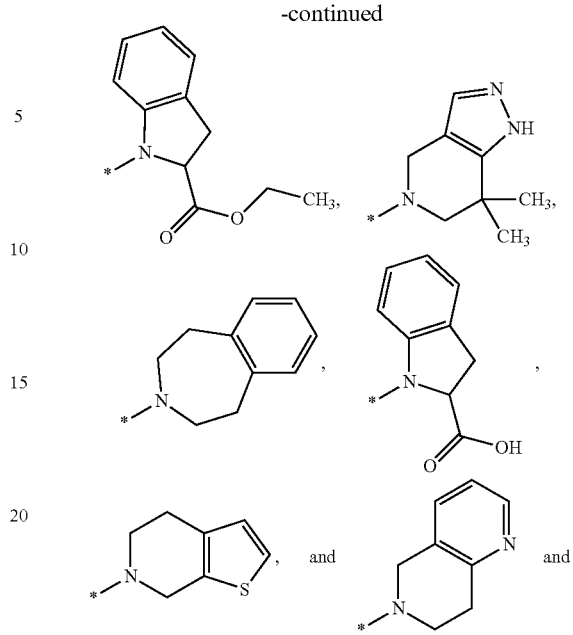
106
-continued
$R^5$ denotes H or $C_{1-3}$-alkyl,
or a tautomer or salt thereof.
14. A compound of the formula Ia or Ib according to claim 1 selected from the group consisting of:
| No. | Structure |
|---|---|
| (1) | <br> |
| (2) | <br> |

-continued
| No. | Structure |
|---|---|
| (3) | 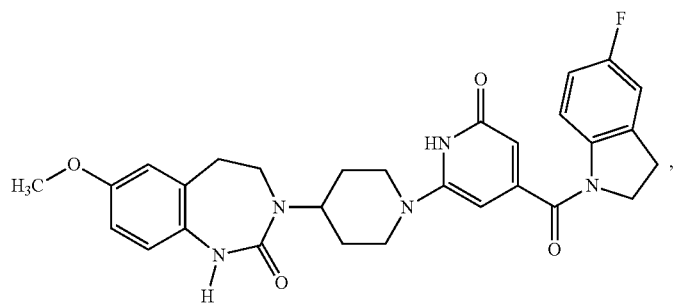 |
| (4) | 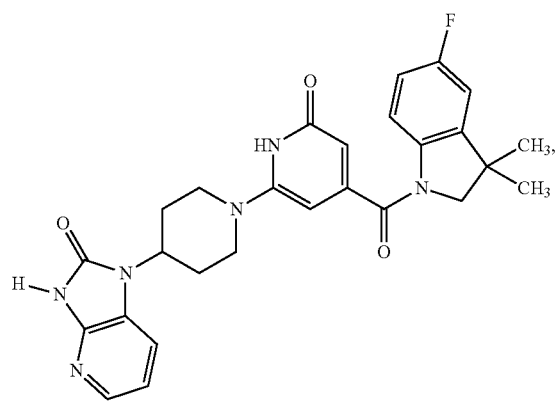 |
| (5) | 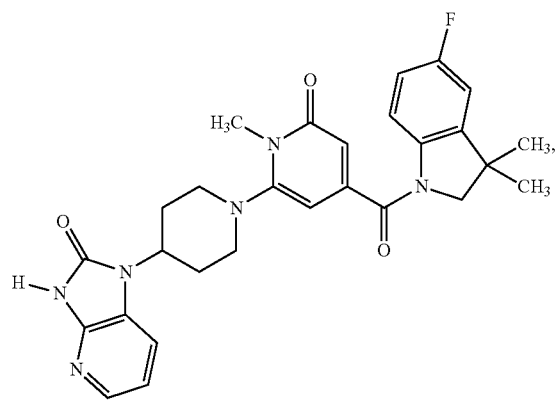 |
| (6) | 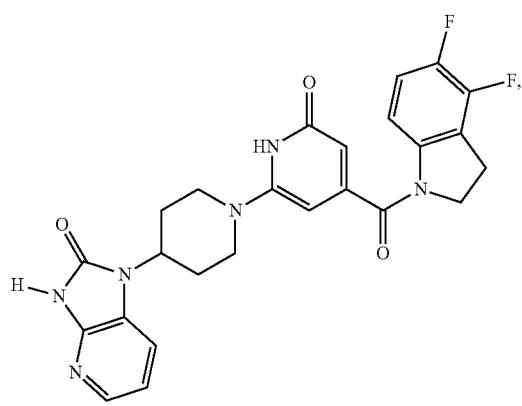 |

| No. | Structure |
|---|---|
| (7) | 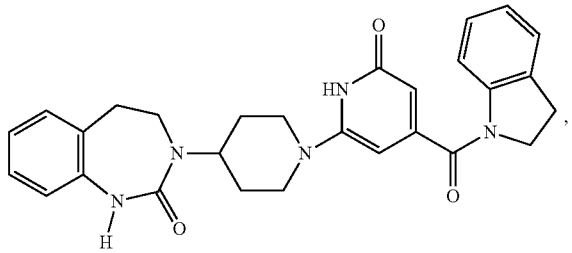 |
| (8) | 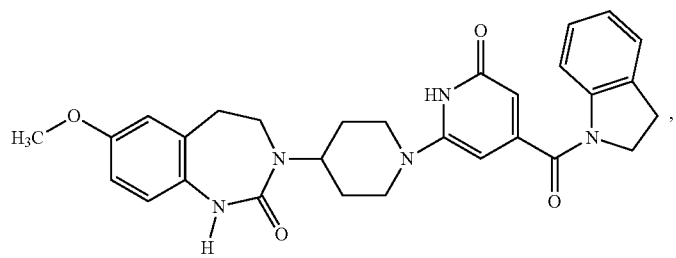 |
| (9) | 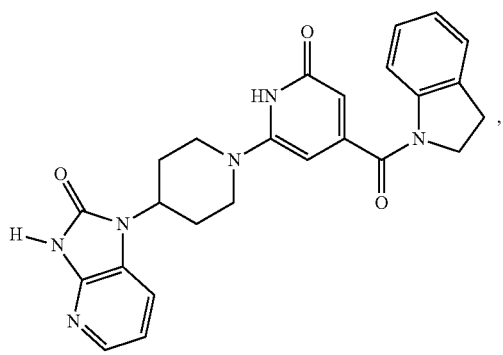 |
| (10) | 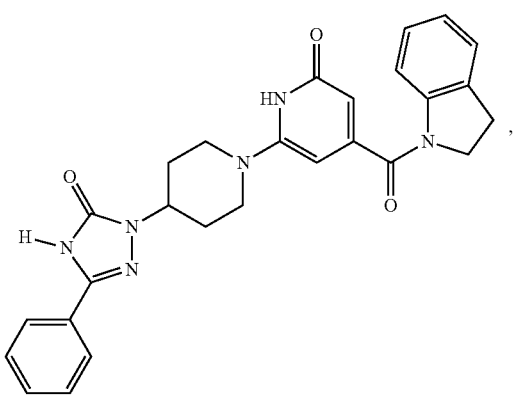 |
| (11) | 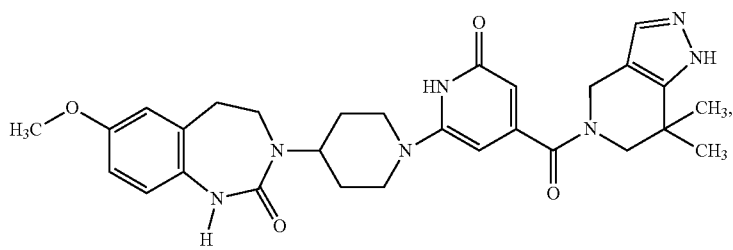 |

| No. | Structure |
|---|---|
| (12) | 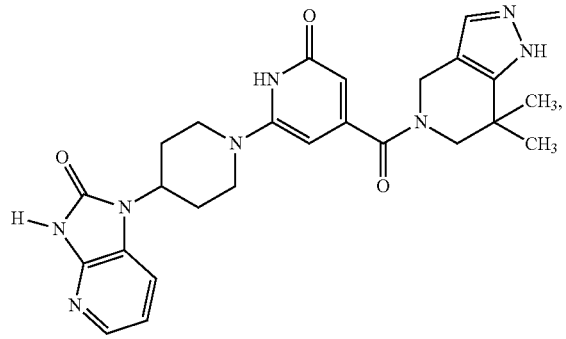 |
| (13) | 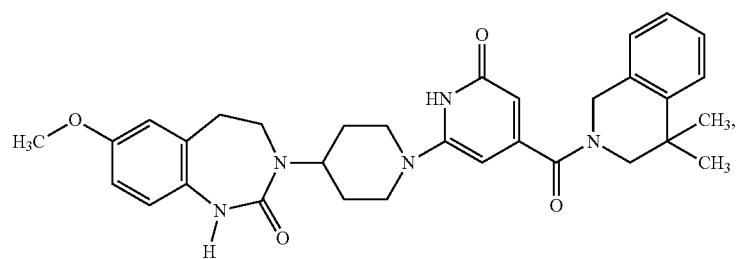 |
| (14) | 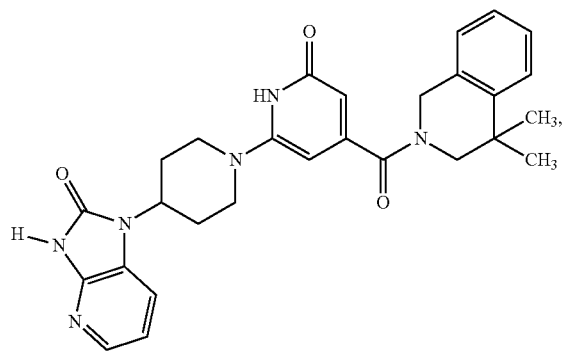 |
| (15) | 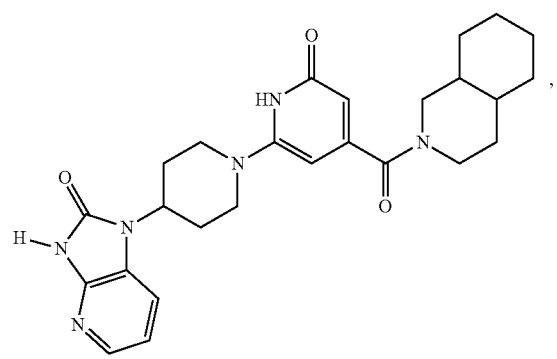 |

| No. | Structure |
|---|---|
| (16) | 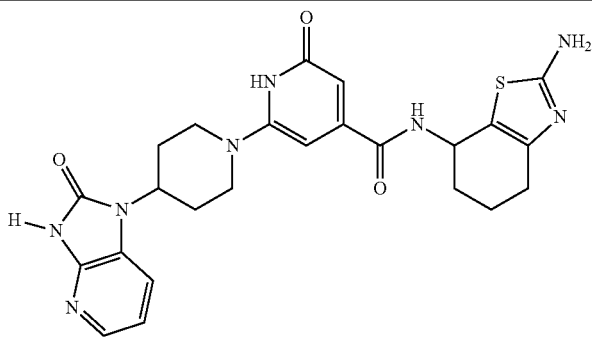 |
| | and |
| (17) | 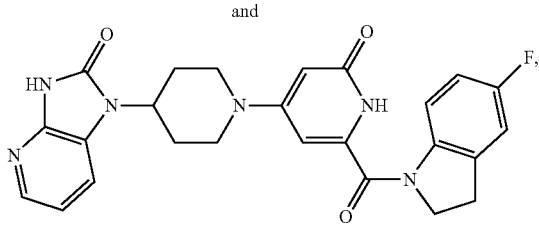 | or a tautomer or salt thereof.

15. A physiologically acceptable salt of a compound according to any one of claims 1 to 14.

16. A pharmaceutical composition comprising a compound according to any one of claims 1 to 14 or a physiologically acceptable salt thereof together with an inert carrier or diluent.

17. A method for treating tension headache, migraine headache or cluster headache which method comprises administering to a host suffering from the same a therapeutically effective amount of a compound according to any one of claims 1 to 14 or a physiologically acceptable salt thereof.

* * * * *